United States Patent
Booth et al.

(10) Patent No.: US 6,800,656 B2
(45) Date of Patent: Oct. 5, 2004

(54) TRICYCLIC COMPOUNDS AND METHOD OF TREATING HERPES VIRUS

(75) Inventors: Richard John Booth, Ann Arbor, MI (US); Vara Prasad Venkata Nagendra Josyula, Ann Arbor, MI (US); Annette Lynn Meyer, Brighton, MI (US); Bruce Allan Steinbaugh, Chelsea, MI (US)

(73) Assignee: Warner Lambert Company, Ann Arbor, MI (US)

( * ) Notice: Subject to any disclaimer, the term of this patent is extended or adjusted under 35 U.S.C. 154(b) by 0 days.

(21) Appl. No.: 10/169,590

(22) PCT Filed: Nov. 30, 2000

(86) PCT No.: PCT/US00/32571

§ 371 (c)(1),
(2), (4) Date: Jul. 5, 2002

(87) PCT Pub. No.: WO01/51479

PCT Pub. Date: Jul. 19, 2001

(65) Prior Publication Data

US 2003/0229073 A1 Dec. 11, 2003

Related U.S. Application Data

(60) Provisional application No. 60/174,883, filed on Jan. 7, 2000.

(51) Int. Cl.[7] .................. C07D 307/91; C07D 333/76; A61K 31/381; A61K 31/343; A61P 31/22
(52) U.S. Cl. .................. 514/443; 549/43; 549/460; 514/468; 544/37; 544/102; 544/348; 546/104; 540/468; 540/479; 540/557; 540/577; 540/471; 540/586
(58) Field of Search .................. 549/43, 460; 514/443, 514/468

(56) References Cited

U.S. PATENT DOCUMENTS

| | | | |
|---|---|---|---|
| 2,990,368 A | 6/1961 | Thompson | 252/40.7 |
| 3,413,291 A | 11/1968 | Sparks | 260/244 |
| 3,592,819 A | 7/1971 | Fleming et al. | 260/294.7 |
| 3,673,191 A | 6/1972 | Albrecht et al. | 260/293.57 |
| 3,929,802 A | 12/1975 | Albrecht et al. | 260/293.58 |
| 3,932,424 A | 1/1976 | Albrecht et al. | 260/293.61 |
| 5,049,464 A | * 9/1991 | Kanemaru et al. | 430/58.15 |

FOREIGN PATENT DOCUMENTS

| | | |
|---|---|---|
| DE | 19813979 A | 9/1999 |
| GB | 863550 A | 4/1957 |
| GB | 1040737 A | 9/1966 |
| GB | 1268772 A | 3/1972 |
| JP | 10101591 A | 4/1998 |
| WO | WO 95/04723 A | 2/1995 |
| WO | WO98/30544 A | 7/1998 |

OTHER PUBLICATIONS

Cecil Textbook of Medicine, 20th Edition, vol. 2, pp. 1739–1747.*
Dunkerton et al. (Journal of Heterocyclic Chemistry (1987), 24(3), 749–55).*
Hagen, et al., Synthesis of 6–substituted beta–carbolines that behave as benzodiazepine receptor antagonists or inverse agonists, J. Med. Chem., 30:750–753 (1987).
Chemical Abstracts, vol. 128, No. 28 (1998).
Chemical Abstracts, vol. 94, No. 23 (1981).
Chemical Abstracts, vol. 36, No. 14 (1942).
Chemical Abstracts, vol. 63, No. 7 (1965).
Chemical Abstracts, vol. 127, No. 17 (1997).
Chemical Abstracts, vol. 77, No. 17 (1972).
Chemical Abstracts, vol. 111, No. 24 (1989).
Chemical Abstracts, vol. 108, No. 10 (1988).
Wang, et al., Hepatitis C Viral IRES Inhibition by Phenazine and Phenazine–Like Molecules, Bio & Medic Chem Ltrs 10:1151–1154 (2000).
International Search Report for PCT/US00/32571 filed on Nov. 30, 2000.

* cited by examiner

Primary Examiner—Mark L. Berch
Assistant Examiner—Kahsay Habte
(74) Attorney, Agent, or Firm—Karl Neidert; Bryan C. Zielinski; Peter Richardson

(57) ABSTRACT

The present invention provides a compound of the formula and pharmaceutically acceptable salts having useful antiviral activity against viruses of the herpes family.

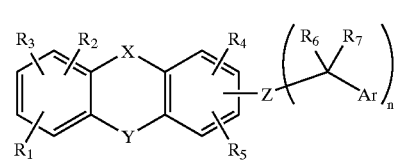

Wherein:
  X=O, $(CH_2)_m$, S, SO, $SO_2$, NH, $NR_8$;
  Y=O, $(CH_2)_m$, S, SO, $SO_2$, NH, $NR_8$ or a chemical bond;
  Z=NH, O, $NR_8$, S, SO, $SO_2$;
The remaining substituents are described in the specification.

13 Claims, No Drawings

TRICYCLIC COMPOUNDS AND METHOD OF TREATING HERPES VIRUS

This application is a 371 of PCT/US00/32571 filed on Nov. 30, 2000 which claims benefit of Ser. No. 60/174,883 Jan. 7, 2000.

FIELD OF THE INVENTION

The present invention relates to compounds possessing antiviral activity against viruses of the herpes family, or a composition containing them. These compounds provide a method for treating herpes viral infections, including condition caused by herpes simplex I such as cold sores, herpes simplex II such as genital herpes, as well as shingles caused by herpes zoster and infections caused by cytomegalovirus, Epstein Barr Virus.

BACKGROUND OF INVENTION

Various subfamilies of herpes viruses (Herpes viridae) exist: α-herpesvirinae, β-herpesvirinae, γ-herpesvirinae and cercopithecing Herpes virus I (3 virus); some specific viruses are: Herpes simplex virus-I (HSV-1), Herpes simplex virus-2 HSV-2), Cytomegalovirus (CMV), Varicella Zoster virus (VZV), Epstein-Barr virus (EBV), human herpes virus-6 (HHV-6), human herpes virus-7 (HHV-7), human herpes virus-8 (HHV) as well as others which may not yet be defined.

The incidence of infections by Herpes simplex virus is very high throughout the world. Serological studies showed that herpes viral infections affect a substantial percentage of the population. Reactivation of herpes virus infections may lead to recurrent infections. The risk of severe diseases increases with decreasing immunocompetence of the host. There is a pressing need for improved therapy for treating this disease. Currently, exclusive of vaccines, treat involves primarily nucleoside drugs such as acyclovir, which target thymidine kinase and suffer from development of resistance.

SUMMARY OF THE INVENTION

The present invention provides a compound of the formula and its pharmaceutically acceptable salts, or the compound and its pharmaceutical composition having useful antiviral activity against viruses of the herpes family.

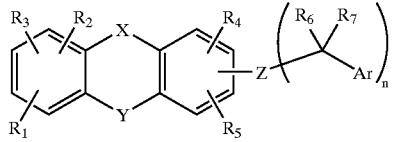

I wherein:
X=O, $(CH_2)_m$, S, SO, $SO_2$, $NR_8$ or a chemical bond;
Y=O, $(CH_2)_m$, S, SO, $SO_2$, NH, $NR_8$;
Z=N, NH, O, $NHR_8$, S, SO, $SO_2$;
n=an integer of from 0 to 2;
m=an integer of 1, 2, or 3;
$R_1$, $R_2$, $R_3$, $R_4$, $R_5$ independently are hydrogen, halogen, hydroxyl amino, mono or dialkylamino, cyano, nitro, alkyl groups (1–6 carbon atoms), alkoxy groups (1–6 carbon atoms), $CF_3$, $OCF_3$, aminoalkyl (1–6 carbon atoms), aminoaryl, Oaryl, or a heterocyclic ring having 5–7 atoms with 1–4 hetero atoms of N, O, or S;
Ar=phenyl,
substituted phenyl,
benzoheterocyclic ring,
substituted benzoheterocyclic ring,
heterocyclic ring, or
substituted heterocyclic ring, which have substitutions $R_6$ or $R_7$;
$R_4$ and $R_7$ are independently hydrogen, alkyl group (1–6 carbon atoms), cycloalkyl (3–12 carbon atoms), halogen, alkoxy, $CF_3$, aminoalkyl (1–6 carbon atoms), aminoaryl, or a heterocyclic ring of from 5–7 atoms with 1–4 heteroatoms of N, O or S;
$R_6$ and $R_7$ may also form a ring, optionally cycloalkyl or aryl or substituted aryl; $R_8$ is hydrogen, alkyl (1–6 carbon atoms), cycloalkyl (3–12 carbon atoms), phenyl or substituted phenyl wherein the substituents are as defined above.

The invention also provides for a pharmaceutical composition for the treatment of infection or disease caused by a virus, optionally a Herpes virus which comprises an amount of the compound of claim 1 sufficient to provide an antivirally effective dosage of the compound of Formula I and a pharmaceutically effective carrier.

The invention also provides for a method of treatment of infection or disease caused by a virus, optionally a Herpes virus which comprises administering to a subject in need of such treatment an effective antivirally dosage of a composition of formula I.

DESCRIPTION OF PREFERRED EMBODIMENTS

The present invention pertains to anti viral compounds. Preferred compounds are as follows:

One preferred compound is:

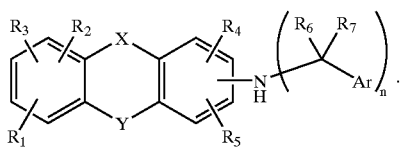

II

Another preferred compound is:

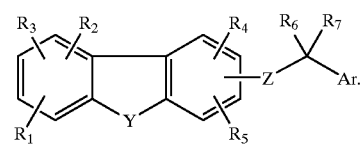

III

Another preferred compound is:

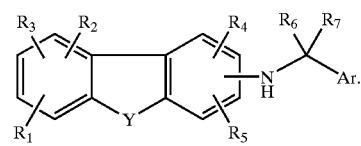

IV

Another preferred compound is:

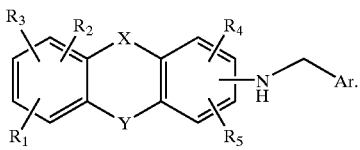

V

Another preferred compound is:

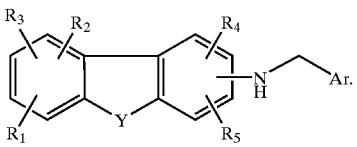

VI

Another preferred compound is:

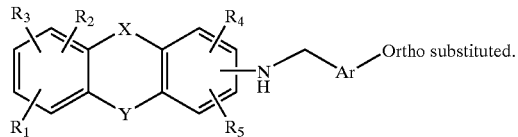

VII

Another preferred compound is:

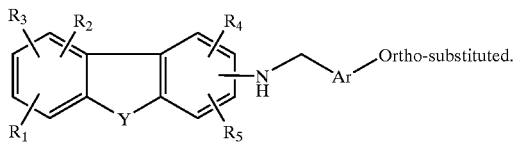

VIII

The term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, n-pentyl, n-hexyl, n-heptyl, n-octyl n-nonyl, n-decyl, undecyl, and dodecyl. The alkyl group may be unsubstituted or independently substituted by from 1 to 3 substituents selected from F, Cl, Br, I, OH, $NH_2$, SH, CN, $NO_2$, $OCH_3$, $OCH_2CH_2OH$, $NHCH_3$, or $N(CH_3)_2$.

The term "cycloalkyl" means a hydrocarbon ring which contains from 3 to 12 carbon atoms unless otherwise specified, for example, cyclopropyl, cyclobutyl, cyclopentyl, cyclohexyl, and adamantyl. Where possible, the cycloalkyl group may contain double bonds. The cycloalkyl ring may be unsubstituted or substituted by from 1 to 3 substituents selected from alkyl, cycloalkyl alkoxy, thioalkoxy all as defined herein, hydroxy, thiol, nitro, halogen, amino, formyl, carboxyl, nitrile, —NH—CO—R, —CO—NHR—, —$CO_2R$, —COR, aryl, or heteroaryl wherein alkyl (R), aryl, and heteroaryl are defined as herein.

The term "alkoxy" having 1–6 carbon atoms means a $C_1$–$C_6$ alkyl-O— group or radical wherein $C_1$–$C_6$ alkyl has the meaning as defined above. Illustrative examples of a straight or branched alkoxy group or radical having from 1 to 6 carbon atoms, also known as a $C_1$–$C_6$ alkoxy, include methoxy, ethoxy, 1-propoxy, 2-propoxy, 1-butoxy, 2-butoxy, 2-methyl-1-propoxy, and 1,1-dimethylethoxy, 1-pentoxy, 2-pentoxy, 3-pentoxy, 2,2-dimethylpropoxy, 1-hexoxy, 2-hexoxy, 3-hexoxy, and 4-methyl-1-pentoxy.

The term "thioalkoxy" having 1–6 carbon atoms means a $C_1$–$C_6$ alkyl-S— group or radical wherein $C_1$–$C_6$ alkyl has the meaning as defined above. Illustrative examples of a straight or branched thioalkoxy group or radical having from 1 to 6 carbon atoms, also known as a $C_1$–$C_6$ thioalkoxy, include methylthio, ethylthio, 1-propylthio, 2-propylthio, 1-butylthio and 2-butylthio, 1-pentylthio, 2-pentylthio, 3-pentylthio, 2,2-dimethylpropylthio, 1-hexylthio, 2-hexylthio, 3-hexylthio, and 4-methyl-1-pentylthio.

The term "aryl" means an aromatic carbocyclic ring having from 6 to 10 carbon atoms. Illustrative examples of an aryl group or radical include phenyl, 1-naphthyl, and 2-napthyl. The aryl group may be unsubstituted or independently substituted by from 1 to 3 substituents selected, unless otherwise specified, from F, Cl, Br, I, OH, $NH_2$, SH, CN, $NO_2$, $OCH_3$, $OCH_2CH_2OH$, $NHCH_3$, or $N(CH_3)_2$.

The term "Oaryl" means an aryl-O— group or radical wherein aryl has the meaning as defined above. Illustrative examples of an Oaryl group or radical include phenoxy, 1-naphthyloxy, and 2-napthyloxy. Oaryl groups may be unsubstituted or independently substituted by from 1 to 3 substituents selected, unless otherwise specified, from F, Cl, Br, I, OH, $NH_2$, SH, CN, $NO_2$, $OCH_3$, $OCH_2CH_2OH$, $NHCH_3$, or $N(CH_3)_2$.

The term "halogen" means bromine, chlorine, fluorine or iodine.

The term "monoalkylamino" means an NH-alkyl group or radical wherein alkyl has the meaning as defined above.

The term "dialkylamino" means an N-(alkyl)$_2$ group or radical wherein alkyl has the meaning as defined above.

The term "aminoalkyl" having 1–6 carbon atoms means an $H_2N$—($C_1$–$C_6$ alkyl)-group or radical wherein $C_1$–$C_6$ alkyl has the meaning as defined above. The aminoalkyl group is a substituted $C_1$–$C_6$ alkyl group or radical containing at least one substituent which is $NH_2$.

The term "aminoaryl" means an $H_2N$-aryl-group or radical wherein aryl has the meaning as defined above. The aminoaryl group is a substituted aryl group or radical containing at least one substituent which is $NH_2$.

The term "carbocycle" means cycloalkyl as defined above.

The term "heteroatom" means a nitrogen, sulfur, or oxygen.

The term "heterocycle" means a heterocyclic radical which are 5–7 atoms having 14 heteroatons and are selected from: furan, pyrrole, thiophene, oxazole, isoxazole, thiazole, pyrazole, 1,2,3-triazole, 1,2,4-triazole, tetrazole, pyridine, pyridazine, pyrimidine, pyrazine, tetrahydrofuran, tetrahydrothiophene, pyrrolidine, piperazine, piperidine, morpholine, thiomorpholine, oxolane, dioxane, sulfolane, unsubstituted or substituted by 1 to 2 substituents selected from alkyl as defined above. For heterocycles containing sulfur, the oxidized sulfur heterocycles containing SO or $SO_2$ groups are also included.

The term "benzoheterocyclic ring" ("fused heterocycle") refers to a heterocycle that is adjoined at two consecutive positions with a phenyl ring or another heterocycle, such rings may include 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

Some of the compounds of Formula I are capable of further forming pharmaceutically acceptable acid-addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salt thus include sulfate, pyrosulfate, bisulfate, sulfite, bisulfite, nitrate, phosphate, monohydrogenphosphate, dihyrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66: 1–19.

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. Configuration drawn is most preferred.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of a virus, as agents for the treatment of infections caused by a virus or as agents for the treatment of diseases due to a virus, the compounds utilized in the pharmaceutical method of this invention are administered at the initial dosage of about 0.01 mg to about 100 mg/kg daily. A daily dose range of about 0.01-mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

General Procedure 1 (for Singleton Synthesis)
Reductive Amination of Aryl Amines with Aldehydes or Ketones.

Reagent 2 (1 eq.) was taken in a solvent (dichloromethane, 1,2-dichloroethane or tetrahydrofuran or diethyl ether) and to it reagent 1 (1 to 1.2 eq.) was added. To this solution cooled at 0° C. was added a reducing agent (sodium cyanoborohydride or sodium triacetoxyborohydride) (1 to 2 eq.). To it a drop of acetic acid was added and kept under stirring at room temperature for 6 to 24 hours. The excess hydride was quenched by adding methanol. The reaction mixture was diluted with ethyl acetate and washed with saturated ammonium chloride solution, aqueous sodium bisulfite and brine; dried over anhydrous magnesium sulfuate or sodium sulphate. Organic layer was concentrated and crude product was purified by flash silica gel chromatography to afford the final product. The products were characterized by spectral data. The compounds synthesized using this procedure are shown in Table 4.

General Procedure 2 for Multiple, Simultaneous Solution Phase Synthesis (Combinatorial Chemistry Synthesis)

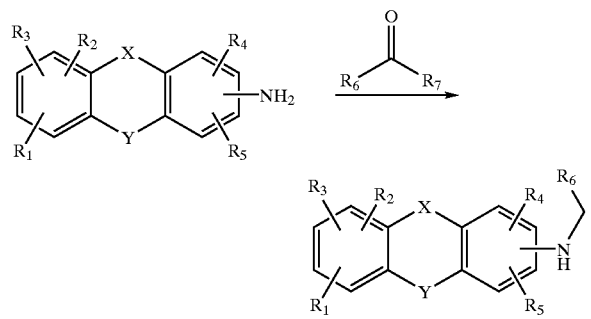

To a 2-dram glass vial were added, by Tecan liquid handling robot, a solution of reagent 2 (0.05 mmol) in trimethyl orthoformate (0.2 ml) followed by reagent 1 (0.05 mmol) in trimethyl orthoformate (0.2 ml). The vial was capped and the reaction mixture was shaken at room temperature for 18 hours (overnight), then concentrated to dryness. To each vial was added, by Tecan™ liquid handling robot, 1,2-dichloroethane (1 ml). Solid sodium triacetoxyborohydride (~23mg) was added manually to each vial. A solution of acetic acid (0.05 mmol) in dichloroethane (0.05 ml) was added to each vial by Tecan™ liquid handling robot. The vial was again capped and the reaction mixture was shaken at room temperature for 18 hours (overnight). To the reaction mixture was added, by Tecan liquid handling robot, methanol (1 ml). The reaction nature was then transferred, by Tecan liquid handling robot, to be prewashed (That is washed with methanol (2 ml) and dichloroethane (1 ml)) BAKERBOND spe™ Aromatic Sulfonic Acid ($SO_3M$) disposable Extraction Columns. The columns were allowed to drain and then washed with methanol (2×1 ml) these solvents were discarded. The desired product was eluted from the column using a solution of 2M ammonia in methanol (3×1 ml) and concentrated to dryness in a tared 2-dram vial. The product was analyzed by LCMS (liquid chromotography mass spec).

General Procedure 3 for Multiple, Simultaneous Solution Phase Synthesis (Combinatorial Chemistry Synthesis)

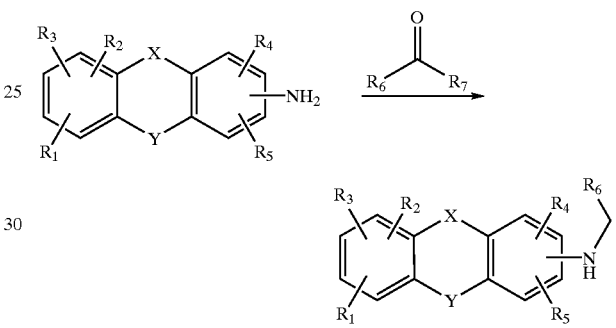

To a 2-dram glass vial were added, by Tecan™ liquid handling robot, a solution of reagent 2 (0.05 mmol) in N,N-di-methylformamide (0.1 ml) followed by reagent 1 (0.05 mmol) in N,N-dimethylformnamide (0.1 ml). Each vial was treated with trimethylorthoformate (0.2 ml) by Tecan™ liquid handling robot. The vial was capped and the reaction mixture was shaken at room temperature for 18 hours (overnight), then concentrated to dryness. To each vial was added, by Tecan™ liquid handling robot 1,2-dichloroethane (1 ml). Solid sodium triacetoxyborohydride (~23mg) was added manually to each vial. A solution of acetic acid (0.05 mmol) in 1,2-dichloroethane (0.05 ml) was added to each vial by Tecan™ liquid handling robot The vial was again capped and the reaction mixture was shaken at room temperate for 18 hours (overnight). To the reaction mixture was added, by Tecan™ liquid handling robot, methanol (1 ml). The reaction mixture was then transferred, by Tecan™ liquid handling robot, to be prewashed (That is washed with methanol (2 ml) and 1,2-dichloroethane (1 ml)) BAKERBOND spe™ Aromatic Sulfonic Acid ($SO_3H$) disposable Extraction Columns. The columns were allowed to drain and then washed with methanol (2×1 ml) these solvents were discarded. The desired product was eluted from the column using a solution of 2M ammonia in methanol (3×1 ml) and concentrated to dryness in a tared 2-dram vial. The product was analyzed by LCMS (liquid chromatography mass spec).

General Procedure 4 for Multiple, Simultaneous Solution Phase Synthesis (Combinatorial Chemistry Synthesis)

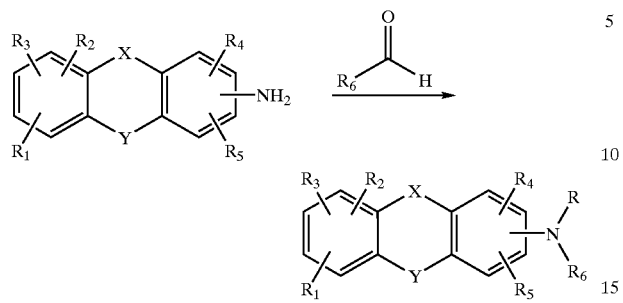

To a 2-dram glass vial were added, by Tecan™ liquid handling robot, a solution of reagent 2 (0.05 mmol) in methanol (0.2 ml) followed by reagent 1 (0.2 mmol) in methanol (0.2 ml). To each vial was added, by Tecan™ liquid handling robot, a 1N solution of sodium cyanoborohydride in methanol (0.2 ml) and a 10% a acetic acid in methanol (0.05 ml) solution. The vial was capped and the reaction mixture was shaken at room temperature for 18 hours (overnight), then concentrated to dryness. The vial was again capped and the reaction mixture was shaken at room temperature for 18 hours (overnight). To the reaction mixture was added, by Tecan™ liquid handling robot, methanol (1 ml). The reaction mixture was then transferred, by Tecan™ liquid handling robot, to be prewashed (That is washed with methanol (2 ml) and 1,2-dichloroethane (1 ml)) BAKERBOND spe™ Aromatic Sulfonic Acid (SO$_3$H) disposable Extraction Columns. The columns were allowed to drain and then washed with methanol (2×1 ml) these solvents were discarded. The desired product was eluted from the column using a solution of 2M ammonia in methanol (3×1 ml) and concentrated to dryness in a tared 2-dram vial. The product was analyzed by LCMS (liquid chromatography mass spec).

General Procedure 5 for Multiple, Simultaneous Solution Phase Synthesis (Combinatorial Chemistry Synthesis)

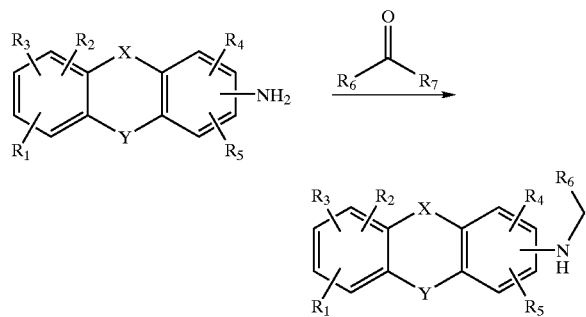

To a 2-dram glass vial were added, by Tecan™ liquid handling robot, a solution of reagent 2 (0.05 mmol) in 1,2-dichloroethane (0.2 ml) followed by reagent 1 (0.15 mmol) in 1,2-dichloroethane (0.1 ml). To each vial solid sodium triacetoxyborohydride (~25 mg) was added manually. A solution of acetic acid (0.05 mmol) in 1,2-dichloroethane (0.05 ml) was added to each vial by Tecan™ liquid handling robot. The vial was capped and the reaction mixture was shaken at room temperature for 18 hours (overnight). To the reaction mixture was added, by Tecan™ liquid handling robot, methanol (1 ml). The reaction mixture was then transferred, by Tecan™ liquid handling robot, to be prewashed (washed with methanol (2 ml) and 1,2-dichloroethane (1 ml)) BAKERBOND spe™ Aromatic Sulfonic Acid (SO$_3$H) disposable Extraction Columns. The columns were allowed to drain and then washed with methanol (2×1 ml) these solvents were discarded. The desired product was eluted from the column using a solution of 2M ammonia in methanol (3×1 ml) and concentrated to dryness in a tared 2-dram vial. The product was analyzed by LCMS (liquid chromatography mass spec).

General Procedure 6 for Multiple, Simultaneous Solution Phase Synthesis (Combinatorial Chemistry Synthesis)

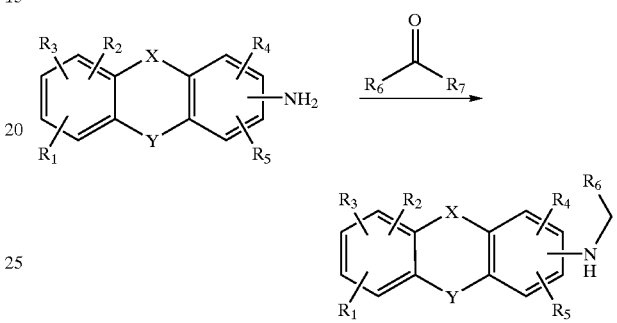

To a 2-dram glass vial were added, by Tecan™ liquid handling robot, a solution of reagent 2 (0.05 mmol) in methanol (0.2 ml) followed by reagent 1 (0.15 mmol) in methanol (0.1 ml). To each vial was added a 1N solution of sodium cyanoborohydride in methanol (0.1 ml) and a 10% acetic acid in methanol solution (0.05 ml). The vial was capped and the reaction mixture was shaken at room temperature for 18 hours (overnight). To the reaction mixture was added, by Tecan™ liquid handling robot, methanol (1 ml). The reaction mixture was then transferred, by Tecan™ liquid handling robot, to be prewashed (washed with methanol (2 ml) and 1,2-dichloroethane (1 ml)) BAKERBOND spe™ Aromatic Sulfonic Acid (SO$_3$H) disposable Extraction Columns. The columns were allowed to drain and then washed with methanol (2×1 ml) these solvents were discarded. The desired product was eluted from the column using a solution of 2M ammonia in methanol (3×1 ml) and concentrated to dryness in a tared 2-dram vial. The product was analyzed by LCMS (liquid chromatography mass spec).

General Procedure 7 for Multiple, Simultaneous Solution Phase Synthesis (Combinatorial Chemistry Synthesis)

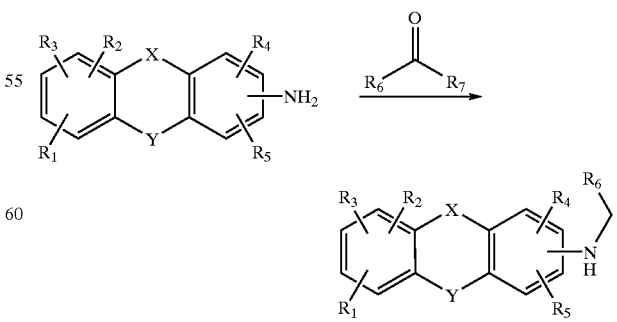

To a 2-dram glass vial were added, by Tecan™ liquid handling robot, a solution of reagent 2 (0.05 mmol) followed by reagent 1 in N,N-dimethylformamide (0.32 ml) or methanol (0.2 ml). The vials were then concentrated overnight to dryness. Each vial was treated by Tecan™ liquid handling robot with reagent 1 (0.15 mmol) in methanol (0.1 ml) and methanol (0.2 ml). To each vial was added a 1N solution of sodium cyanoborohydride in methanol (0.1 ml) and a 10% acetic acid in methanol solution (0.05 ml). The vial was capped and the reaction mixture was shaken at room temperature for 18 hours (overnight). To the reaction mixture was added, by Tecan™ liquid handling robot, methanol (1 ml). The reaction mixture was then transferred, by Tecan™ liquid handling robot, to be prewashed (washed with methanol (2 ml) and 1,2-dichloroethane (1 ml)) BAKERBOND spe™ Aromatic Sulfonic Acid (SO₃H) disposable Extraction Columns. The columns were allowed to drain and then washed with methanol (2×1 ml) these solvents were discarded. The desired product was eluted from the column using a solution of 2M ammonia in methanol (3×1 ml) and concentrated to dryness in a tared 2-dram vial. The product was analyzed by LCMS (liquid chromatography mass spec).

Synthesis of Compound 450: To dibenzofuran-2-yl-amine (0.91 g, 5 mmol) taken in dichloromethane (75 mL) was added α,α'-dibromo-ortho-xylene (1.85 g, 7 mmol) followed by triethylamine (3.03 g, 30 mmol). The reaction was stirred at room temperature for 24 hours. The solvents were evaporated and the residue was purified by flash silica gel chromatography to give the title compound (1.43 g).

Synthesis of Compound 451: To dibenzofuran-2-yl-amine (0.91 g, 5 mmol) taken in dichloromethane (75 mL) was added phthaloyl dichloride (1.16 g, 6 mmol) followed by triethylamine (3.03 g, 30 mmol). The reaction was stirred at room temperature for 5 minutes. The reaction was quenched with sodium bicarbonate solution and the organic layer was separated. The crude product was purified by flash silica gel chromatography to give the title compound (0.51 g).

Synthesis of Compound 463: To compound 58 (0.25 g, 0.87 mmol) taken in tetrahydrofuran (10 mL) was added sodium hydride (60% in mineral oil, 0.035 g, 0.87 mmol). To it methyl iodide (0.25 g, 1.74 mmol was added. The reaction was stirred at room temperature for 24 hours. The solvents were evaporated and the residue was purified by flash silica gel chromatography to give the title compound (0.18 g).

Deprotection of t-butyloxycarbonyl group: The general procedure for the removal of tert-butyoxycarbonyl (Boc) group is as follows: To the compound taken a flask was added hydrochloric acid in an appropriate solvent (dioxane, methanol, 1,2-dichloromethane and the reaction was kept under shaking for 5 to 18 hours. Removal of volatiles furnished the corresponding product.

Reagents 1 are shown in Table 1.

TABLE 1

| No. | Reagent 1 (aldehydes/ketones) |
|---|---|
| 1 | o-tolualdehyde |
| 2 | meta-tolualdehyde |
| 3 | para-tolualdehyde |
| 4 | 2-fluorobenzaldehyde |
| 5 | 3-fluorobenzaldehyde |
| 6 | 4-fluorobenzaldehyde |
| 7 | 4-tert-butylbenzaldehyde |
| 8 | α,α,α-Trilfluoro-o-tolualdehyde |
| 9 | α,α,α-Trilfluoro-m-tolualdehyde |
| 10 | α,α,α-Trilfluoro-p-tolualdehyde |
| 11 | o-anisaldehyde |
| 12 | m-anisaldehyde |

TABLE 1-continued

Aldehydes/ketones (reagent 1)

| No. | Reagent 1 (aldehydes/ketones) |
|---|---|
| 13 | p-anisaldehyde |
| 14 | Salicylaldehyde |
| 15 | 3-hydroxybenzaldehyde |
| 16 | 4-hydroxybenzaldehyde |
| 17 | 2-chlorobenzaldehyde |
| 18 | 3-chlorobenzaldehyde |
| 19 | 4-chlorobenzaldehyde |
| 20 | 3-benzyloxybenzaldehyde |
| 21 | 4-benzyloxybenzaldehyde |
| 22 | 2,3-dimethoxybenzaldehyde |
| 23 | 2,4-dimethoxybenzaldehyde |
| 24 | 2,5-dimethoxybenzaldehyde |
| 25 | 2,6-dimethoxybenzaldehyde |
| 26 | 3,4-dimethoxybenzaldehyde |
| 27 | 3,5-dimethoxybenzaldehyde |
| 28 | 1,4-Benzodioxan-6-carboxaldehyde |
| 29 | 2,4-dimethylbenzaldehyde |
| 30 | 2,5-dimethylbenzaldehyde |
| 31 | 2,3-difluorobenzaldehyde |
| 32 | 2,4-difluorobenzaldehyde |
| 33 | 2,5-difluorobenzaldehyde |
| 34 | 2,6-difluorobenzaldehyde |
| 35 | 3,4-difluorobenzaldehyde |
| 35 | 3,5-difluorobenzaldehyde |
| 37 | 2,3,4-trifluorobenzaldehyde |
| 38 | 2,3,6-trifluorobenzaldehyde |
| 39 | 3-fluoro-2-methylbenzaldehyde |
| 40 | 3-fluoro-p-anisaldehyde |
| 41 | 2-pyridinecarboxaldehyde |
| 42 | 3-pyridinecarboxaldehyde |
| 43 | 4-pyridinecarboxaldehyde |
| 44 | 4-pyridinecarboxaldehyde N-oxide |
| 45 | 6-methyl-2-pyridinecarboxaldehyde |
| 46 | 3-furaldehyde |
| 47 | 2-furaldehyde |
| 48 | 5-chloro-2-thiophenecarboxaldehyde |
| 49 | 3-thiophenecarboxaldehyde |
| 50 | 2-thiophenecarboxaldehyde |
| 51 | pyrrole-2-carboxaldehyde |
| 52 | 1-methyl-2-pyrrolecarboxaldehyde |
| 53 | 1-naphthaldehyde |
| 54 | 2-naphthaldehyde |
| 55 | 2-quinolinecarboxaldehyde |
| 56 | 3-quinolinecarboxaldehyde |
| 57 | 4-quinolinecarboxaldehyde |
| 58 | indole-3-carboxaldehyde |
| 59 | 2-bromobenzaldehyde |
| 60 | 2-chlorobenzaldehyde |
| 61 | 2-ethoxybenzaldehyde |
| 62 | 2-cyanobenzaldehyde |
| 63 | 5-(2-chlorophenyl)furfural |
| 64 | 5-(3-chlorophenyl)furfural |
| 65 | 5-(4-chlorophenyl)furfural |
| 66 | 2-thiazolecarboxaldehyde |
| 67 | 2-imidazolecarboxaldehyde |
| 68 | 4(5)-imidazolecaboxaldehyde |
| 69 | 5-nitro-2-thiophenecarboxaldehyde |
| 70 | 2-nitrobenzaldehyde |
| 71 | 4-formyluracil |
| 72 | 4-acetoxybenzaldehyde |
| 73 | 4-(dimethylamino)benzaldehyde |
| 74 | 1-acetyl-3-indolecarboxaldehyde |
| 75 | 4-bromo-2-thiophenecarboxaldehyde |
| 76 | Piperonal |
| 77 | 3-trifluoromethoxybenzaldehyde |
| 78 | 4-chloro-3-nitro-benzaldehyde |
| 79 | Benzaldehyde |
| 80 | 3-benzyloxybenzaldehyde |
| 81 | 3-phenoxybenzaldehyde |
| 82 | 2-butanone |
| 83 | 2-Pentanone |
| 84 | 3-Methyl-2-butanone |
| 85 | Tetrahydrothiophene-3-one |
| 86 | Tetrahydrothiopyran-4-one |
| 87 | Cycloheptanone |

TABLE 1-continued

Aldehydes/ketones (reagent 1)

| No. | Reagent 1 (aldehydes/ketones) |
|---|---|
| 88 | Cyclooctanone |
| 89 | Cyclohexylmethylketone |
| 90 | 4-Methyl-2-pentanone |
| 91 | 3-Pentanone |
| 92 | 3-Hexanone |
| 93 | 4-Hydroxy-3-methyl-2-butanon |
| 94 | 2-Methoxyphenylacetone |
| 95 | 4-nitrobenzaldehyde |
| 96 | 4-(methylthio)benzaldehyde |
| 97 | Propionaldehyde |
| 98 | Isovaleraldehyde |
| 99 | 3-(methylthio)propionaklehyde |
| 100 | 1-phenyl-2-pentanone |
| 101 | Acetone |
| 102 | Cyclopropyl methyl ketone |
| 103 | Cyclohexanone |
| 104 | n-tert-butoxycarbonyl-4-piperidone |
| 105 | 3,3,5,5-tetramethylcyclohexanone |
| 106 | 1-decalone |
| 107 | 4-cyclohexylcyclohexanone |
| 108 | 2-norbornanone |
| 109 | 4-tert-butylcyclohexanone |
| 110 | Cyclopentanone |
| 111 | 2-adamantanone |
| 112 | Bicyclo[3,2,1]octan-2-one |
| 113 | 1,1-dioxo-tetrahydro-thiopyran-4-one |

Reagent 2 (amines) used in the above general procedures are shown in Table 2:

TABLE 2

| No. | Reagent 2 (amines) |
|---|---|
| 1 | Dibenzofuran-2-yl-methyl-amine |
| 2 | 8-fluoro-dibenzofuran-2-yl-amine |
| 3 | 8-chloro-dibenzofuran-2-yl-amine |
| 4 | 8-amino-dibenzofuran-2-ol |
| 5 | 3-methoxy-diebenzofuran-2-yl-amine |
| 6 | 9H-Fluoren-3-yl-amine |
| 7 | 9H-Fluorene-2-yl-amine |
| 8 | Dibenzofuran-4-yl-amine |
| 9 | Benzo[4,5]furo[2,3-H]pyridin-3-yl-amine |
| 10 | 9-Ethyl-9H-carbazol-3-ylamine |
| 11 | 3-Amino-carbazole-9-carboxylic acid tert-butyl ester |
| 12 | Dibenzofuran-2-yl-methyl-amine |
| 13 | Dibenzofuran-2-yl-dimethyl-amine |
| 14 | Dibenzothiophene-2-yl-amine |
| 15 | Dibenzothiophene-3-yl-amine |
| 16 | 6-Amino-1,2,3,4-tetrahydro-carbazole-9-carboxylic acid tert-butyl ester |
| 17 | Dibenzo[1,4]dioxin-2-yl-amine |
| 18 | Phenoxanthiin-3-yl-amine |
| 19 | 10-Oxa-9-thia-1-aza-anthracen-3-yl-amine |
| 20 | 10H-Benzo-b]pyrido[2,3-e][1,4]oxazin-3-ylamine acetic acid, tert-butyl ester |
| 21 | Anthracen-2-yl-amine |
| 22 | 10,111-Dihydro-5H-diebnzo[b,f]azepin-3-yl-amine |
| 23 | 6,7,8,9-Tetrahydro-5H-carbazol-3-yl-amine |
| 24 | 7-Amino-1-aza-phenoxathiin |

The compounds of Formula I include:

1. (1-Cyclopropyl-ethyl)-(2-methoxy-dibenzofuran-3-yl)-amine
2. Cyclopentyl-(9H-fluoren-2-yl)-amine
3. (1-Cyclopropyl-ethyl)-(9H-fluoren-2-yl)-amine
4. $N^3$-Cyclopentyl-$N^2,N^2$-dimethyl-9H-fluorene-2,3-diamine
5. Isopropyl-(2-methoxy-dibenzofuran-3-yl)-amine
6. (2-Methoxy-dibenzofuran-3-yl)-(terahydro-thiopyran-4-yl)-amine
7. Cycloheptyl-(2-methoxy-dibenzofuran-3-yl)-amine
8. (1-Ethyl-propyl)-(2-methoxy-dibenzofuran-3-yl)-amine
9. sec-Butyl-(2-methoxy-dibenzofuran-3-yl)-amine
10. $N^2,N^2$-Dimethyl-$N^3$-piperidin-4-yl-9H-fluorene-2,3-diamine
11. $N^3$-(1-Benzyl-butyl)-$N^2,N^2$-dimethyl-9H-fluorene-2,3-diamine
12. (9H-Fluoren-2-yl)-piperidin-4-yl-amine
13. (1-Benzyl-butyl)-(9H-fluoren-2-yl-amine
14. sec-Butyl-(9H-fluoren-2-yl)-amine
15. (1,1-Diox-hexahydro-thiopyran-4-yl)-(2-methoxy-dibenzofuran-3-yl)-amine
16. Dibenzofuran-2-yl-(3,3,5,5-tetramethyl-cyclohexyl)-amine
17. (Decahydro-naphthalen-1-yl)-dibenzofuran-2-yl-amine
18. Adamantan-2-yl-dibenzofuran-2-yl-amine
19. Bicyclohexyl-4-yl-dibenzofuran-2-yl-amine
20. Bicyclo[2.2.1]hept-2-yl-dibenzofuran-2-yl-amine
21. (4-tert-Butyl-cyclohexyl)-dibenzofuran-2-yl-amine
22. Bicyclo[3.2.1]oct-2-yl-dibenzofuran-2-yl-amine
23. Cyclopentyl-dibenzofuran-2-yl-amine
24. Cyclohexyl-(2-methoxy-dibenzofuran-3-yl)-amine
25. Cyclohexyl-(9H-fluoren-2-yl)-amine
26. Dibenzofuran-2-yl-bis-(3-methylsulfanyl-propyl)-amine
27. Dibenzofuran-2-yl-bis-(3-methyl-butyl)-amine
28. Dibenzofuran-2-yl-dipropyl-amine
29. $N^3$-(1,1-Dioxo-hexahydro-thiopyran-4-yl)-$N^2,N^2$-dimethyl-9H-fluorene-2,3-diamine
30. $N^3$-Isopropyl-$N^2,N^2$-dimethyl-9H-fluorene-2,3-diamine
31. $N^2,N^2$-Dimethyl-$N^3$-(tetrahydro-thiopyran-4-yl)-9H-fluorene-2,3-diamine
32. $N^3$-Cyclohexyl-$N^2,N^2$-dimethyl-9H-fluorene-2,3-diamine
33. $N^3$-Cyclohexyl-$N^2,N^2$-dimethyl-9H-fluorene-2,3-diamine
34. $N^3$-(1-Ethyl-propyl)-$N^2,N^2$-dimethyl-9H-fluorene-2,3-diamine
35. $N^3$-(1-Cyclopropyl-ethyl)-$N^2,N^2$-dimethyl-9H-fluorene-2,3-diamine -continued

| | |
|---|---|
| 36 | N³-sec-Butyl-N²,N²-dimethyl-9H-fluorene-2,3-diamine |
| 37 | (9H-Fluoren-2-yl)-isopropyl-amine |
| 38 | (9H-Fluoren-2-yl)-(tetahydro-thiopyran-4-yl)-amine |
| 39 | Cycloheptyl-(9H-fluoren-2-yl)-amine |
| 40 | Dibenzofuran-2-yl-(1,1-dioxo-hexahydro-thiopyran-4-yl)-amine |
| 41 | Dibenzofuran-2-yl-piperidin-4-yl-amine |
| 42 | Dibenzofuran 2-yl-isopropyl-amine |
| 43 | Cyclohexyl-dibenzofuran-2-yl-amine |
| 44 | (1-Cyclopropyl-ethyl)-dibenzofuran-2-yl-amine |
| 45 | Dibenzofuran-3-yl-(1,1-dioxo-hexahydro-thiopyran-4-yl)-amine |
| 46 | Dibenzofuran-3-yl-piperidin-4-yl-amine |
| 47 | Dibenzofuran-3-yl-isopropyl-amine |
| 48 | Dibenzofuran-3-yl-(tetrahydro-thiopyran-4-yl)-amine |
| 49 | Cyclohexyl-dibenzofuran-3-yl-amine |
| 50 | Cycloheptyl-dibenzofuran-3-yl-amine |
| 51 | (4-Chloro-benzyl)-dibenzofuran-2-yl-amine |
| 52 | (4-Chloro-3-nitro-benzyl)-dibenzofuran-2-yl-amine |
| 53 | Dibenzofuran-2-yl-(3-trifluoromethyoxy-benzyl)-amine |
| 54 | Benzo[1,3]dioxol-5-ylmethyl-dibenzofuran-2-yl-amine |
| 55 | Dibenzofuran-2-yl-(2,3-dihydro-benzo[1,4]dioxin-6-ylmethyl)-amine |
| 56 | Dibenzofuran-2-yl-(3,5-dimethoxy-benzyl)-amine |
| 57 | Dibenzofuran-2-yl-(4-trifluoromethyl-benzyl)-amine |
| 58 | Dibenzofuran-2-yl-(2-methyl-benzyl)-amine |
| 59 | Dibenzofuran-2-yl-thiophen-3-ylmethyl-amine |
| 60 | Dibenzofuran-2-yl-(4-nitro-benzyl)-amine |
| 61 | Dibenzofuran-2-yl-(4-methylsulfanyl-benzyl)-amine |
| 62 | Dibenzofuran-2-yl-(4-methyl-benzyl)-amine |
| 63 | Benzyl-dibenzofuran-2-yl-amine |
| 64 | (3-Benzyloxy-benzyl)-dibenzofuran-2-yl-amine |
| 65 | (1-Benzyl-butyl)-dibenzofuran-2-yl-amine |
| 66 | Dibenzofuran-2-yl-8 2-(2-methoxy-phenyl)-1-methyl-ethyl]-amine |
| 67 | 3-(Dibenzofuran-2-ylamino)-2-methyl-butan-1-ol |
| 68 | Dibenzofuran-2-yl-(1-ethyl-butyl)-amine |
| 69 | Dibenzofuran-2-yl-(1-ethyl-propyl)-amine |
| 70 | Dibenzofuran-2-yl-(1,3-dimethyl-butyl)-amine |
| 71 | (1-Cyclohexyl-ethyl)-dibenzofuran-2-yl-amine |
| 72 | Cyclooctyl-dibenzofuran-2-yl-amine |
| 73 | Cycloheptyl-dibenzofuran-2-yl-amine |
| 74 | Dibenzofuran-2-yl-(tetrahydro-thiopyran-4-yl)-amine |
| 75 | Dibenzofuran-2-yl-(tetrahydro-thiophen-3-yl)-amine |
| 76 | Dibenzofuran-2-yl-(1,2-dimethyl-propyl)-amine |
| 77 | Dibenzofuran-2-yl-(1-methyl-butyl)-amine |
| 78 | sec-Butyl-dibenzofuran-2-yl-amine |
| 79 | Benzofurp[3,2-b]pyridin-8-yl-(2-fluoro-benzyl)-amine |
| 80 | Benzofuro[3,3-b]pyridin-8-yl-pyridin-4-ylmethyl-amine |
| 81 | Benzofuro[3,2-b]pyridin-8-yl-(2-methyl-benzyl)-amine |
| 82 | N-(2-Fluoro-benzyl)-N'-methyl-dibenzofuran-2,8-diamine |
| 83 | N-Methyl-N'-quinolin-4-ylmethyl-dibenzofuran-2,8-diamine |
| 84 | N-Methyl-N'-naphthanlen-1-ylmethyl-dibenzofuran-2,8-diamine |
| 85 | N-(4-Methanesulfonyl-benzyl)-N'-methyl-dibenzofuran-2,8-diamine |
| 86 | N-Methyl-N'-pyridin-4-ylmethyl-dibensofuran-2,8-diamine |
| 87 | N-Methyl-N'-(2-methyl-benzyl)-dibenzofuran-2,8-diamine |
| 88 | Naphthanlen-1-ylmethyl-(10H-phenothiazin-2-yl)-amine |
| 89 | (4-Methanesulfonyl-benzyl)-(10H-phenothiazin-2-yl)-amine |
| 90 | (3-Fluoro-2-methyl-benzyl)-(10-oxa-9-thia-1-aza-anthracen-6-yl)-amine |
| 91 | (2-Fluoro-2-methyl-benzyl)-(10-oxa-9-thia-1-aza-anthracen-6-yl)-amine |
| 92 | (10-Oxa-9-thia-1-aza-anthracen-6-yl)-qinolin-4-ylmethyl-amine |
| 93 | Naphthalene-1-ylmethyl-(10-oxa-9-thia-1-aza-anthracen-6-yl)-amine |
| 94 | (4-Methanesulfonyl-benzyl)-(10-oxa-9-thia-1-aza-anthracen-6-yl)-amine |
| 95 | (10-Oxa-9-thia-1-aza-anthracen-6-yl)-pyridin-4-ylmethyl-amine |
| 96 | (2-Methyl-benzyl)-(10-oxa-9-thia-1-aza-anthracen-4-yl)-amine |
| 97 | Anthracen-2-yl-quinolin-4-ylmethyl-amine |
| 98 | Anthracen-2-yl-(4-methanesulfonyl-benzyl)-amine |
| 99 | Anthracen-2-yl-pyridin-4-ylmethyl-amine |
| 100 | Anthracen-2-yl-(2-methyl-benzyl)-amine |
| 101 | Dibenzo[b,e][1,4]-dioxin-2-yl-(2-fluoro-benzyl)-amine |
| 102 | Dibenzo[b,e][1,4]dioxin-2-yl-(2-fluoro-benzyl)-amine |
| 103 | Dibenzo[b,e][1,4]fioxin-2-yl-quinolin-4-ylmethyl-amine |
| 104 | Dibenzo[b,e][1,4]fioxin 2-yl-naphthalen-1-ylmethyl-amine |
| 105 | Dibenzo[b,e][1,4]fioxin 2-yl-(4-methanesulfonyl-benzyl)-amine |
| 106 | Dibenzo[b,e][1,4]fioxin 2-yl-pyridin-4-ylmethyl-amine |
| 107 | 8-(3-Fluoro-2-methyl-benzylamino)-dibenzofuran-2-ol |
| 108 | 8-(2-Fluoro-benzylamino)-dibenzofuran2-ol |
| 109 | 8-(4-Methanesulfonyl-benzylamino)-dibenzofuran-2-ol |
| 110 | 8-[(Pyridin-4-ylmethyl)-amino]-dibenzofuran-2-ol |
| 111 | 8-(2-Methyl-benzylamino)-dibenzofuran-2-ol |
| 112 | (8-Chloro-dibenzofuran-2-yl)-(2-fluoro-benzyl)-amine |
| 113 | 8-Chloro-dibenzofuran-2-yl)-naphthalen-1-ylmethyl-amine |
| 114 | 8-Chloro-dibenzofuran-2-yl)-(4-methanesulfonyl-benzyl)-amine |

-continued

| | |
|---|---|
| 115 | (4-methanesulfonyl-benzyl)-(6,7,8,9-tetrahydro-5H-carbazol-3-yl)-amine |
| 116 | Pyridin-4-ylmethyl-(6,7,8,9-tetrahydro-SH-carbazol-3-yl)-amine |
| 117 | Benzofuro[3,2-b]pyridin-8-yl-(3-fluoro-2-methyl-benzyl)-amine |
| 118 | Dibenzofuran-2-yl-quinolin-4-ylmethyl-amine |
| 119 | Dibenzofuran-2-yl-quinolin-2-ylmethyl-amine |
| 120 | (4-Dimethylamino-benzyl)-(8-fluoro-dibenzofuran-2-yl)-amine |
| 121 | Dibenzofuran-2-yl-(4-dimethylamino-benzyl)-amine |
| 122 | Dibenzofuran-2-yl-(5-nitro-thiophen-2-ylmethyl)-amine |
| 123 | Dibenzofuran-2-yl-thiazol-2-ylmethyl-amine |
| 124 | Benzyl-(8-fluoro-dibenzofuran-2-yl)-amine |
| 125 | N-(-3-Methoxybenzyl)-N'-methyl-dibenzofuran-2,8-diamine |
| 126 | N-(3,5-Dimethoxy-benzyl)-N'-methyl-dibenzofuran-2,8-diamine |
| 127 | N-(4-tert-Butyl-benzyl)-N'-methyl-dibenzofuran-2,8-diamine |
| 128 | N-Benzyl-N'-methyl-dibenzofuran-2,8-diamine |
| 129 | 2-[(8-Methylamino-dibenzofuran-2-ylamino)-methyl]-benzonitrile |
| 130 | (4-Methoxy-benzyl)-phenoxathiin-3-yl-amine |
| 131 | (8-Chloro-dibenzofuran-2-yl)-(3-methoxy-benzyl)-amine |
| 132 | (3-Methoxy-benzyl)-phenoxathiin-3-yl-amine |
| 133 | (3,5-Dimethoxy-benzyl)-phenoxathiin-3-yl-amine |
| 134 | (3-Fluoro-4-methoxy-benzyl)-phenoxathiin-3-yl-amine |
| 135 | (4-tert-Butyl-benzyl)-phenoxathiin-3-yl-amine |
| 136 | Benzyl-phenoxathiin-3-yl-amine |
| 137 | (2-Ethoxy-benzyl)-phenoxathiin-3-yl-amine |
| 138 | (8-Chloro-dibenzofuran-2-yl)-(3,5-dimethoxy-benzyl)-amine |
| 139 | (8-Chloro-dibenzofuran-2-yl)-(3-fluoro-4-methoxy-benzyl)-amine |
| 140 | Benzyl-(8-chloro-dibenzofuran-2-yl)-amine |
| 141 | (9H-Fluoren-2-yl)-(4-methoxy-benzyl)-amine |
| 142 | (8-Chloro-dibenzofuran-2-yl)-thiazol-2-ylmethyl-amine |
| 143 | (9H-Fluoren-2-yl)-(3-methoxy-benzyl)-amine |
| 144 | (3,5-Dimethoxy-benzyl)-(9H-fluoren-2-yl)-amine |
| 145 | (9H-Fluoren-2-yl)-(3-fluoro-4-methoxy-benzyl)-amine |
| 146 | (4-tert-Butyl-benzyl)-(9H-fluoren-2-yl)-amine |
| 147 | Benzyl-(9H-fluoren-2-yl)-amine |
| 148 | (9H-Fluoren-2-yl)-thiazol-2-ylmethyl-amine |
| 149 | (2-Ethoxy-benzyl)-(9H-fluoren2-yl)-amine |
| 150 | Dibenzofuran-4-yl-(4-methoxy-benzyl)-amine |
| 151 | 2-[(8-Chloro-dibenzofuran-2-ylamino)-methyl]-benzonitrile |
| 152 | Dibenzofuran-4-yl-(3-methoxy-benzyl)-amine |
| 153 | Dibenzofuran-4-yl-(3,5-dimethoxy-benzyl)-amine |
| 154 | Dibenzofuran-4-yl-(3-fluoro-4-methoxy-benzyl)-amine |
| 155 | (4-tert-Butyl-benzyl)-dibenzofuran-4-yl-amine |
| 156 | Dibenzofuran-4-yl-(2-ethoxy-benzyl)-amine |
| 157 | N-(4-Methoxy-benzyl)-N'-methyl-dibenzofuran-2,8-diamine |
| 158 | (8-Chloro-dibenzofuran-2-yl)(4-methoxy-benzyl)-amine |
| 159 | (8-Chloro-dibenzofuran-2-yl)-(2-ethoxy-benzyl)-amine |
| 160 | Dibenzofuran-4-yl-(2,4-dimethyl-benzyl)-amine |
| 161 | N-Methyl-N'-thiophen-3-ylmethyl-dibenzofuran-2,8-diamine |
| 162 | N-Methyl-N'-pyridin-2-ylmethyl-dibenzofuran-2,8-diamine |
| 163 | (2-Bromo-benzyl)-phenoxathiin-3-yl-amine |
| 164 | Phenoxathiin-3-yl-quiolin-4-ylmethyl-amine |
| 165 | Phenoxathiin-3-yl-thiophen-3-ylmethyl-amine |
| 166 | (3-Methyl-pyridin-2-ylmethyl)-phenoxathiin-3-yl-amine |
| 167 | Phenoxathiin-3-yl-pyridin-3-ylmethyl-amine |
| 168 | Phenoxathiin-3-yl-pyridin-2-ylmethyl-amine |
| 169 | (8-Chloro-dibenzofuran-2-yl)-thiophen-3-ylmethyl-amine |
| 170 | (2-Bromo-benzyl)-(9-ethyl-9H-carbazol-3-yl)-amine |
| 171 | (8-Chloro-dibenzofuran-2-yl)-(3-methyl-pyridin-2-ylmethyl)-amine |
| 172 | (9-Ethyl-9H-carbazol-3-yl)-thiophen-3-ylmethyl-amine |
| 173 | (5-Chloro-thiophen-2-ylmethyl)-(9-ethyl-9H-carbozol-3-yl)-amine |
| 174 | (9-Ethyl-9H-carbazol-3-yl)-pyridin-3-ylmethyl-amine |
| 175 | (2-Bromo-benzyl)-(9H-fluoren-2-yl)-amine |
| 176 | (8-Chloro-dibenzofuran-2-yl)-pyridin-4-ylmethyl-amine |
| 177 | (9H-Fluoren 2-yl)-quinolin-2-ylmethyl-amine |
| 178 | (9H-Fluoren-2-yl)-thiophen-3-ylmethyl-amine |
| 179 | (9H-Fluoren-2-yl)-(3-methyl-pyridin-2 ylmethyl)-amine |
| 180 | (9H-Fluoren-2-yl)-pyridin-4-ylmethyl-amine |
| 181 | (9H-Fluoren-2-yl)-pyridin-3-ylmethyl-amine |
| 182 | (9H-Fluoren-2-yl)-pyridin-2-ylmethyl-amine |
| 183 | (8-Chloro-dibenzofuran-2-yl)-pyridin-3-ylmethyl-amine |
| 184 | Dibenzofuran-4-yl-quinolin-4-ylmethyl-amine |
| 185 | Dibenzofuran-4-yl-quinolin-2-ylmethyl-amine |
| 186 | Dibenzofuran-4-yl-thiophen-3-ylmethyl-amine |
| 187 | Dibenzofuran-4-yl-(3-methyl-pyridin-2-ylmethyl)-amine |
| 188 | Dibenzofuran-4-yl-pyridin-4-ylmethyl-amine |
| 189 | Dibenzofuran-4-yl-pyridin-3-ylmethyl-amine |
| 190 | Dibenzofuran-4-yl-pyridin-2-ylmethyl-amine |
| 191 | (2-Bromo-benzyl)-(8-chloro-dibenzofuran-2-yl)-amine |
| 192 | (8-Chloro-dibenzofuran-2-yl)-pyridin-2-ylmethyl-amine |
| 193 | N-Methyl-N'-(2,3,6-trifluro-benzyl)-dibenzofuran-2,8-diamine |

-continued

| | |
|---|---|
| 194 | N-Methyl-N'-(2,3,4-trifluro-benzyl)-dibenzofuran-2,8-diamine |
| 195 | N-(2,6-Difluoro-benzyl)-N'-methyl-dibenzofuran-2,8-diamine |
| 196 | N-(2,5-Difluoro-benzyl)-N'-methyl-dibenzofuran-2,8-diamine |
| 197 | N-(2,4-Difluoro-benzyl)-N'-methyl-dibenzofuran-2,8-diamine |
| 198 | N-(2,3-Difluoro-benzyl)-N'-methyl-dibenzofuran-2,8-diamine |
| 199 | N-(2,5-Dimethyl-benzyl)-N'-methyl-dibenzofuran-2,8-diamine |
| 200 | N-(2,4-Dimethyl-benzyl)-N'-methyl-dibenzofuran-2,8-diamine |
| 201 | N-(2,3-Dihydro-benzo[1,4]dioxin-6-ylmethyl)-N'-methyl-dibenzofuran-2,8-diamne |
| 202 | (3-Fluoro-2-methyl-benzyl)-phenoxathiin-3-yl-amine |
| 203 | (8-Chloro-dibenzofuran-2-yl)-(2,3,6-trifluoro-benzyl)-amine |
| 204 | Phenoxathiin-3-yl-(2,3,6-trifluoro-benzyl)-amine |
| 205 | Phenoxathiin-3-yl-(2,3,4-trifluoro-benzyl)-amine |
| 206 | (2,6-Difluoro-benzyl)-phenoxathiin-3-yl-amine |
| 207 | (2,5-Difluoro-benzyl)-phenoxathiin-3-yl-amine |
| 208 | (2,4-Difluoro-benzyl)-phenoxathiin-3-yl-amine |
| 209 | (2,3-Difluoro-benzyl)-phenoxathiin-3-yl amine |
| 210 | (2,4-Dimethyl-benzyl)-phenoxathiin-3-yl-amine |
| 211 | (2,3-Dihydro-benzo[1,4]dioxin-6-ylmethyl)-phenoxathiin-3-yl-amine |
| 212 | Benzo[b]thiophen 5-yl-(3-fluoro-2-methyl-benzyl)-amine |
| 213 | (8-Chloro-dibenzofuran-2-yl)-(2,3,4-trifluoro-benzyl)-amine |
| 214 | (8-Chloro-dibenzofuran-2 yl)-(2,6-difluoro-benzyl)-amine |
| 215 | (8-Chloro-dibenzofuran-2-yl)-(2,5-difluoro-benzyl)-amine |
| 216 | (8-Chloro-dibenzofuran-2-yl)-(2,4-difluoro-benzyl)-amine |
| 217 | (9-Ethyl-9H-carbazol-3-yl)-(3-fluoro-2-methyl-benzyl)-amine |
| 218 | (8-Chloro-dibenzofiram-2-yl)-(2,3-difluoro-benzyl)-amine |
| 219 | (9-Ethyl-9H-carbazol-3-yl)-(2,3,6-trifluoro-benzyl)-amine |
| 220 | (9-Ethyl-9H-carbazol-3-yl)-(2,3,4-trifluoro-benzyl)-amine |
| 221 | (2,6-Difluoro-benzyl)-(9-ethyl-9H-carbazol-3-yl)-amine |
| 222 | (2,5-Difluoro-benzyl)-(9-ethyl-9H-carbazol-3-yl)-amine |
| 223 | (2,4-Difluoro-benzyl)-(9-ethyl-9H-carbazol-3-yl)-amine |
| 224 | (2,3-Difluoro-benzyl)-(9-ethyl-9H-carbazol-3-yl)-amine |
| 225 | (2,5-Dimethyl-benzyl)-(9-ethyl-9H-carbazol-3-yl)-amine |
| 226 | (2,4-Dimethyl-benzyl)-(9-ethyl-9H-carbazol-3-yl)-amine |
| 227 | (2,3-Dihydro-benzo[1,4]dioxin-6-ylmethyl)-(9-ethyl-9H-carbazol-3-yl)-amine |
| 228 | (9H-Fluoren-2-yl)-(3-fluoro-2-methyl-benzyl-amine |
| 229 | (8-Chloro-dibenzofuran-2-yl)-(2,5-dimethyl-benzyl)-amine |
| 230 | (9H-Fluoren-2-yl)-(2,3,6-trifluoro-benzyl)-amine |
| 231 | (9H-Fluoren-2-yl)-(2,3,4-trifluoro-benzyl)-amine |
| 232 | (2,5-Difluoro-benzyl)-(9H-fluoren-2-yl)-amine |
| 233 | (2,4-Difluoro-benzyl)-(9H-fluoren-2-yl)-amine |
| 234 | (2,3-Difluoro-benzyl)-(9H-fluoren-2-yl)-amine |
| 235 | (2,5-Dimethyl-benzyl)-(9H-fluoren-2-yl)-amine |
| 236 | (2,4-Dimethyl-benzyl)-(9H-fluoren-2 yl)-amine |
| 237 | (2,3-Dihydro-benzo[1,4]dioxin-6-ylmethyl)-(9H-fluroen-2-yl)-amine |
| 238 | (8-Chloro-dibenzofuran-2-yl)-(2,4-dimethyl-benzyl)-amine |
| 239 | Dibenzofuran-4-yl-(2,5-dimethyl-benzyl)-amine |
| 240 | Dibenzofuran-4-yl-(3-fluoro-2-methyl-benzyl)-amine |
| 241 | N-(3-Fluoro-2-methyl-benzyl)-N'-methyl-dibenzofuran-2,8-diamine |
| 242 | (8-Chloro-dibenzofuran-2-yl)-(3-fluoro-2-methyl-benzyl)-amine |
| 243 | (8-Chloro-dibenzofuran-2-yl)-(2,3-dihydro-benzo[1,4]dioxin-6-ylmethyl)-amine |
| 244 | (2,5-Dimethoxy-benzyl)-phenoxathiin-3-yl-amine |
| 245 | (2,3-Dimethoxy-benzyl)-phenoxathiin-3-yl-amine |
| 246 | (2-Chloro-benzyl)-phenoxathiin-3-yl-amine |
| 247 | (2-Methoxy-benzyl)-phenoxathiin-3-yl-amine |
| 248 | (2-Methyl-benzyl)-phenoxathiin-3-yl-amine |
| 249 | Anthracen-2-yl-(2-chloro-benzyl)-amine |
| 250 | Anthracen-2-yl-(2-fluoro-benzyl)-amine |
| 251 | Dibenzo[1,4]dioxin-2-yl-(2,3-dimethyoxy-benzyl)-amine |
| 252 | (2-Chloro-benzyl)-dibenzo[1,4]dioxin-2-yl-amine |
| 253 | 2-(Dibenzo[1,4]dioxin-2-ylaminomethyl)-phenol |
| 254 | Dibenzo[1,4]dioxin-2-yl-(2-methoxy-benzyl)-amine |
| 255 | 2-[(9-Ethyl-9H-carbazol-3-ylamino)-methyl]-phenol |
| 256 | (9-Ethyl-9H-carbazol-3-yl)-(2-fluoro-benzyl)-amine |
| 257 | (9-Ethyl-9H-carbazol-3-yl)-(2-methyl-benzyl)-amine |
| 258 | (2-Chloro-benzyl)-(9H-fluoren-2-yl)-amine |
| 259 | 2-[(9H-Fluoren-2-ylamino)-methyl]-phenol |
| 260 | (9H-Fluoren-2-yl)-(2-methoxy-benzyl)-amine |
| 261 | (9H-Fluoren-2-yl)-(2-trifluoromethyl-benzyl)-amine |
| 262 | (9H-Fluoren-2-yl)-(2-fluoro-benzyl)-amine |
| 263 | Dibenzofuran-4-yl-(2,5-dimethoxy-benzyl)-amine |
| 264 | Dibenzofuran-4-yl-(2,3-dimethoxy-benzyl)-amine |
| 265 | 2-(Dibenzofuran-4-ylaminomethyl)-phenol |
| 266 | Dibenzofuran-4-yl-(2-methoxy-benzyl)-amine |
| 267 | (2,5-Dimethoxy-benzyl)-(3-methoxy-dibenzofuran-2-yl)-amine |
| 268 | (2,3-Dimethoxy-benzyl)-(3-methoxy-dibenzofuran-2-yl)-amine |
| 269 | (2-Methoxy-benzyl)-(3-methoxy-dibenzofuran-2-yl)-amine |
| 270 | Dibenzofuran-2-yl-(2,5-dimethoxy-benzyl)-amine |
| 271 | Dibenzofuran-2-yl-(4-methoxy-benzyl)-amine |

-continued

| | |
|---|---|
| 272 | (2-Bromo-benzyl)-dibenzofuran-2-yl-amine |
| 273 | (8-Fluoro-dibenzofuran-2-yl)-(3H-imidazol-4-ylmethyl)-amine |
| 274 | 2-[(8-Fluoro-dibenzofuran-2-ylamino)-methyl]-benzonitrile |
| 275 | (2-Ethoxy-benzyl)-(8-fluoro-dibenzofuran-2-yl)-amine |
| 276 | (8-Fluoro-dibenzofuran-2-yl)-(4-methylsulfanyl-benzyl)-amine |
| 277 | (2-Bromo-benzyl)-(8-fluoro-dibenzofuran-2-yl)-amine |
| 278 | (8-Fluoro-dibenzofuran-2-yl)-quinolin-4-ylmethyl-amine |
| 279 | (8-Fluoro-dibenzofuran-2-yl)-quinolin-2-ylmethyl-amine |
| 280 | Dibenzofuran-2-yl-naphthalen-1-ylmethyl-amine |
| 281 | (8-Fluoro-dibenzofuran-2-yl)-naphthalen-2-ylmethyl-amine |
| 282 | (8-Fluoro-dibenzofuran-2-yl)-naphthalen-1-ylmethyl-amine |
| 283 | Dibenzofuran-2-yl-(2-nitro-benzyl)-amine |
| 284 | Dibenzofuran-2-yl-(3H-imidazol-4-ylmethyl)-amine |
| 285 | 2-(Dibenzofuran-2-ylaminomethyl)-benzonitrile |
| 286 | Dibenzofuran-2-yl-(2-ethoxy-benzyl)-amine |
| 287 | Dibenzofuran-2-yl-(3-trifluoromethyl-benzyl)-amine |
| 288 | (4-tert-Butyl-benzyl)-dibenzofuran-2-yl-amine |
| 289 | Dibenzofuran-2-yl-(3-fluoro-benzyl)-amine |
| 290 | (2,5-Dimethoxy-benzyl)-(8-fluoro-dibenzofuran-2-yl)-amine |
| 291 | (2,3-Dimethoxy-benzyl)-(8 fluoro-dibenzofuran-2-yl)-amine |
| 292 | (4-Benzyloxy-benzyl)-(8-fluoro-dibenzofuran-2-yl)-amine |
| 293 | (3-Benzyloxy-benzyl)-(8-fluoro-dibenzofuran-2-yl)-amine |
| 294 | (4-Chloro-benzyl)-(8-fluoro-dibenzofuran-2-yl)-amine |
| 295 | (3-Chloro-benzyl)-(8-fluoro-dibenzofuran-2-yl)-amine |
| 296 | (2-Chloro-benzyl)-(8-fluoro-dibenzofuran 2-yl)-amine |
| 297 | 4-[(8-Fluoro-dibenzofuran-2-ylamino)-methyl]-phenol |
| 298 | 3-[(8-Fluoro-dibenzofuran-2-ylamino)-methyl]-phenol |
| 299 | Dibenzofuran-2-yl-(2-fluoro-benzyl)-amine |
| 300 | (8-Fluoro-dibenzofuran-2-yl)-(4-methoxy-benzyl)-amine |
| 301 | (8-Fluoro-dibenzofuran-2-yl)-(3-methoxy-benzyl)-amine |
| 302 | (8-Fluoro-dibenzofuran-2-yl)-(2-methoxy-benzyl)-amine |
| 303 | (8-Fluoro-dibenzofuran-2-yl)-(4-trifluoromethyl-benzyl)-amine |
| 304 | (8-Fluoro-dibenzofuran-2-yl)-(3-trifluoromethyl-benzyl)-amine |
| 305 | (4-tert-Butyl-benzyl)-(8-fluoro-dibenzofuran-2-yl)-amine |
| 306 | (4-Fluoro-benzyl)-(8-fluoro-dibenzofuran-2-yl)-amine |
| 307 | (3-Fluoro-benzyl)-(8-fluoro-dibenzofuran-2-yl)-amine |
| 308 | (2-Fluoro-benzyl)-(8-fluoro-dibenzofuran-2-yl)-amine |
| 309 | (8-Fluoro-dibenzofuran-2-yl)-(4-methyl-benzyl)-amine |
| 310 | (8-Fluoro-dibenzofuran-2-yl)-(3-methyl-benzyl)-amine |
| 311 | Dibenzofuran-2-yl-(2,6-dimethoxy-benzyl)-amine |
| 312 | Dibenzofuran-2-yl-(2,4-dimethoxy-benzyl)-amine |
| 313 | Dibenzofuran-2-yl-(2,3-dimethoxy-benzyl)-amine |
| 314 | (4-Benzyloxy-benzyl)-dibenzofuran-2-yl-amine |
| 315 | Dibenzofuran-2-yl-(3-methyl-benzyl)-amine |
| 316 | (3-Chloro-benzyl)-dibenzofuran-2-yl-amine |
| 317 | 3-(Dibenzofuran-2-ylaminomethyl)-phenol |
| 318 | (2-Chloro-benzyl)dibenzofuran-2-yl-amine |
| 319 | Dibenzofuran-2-yl-(3-methoxy-benzyl)-amine |
| 320 | Dibenzofuran-2-yl-(2-methoxy-benzyl)-amine |
| 321 | (9H-Fluoren-2-yl)-(2-methyl-benzyl)-amine |
| 322 | Dibenzofuran-4-yl-(2-methyl-benzyl)-amine |
| 323 | (6-Chloro-dibenzofuran-2-yl)-(2-methyl-benzyl)-amine |
| 324 | (2-Methyl-benzyl)-(10H-phenothiazin-2-yl)-amine |
| 325 | Dibenzo[b,e][1,4]dioxin-2-yl-(2-methyl-benzyl)-amine |
| 326 | Dibenzofuran-2-yl-(2,6-difluoro-benzyl)-amine |
| 327 | Dibenzofuran-2-yl-(2,5-difluoro-benzyl)-amine |
| 328 | Dibenzofuran-2-yl-(2,4-difluoro-benzyl)-amine |
| 329 | Dibenzofuran-2-yl-(2,3-difluoro-benzyl)-amine |
| 330 | (8-Fluoro-dibenzofuran-2-yl)-thiophen-2-ylmethyl-amine |
| 331 | Dibenzofuran-2-yl-(2,5-dimethyl-benzyl)-amine |
| 332 | (8-Fluoro-dibenzofuran-2-yl)-thiophen-3-ylmethyl-amine |
| 333 | (8-Fluoro-dibenzofuran-2-yl)-furan-2-ylmethyl-amine |
| 334 | (8-Fluoro-dibenzofuran-2-yl)-furan-3-ylmethyl-amine |
| 335 | (8-Fluoro-dibenzofuran-2-yl)-(6-methyl-pyridin-2-ylmethyl)-amine |
| 336 | (8-Fluoro-dibenzofuran-2-yl)-(4-methanesulfonyl-benzyl)-amine |
| 337 | (8-Fluoro-dibenzofuran-2-yl)-pyridin-4-ylmethyl-amine |
| 338 | (8-Fluoro-dibenzofuran-2-yl)-pyridin-3-ylmethyl-amine |
| 339 | (8-Fluoro-dibenzofuran-2-yl)-pyridin-2-ylmethyl-amine |
| 340 | (8-Fluoro-dibenzofuran-2-yl)-(3-fluoro-4-methoxy-benzyl)-amine |
| 341 | Dibenzofuran-2-yl-(2,4-dimethyl-benzyl)-amine |
| 342 | (8-Fluoro-dibenzofuran-2-yl)-(3-fluoro-2-methyl-benzyl)-amine |
| 343 | (8-Fluoro-dibenzofuran-2-yl)-(2,3,6-trifluoro-benzyl)-amine |
| 344 | (8-Fluoro-dibenzofuran-2-yl)-(2,3,4-trifluoro-benzyl)-amine |
| 345 | (3,5-Difluoro-benzyl)-(8-fluoro-dibenzofuran-2-yl)-amine |
| 346 | (3,4-Difluoro-benzyl)-(8-fluoro-dibenzofuran-2-yl)-amine |
| 347 | (3,5-difluoro-benzyl)-(8-fluoro-dibenzofuran-2-yl)-amine |
| 348 | (2,6-Difluoro-benzyl (2,5-Difluoro-benzyl)-(8-fluoro-dibenzofuran-2-yl)-amine |
| 349 | (2,4-Difluoro-benzyl)-(8-fluoro-dibenzofuran-2-yl)-amine |
| 350 | (2,3 Difluoro-benzyl)-(8-fluoro-dibenzofiran 2-yl) r,ine |

-continued

| | |
|---|---|
| 351 | (2,5-Dimethyl benzyl)-(8-fluoro-dibenzofuran-2-yl)-amine |
| 352 | (2,4-Dimethyl benzyl)-(8-fluoro-dibenzofuran-2-yl)-amine |
| 353 | (2,3-Dihydro-1,4-benzodioxin-6-ylmethyl)-(8-fluoro-dibenzofuran-2-yl)-amine |
| 354 | (3,5-Dimethoxy-benzyl)-(8-fluoro-dibenzofuran-2-yl)-amine |
| 355 | Dibenzofuran-2-yl-furan-2-ylmethyl-amine |
| 356 | Dibenzofuran-2-yl-furan-3-ylmethyl-amine |
| 357 | Dibenzofuran-2-yl-(6-methyl-pyridin-2-ylmethyl)-amine |
| 358 | Dibenzofuran-2-yl-(4-methanesulfonyl-benzyl)-amine |
| 359 | Dibenzofuran-2-yl-pyridin-4-ylmethyl-amine |
| 360 | Dibenzofuran-2-yl-pyridin-3-ylmethyl-amine |
| 361 | Dibenzofuran-2-yl pyridin-2-ylmethyl-amine |
| 362 | Dibenzofuran-2-yl-(3-fluoro-4-methoxy-benzyl)-amine |
| 363 | Dibenzofuran-2-yl-(3-fluoro-2-methyl-benzy)-amine |
| 364 | Dibenzofuran-2-yl-(2,3,6-trifluoro-benzyl)-amine |
| 365 | Dibenzofuran-2-yl-(2,3,4-trifluoro-benzyl)-amine |
| 366 | Dibenzofuran-2-yl-(3,5-difluoro-benzyl)-amine |
| 367 | Dibenzofuran-2-yl-(3,4-difluoro-benzyl)-amine |
| 368 | Dibenzofuran-2-yl-(3,4-dimethoxy-benzyl)-amine |
| 369 | Dibenzofuran-2-yl-methyl-(2-methyl-benzyl)-amine |
| 370 | Dibenzothiohen-2-yl-(2,4-dimethyl-benzyl)-amine |
| 371 | (4-tert-Butyl-benzyl)-dibenzothiohen-2-yl-amine |
| 372 | (2-Chloro-benzyl)-dibenzothiohen-2-yl-amine |
| 373 | Dibenzothiohen-2-yl-(2,6-difluoro-benzyl)-amine |
| 374 | Dibenzothiohen-2-yl-(2,3,6-trifluoro-benzyl)-amine |
| 375 | Dibenzothiohen-2-yl-(2-fluoro-benzyl)-amine |
| 376 | Benzyl-dibenzothiohen-2-yl-amine |
| 377 | Dibenzothiohen-2-yl-(4-methoxy-benzyl)-amine |
| 378 | Dibenzothiohen-2-yl-(2,3-dimethoxy-benzyl)-amine |
| 379 | Dibenzothiohen-2-yl-(2,5-difluoro-benzyl)-amine |
| 380 | Dibenzothiohen-2-yl-(3-methoxy-benzyl)-amine |
| 381 | Dibenzothiohen-2-yl-(2,3,4-trifluoro-benzyl)-amine |
| 382 | (-2-Bromo-benzyl)-dibenzothiohen-2-yl-amine |
| 383 | Dibenzothiohen-2-yl-(2,3-dihydro-1,4-benzodioxin-6-ylmethyl)-amine |
| 384 | Dibenzothiohen-2-yl-(3-fluoro-4-methoxy-benzyl)-amine |
| 385 | Dibenzothiohen-2-yl-(2,5-dimethyl-benzyl)-amine |
| 386 | Dibenzothiohen-2-yl-thiophen-3-ylmethyl-amine |
| 387 | Dibenzothiohen-2-yl-naphthalene-1-ylmethyl-amine |
| 388 | Dibenzothiohen-2-yl-(2-trifluoromethyl-benzyl)-amine |
| 389 | Dibenzothiohen-2-yl-naphthalen-2-ylmethyl-amine |
| 390 | Dibenzothiohen-2-yl-(2-ethoxy-benzyl)-amine |
| 391 | (10,11-Dihydro-5H-dibenz[b,f]azepin-2-yl)-(3-fluoro-2-methyl-benzyl)-amine |
| 392 | (10,11-Dihydro-5H-dibenz[b,f]azepin-2-yl)-(2-methyl-benzyl)-amine |
| 393 | (10,11-Dihydro-5H-dibenz[b,f]azepin-2-yl)-(2,4-dimethyl-benzyl)-amine |
| 394 | (4-tert-Butyl-benzyl)-(10,11-dihydro-5H-dibenz[b,f]azepin-2-yl)-amine |
| 395 | (2-Chloro-benzyl)-(10,11-dihydro-5H-dibenz[b,f]azepin-2-yl)-amine |
| 396 | (2,6-Difluoro-benzyl)-(10,11-dihydro-5H-dibenz[b,f]azepin-2-yl)-amine |
| 397 | (10,11-Dihydro-5H-dibenz[b,f]azepin-2-yl)-(2,3,6-trifluoro-benzyl)-amine |
| 398 | (10,11-Dihydro-5H-dibenz[b,f]azepin-2-yl)-(2-fluoro-benzyl)-amine |
| 399 | (10,11-Dihydro-5H-dibenz[b,f]azepin-2-yl)-(3,5-dimethoxy-benzyl)-amine |
| 400 | Benzyl-(10,11-dihydro-5H-dibenz[b,f]azepin-2-yl)-amine |
| 401 | (10,11-Dihydro-5H-dibenz[b,f]azepin-2-yl)-(4-methoxy-benzyl)-amine |
| 402 | (10,11-Dihydro-5H-dibenz[b,f]azepin-2-yl)-(2,3-dimethoxy-benzyl)-amine |
| 403 | (2,5-difluoro-benzyl)-10,11-dihydro-5H-dibenz[b,f]azepin-2-yl)-amine |
| 404 | (10,11-Dihydro-5H-dibenz[b,f]azepin-2-yl)-(3-methoxy-benzyl)-amine |
| 405 | (10,11-Dihydro-5H-dibenz[b,f]azepin-2-yl)-(2,3,4-trifluoro-benzyl)-amine |
| 406 | (2-Bromo-benzyl)-(10,11-dihydro-5H-dibenz[b,f]azepin-2-yl)-amine |
| 407 | (2,3-Diydro-1,4-benzodioxin-6-ylmethyl)-(10,11-dihydro-5H-dibenz[b,f]azepin-2-yl)-amine |
| 408 | (10,11-Dihydro-5H-dibenz[b,f]azepin-2-yl)-(3-fluoro-4-methoxy-benzyl)-amine |
| 409 | (10,11-Dihydro-5H-dibenz[b,f]azepin-2-yl)-(2,5 dimethyl-benzyl)-amine |
| 410 | (10,11-Dihydro-5H-dibenz[b,f]azepin-2-yl)-thiophen-3-ylmethyl-amine |
| 411 | (10,11 -Dihydro-5H-dibenz[b,f]azepin-2-yl)-naphthalen-1-ylmethyl-amine |
| 412 | (10,11-Dihydro-5H-dibenz[b,f]azepin-2-yl)-(2-trifluoromethyl-benzyl)-amine |
| 413 | (10,11-Dihydro-5H-dibenz[b,f]azepin-2-yl)-naphthalen-2-ylmethyl-amine |
| 414 | (10,11-Dihydro-5H-dibenz[b,f]azepin-2-yl)-(2 ethoxy-benzyl)-amine |
| 415 | (3-Fluoro-2-methyl-benzyl)-(10H-phenothiazin-2-yl)-amine |
| 416 | (2,4-Dimethyl-benzyl)-(10H-phenothiazin-2-yl)-amine |
| 417 | (4-tert-Butyl-benzyl)-(10H-phenothiazin-2-yl)-amine |
| 418 | (2-Chloro-benzyl)-(10H-phenothiazin-2-yl)-amine |
| 419 | (2,6-Difluoro-benzyl)-(10H-phenothiazin-2-yl)-amine |
| 420 | (10H-Phenothiazin-2-yl)-(2,3,6-trifluorobenzyl)-amine |
| 421 | (2-Fluoro-benzyl)-(10H-phenothiazin-2-yl)-amine |
| 422 | (3,S-Dimethoxy-benzyl)-(10H-phenothiazin-2-yl)-amine |
| 423 | Benzyl-(10H-phenothiazin-2-yl)-amine |
| 424 | (4-Methoxy-benzyl)-(10H-phenothiazin-2-yl)-amine |
| 425 | (2,5-Difluoro-benzyl)-(10H-phenothiazin-2-yl)-amine |
| 426 | (10H-Phenothiazin-2-yl)-(2,3,4-trifluoro-benzyl)-amine |
| 427 | (2,3-Diydro-1,4-benzodioxin-6-ylmethyl)-(10H-phenothiazin-2-yl)-amine |
| 428 | (3-Fluoro-4-methoxy-benzyl)-(10H-phenothiazin-2-yl)-amine |

-continued

| | |
|---|---|
| 429 | (2,5-Dimethyl-benzyl)-(10H-phenothiazin-2-yl)-amine |
| 430 | (10H-Phenothiazin-2-yl)-thiophen-3-ylmethyl-amine |
| 431 | (10H-Phenothiazin-2-yl)-(2-trifluoromethyl-benzyl)-amine |
| 432 | (9H-Carbazol-3-yl)-(3-fluoro-2-methyl-benzyl)-amine |
| 433 | (9H Carbazol-3-yl)-(2-methyl-benzyl)-amine |
| 434 | (9H-Carbazol-3-yl)-(2,4-methyl-benzyl)-amine |
| 435 | (4-tert-Butyl-benzyl)-(9H-carbazol-3-yl)-amine |
| 436 | (9H-Carbazol-3-yl)-(2-chloro-benzyl)-amine |
| 437 | (9H-Carbazol-3-yl)-(2,6-difluoro-benzyl)-amine |
| 438 | (9H-Carbazol-3-yl)-(2,3,6-trifluoro-benzyl)-amine |
| 439 | (9H-Carbazol-3-yl)-(3,5-dimethoxy-benzyl)-amine |
| 440 | (9H-Carbazol-3-yl)-(2,3-dimethoxy-benzyl)-amine |
| 441 | (9H-Carbazol-3-yl)-(2,5 difluoro-benzyl) amine |
| 442 | (9H-Carbazol-3-yl)-(2,3,4-trifluoro-benzyl)-amine |
| 443 | (9H-Carbazol-3-yl)-(2,3 dihydro-1,4-benzodioxin-ylmethyl)-amine |
| 444 | (9H-Carbazol-3-yl)-(2,5-dimethyl-benzyl)-amine |
| 445 | (9H-Carbazol-3-yl)-naphthalen-1-ylmethyl-amine |
| 446 | (9H-Carbazol-3-yl)-naphthalen-2-ylmethyl-amine |
| 447 | Dibenzofuran-2-yl-bis-(2,3-dihydro-benzo[1,4]dioxin-6-ylmethyl-amine |
| 448 | Dibenzofuran-2-yl-bis-thiopen-3-ylmethyl-amine |
| 449 | Dibenzofuran-2-yl-(4-phenoxy-benzyl)-amine |
| 450 | 2-Dibenzofuran,2-yl-2,3-dihydro-1H-isoindole |
| 451 | 2-Dibenzofuran-2-yl-1H-isoindole-1,3-dione |
| 452 | Dibenzofuran-2-yl-(4-trifluoromethoxy-benzyl)-amine |
| 453 | Dibenzofuran-2-yl-(2-methoxy-benzyl)-amine |
| 454 | Dibenzofuran-2-yl-(3-phenoxy-benzyl)-amine |
| 455 | Dibenzofuran-2-yl-methyl(2-methyl-benzyl)-amine |
| 456 | Dibenzofuran-2-yl-(1-phenyl-butyl)-amine |
| 457 | Dibenzofuran-2-yl-phenethyl-amine |
| 458 | Dibenzofuran-2-yl-(1-phenyl-ethyl-amine |

EXAMPLES

| Example | MOLSTRUCTURE | General procedure | M + H (APCI)* | MOLECULAR FORMULA |
|---|---|---|---|---|
| 1 | | 7 | 282 | C18 H19 N O2 |
| 2 | | 7 | 250 | C18 H19 H |
| 3 | | 7 | 250 | C18 H19 N |

-continued
| Example | MOLSTRUCTURE | General procedure | M + H (APCl)* | MOLECULAR FORMULA |
|---|---|---|---|---|
| 4 | 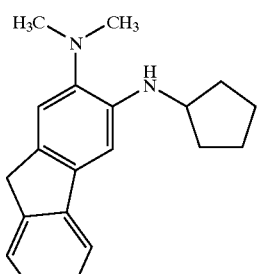 | 7 | 293 | C20 H24 N2 |
| 5 | 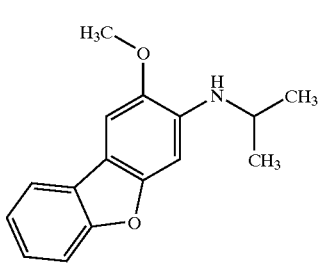 | 5 | 256 | C16 H17 N O2 |
| 6 | 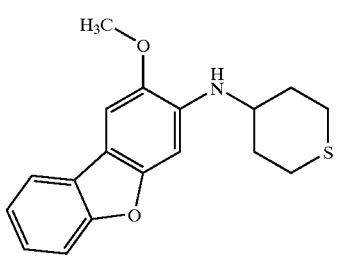 | 5 | 314 | C18 H19 N O2S |
| 7 | 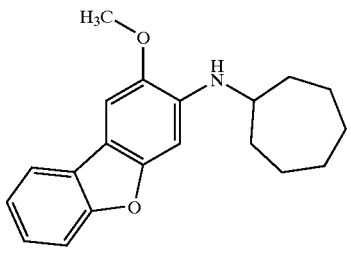 | 5 | 310 | C20 H23 N O2 |
| 8 | 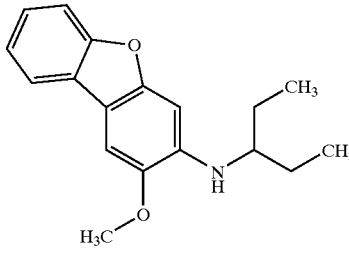 | 5 | 284 | C18 H21 N O2 |

-continued

| Example | MOLSTRUCTURE | General procedure | M + H (APCl)* | MOLECULAR FORMULA |
|---|---|---|---|---|
| 9 | | 5 | 270 | C17 H19 N O2 |
| 10 | | 7,5 | 308 | C20 H25 N3 |
| 11 | | 5 | 371 | C26 H30 N2 |
| 12 | | 5,7 | 265 | C18 H20 N2 |
| 13 | | 5 | 328 | C24 H25 N |
| 14 | | 5,7 | 238 | C17 H19 N |

-continued

| Example | MOLSTRUCTURE | General procedure | M + H (APCl)* | MOLECULAR FORMULA |
|---|---|---|---|---|
| 15 | | 5 | 346 | C18 H19 N O4S |
| 16 | | 6 | 322 | C22 H27 N O |
| 17 | | 6 | 320 | C22 H25 N O |
| 18 | | 6 | 318 | C22 H23 N O |
| 19 | | 6 | 348 | C24 H29 N O |
| 20 | | 6 | 278 | C19 H19 N O |
| 21 | | 6 | 322 | C22 H27 N O |
| 22 | | 6 | 292 | C20 H21 N O |

| Example | MOLSTRUCTURE | General procedure | M + H (APCI)* | MOLECULAR FORMULA |
|---|---|---|---|---|
| 23 | | 6 | 252 | C17 H17 N O |
| 24 | | 6,5 | 296 | C19 H21 N O2 |
| 25 | | 6,5 | 264 | C19 H21 N |
| 26 | | 4 | 360 | C20 H25 N O S2 |
| 27 | | 4 | 324 | C22 H29 N O |
| 28 | | 4 | 268 | C18 H21 N O |

-continued
| Example | MOLSTRUCTURE | General procedure | M + H (APCI)* | MOLECULAR FORMULA |
|---|---|---|---|---|
| 29 | 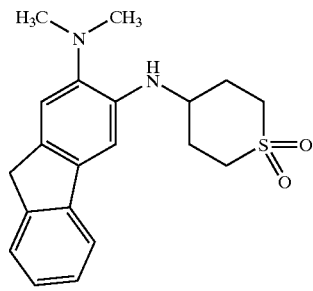 | 5 | 357 | C20 H24 N2 O2 S |
| 30 | 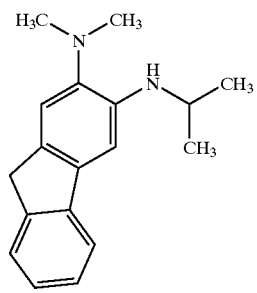 | 5,7 | 267 | C18 H22 N2 |
| 31 | 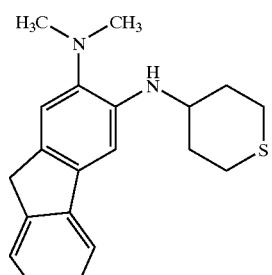 | 5,7 | 325 | C20 H24 N2 S |
| 32 | 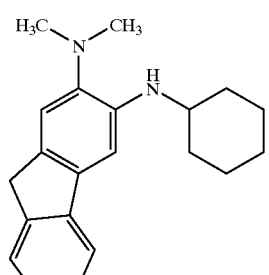 | 5,7 | 307 | C21 H26 N2 |
| 33 | 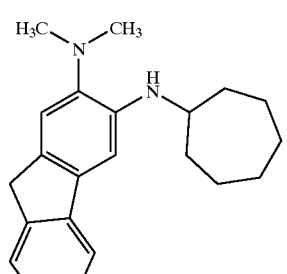 | 5,7 | 321 | C22 H28 N2 |

-continued

| Example | MOLSTRUCTURE | General procedure | M + H (APCI)* | MOLECULAR FORMULA |
|---|---|---|---|---|
| 34 | | 5 | 295 | C20 H26 N2 |
| 35 | | 5 | 293 | C20 H24 N2 |
| 36 | | 5,7 | 281 | C19 H24 N2 |
| 37 | | 5,7 | 224 | C16 H17 N |
| 38 | | 5 | 282 | C18 H19 N S |
| 39 | | 5,7 | 278 | C20 H23 N |

-continued

| Example | MOLSTRUCTURE | General procedure | M + H (APCl)* | MOLECULAR FORMULA |
|---------|--------------|-------------------|---------------|-------------------|
| 40 | | 5 | 316 | C17 H17 N O3 S |
| 41 | | 5,6 | 267 | C17 H18 N2 O |
| 42 | | 5,6 | 226 | C15 H15 N O |
| 43 | | 5,6 | 266 | C18 H19 N O |
| 44 | | 5 | 252 | C17 H17 N O |
| 45 | | 5 | 316 | C17 H17 N O3 S |
| 46 | | 5 | 267 | C17 H18 N2 O |
| 47 | | 5 | 226 | C15 H15 N O |

-continued

| Example | MOLSTRUCTURE | General procedure | M + H (APCl)* | MOLECULAR FORMULA |
|---|---|---|---|---|
| 48 | | 5 | 284 | C17 H17 N O S |
| 49 | | 5 | 266 | C18 H19 N O |
| 50 | | 5 | 280 | C19 H21 N O |
| 51 | | 5 | 308, 310 | C19 H14 Cl N O |
| 52 | | 2 | 353, 355 | C19 H13 Cl N2 O3 |
| 53 | | 2 | 358 | C20 H14 F3 N O2 |

-continued

| Example | MOLSTRUCTURE | General procedure | M + H (APCI)* | MOLECULAR FORMULA |
|---|---|---|---|---|
| 54 | | 2 | 318 | C20 H15 N O3 |
| 55 | | 2 | 332 | C21 H17 N O3 |
| 56 | | 2 | 334 | C21 H19 N O3 |
| 57 | | 2 | 342 | C20 H14 F3 N O |
| 58 | | 1,2,3 | 288 | C20 H17 N O |
| 59 | | 2 | 280 | C17 H13 N O S |

-continued

| Example | MOLSTRUCTURE | General procedure | M + H (APCl)* | MOLECULAR FORMULA |
|---|---|---|---|---|
| 60 | | 2 | 319 | C19 H14 N2 O3 |
| 61 | | 2 | 320 | C20 H17 N O S |
| 62 | | 2 | 288 | C20 H17 N O |
| 63 | | 2 | 274 | C19 H15 N O |
| 64 | | 2 | 380 | C26 H21 N O2 |
| 65 | | 5 | 330 | C23 H23 N O |

-continued
| Example | MOLSTRUCTURE | General procedure | M + H (APCl)* | MOLECULAR FORMULA |
|---|---|---|---|---|
| 66 | 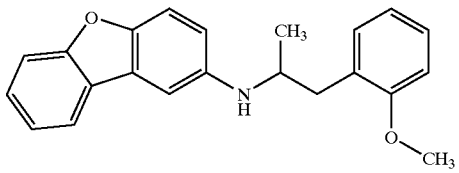 | 5 | 332 | C22 H21 N O2 |
| 67 | 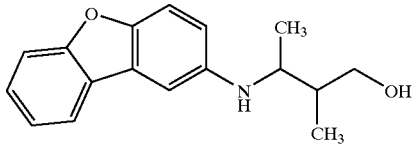 | 5 | 270 | C17 H19 N O2 |
| 68 | 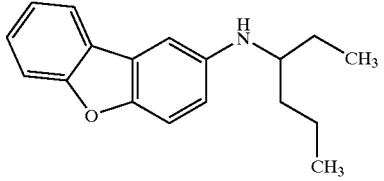 | 5 | 268 | C18 H21 N O |
| 69 | 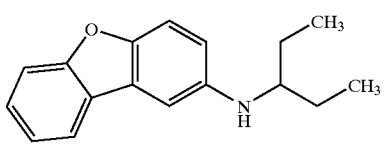 | 5 | 254 | C17 H19 N O |
| 70 | 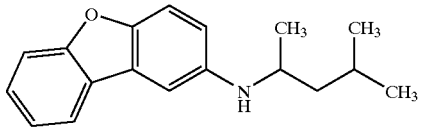 | 5 | 268 | C18 H21 N O |
| 71 | 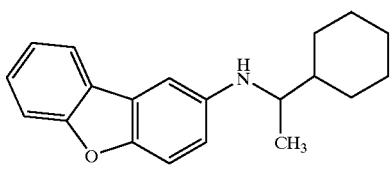 | 5 | 294 | C20 H23 N O |
| 72 | 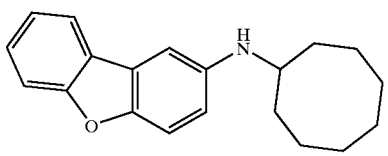 | 5 | 294 | C20 H23 N O |
| 73 | 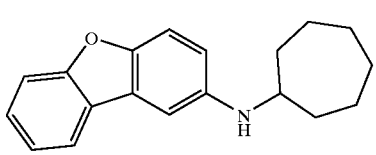 | 5,6 | 280 | C19 H21 N O |
| 74 | 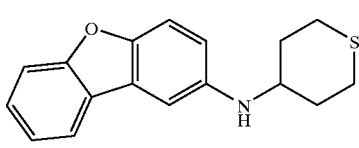 | 5,6 | 284 | C17 H17 N O S |

-continued

| Example | MOLSTRUCTURE | General procedure | M + H (APCI)* | MOLECULAR FORMULA |
|---|---|---|---|---|
| 75 | | 5 | 270 | C16 H15 N O S |
| 76 | | 5 | 254 | C17 H19 N O |
| 77 | | 5 | 254 | C17 H19 N O |
| 78 | | 5,6 | 240 | C16 H17 N O |
| 79 | | 3 | 293 | C18 H13 F N2 O |
| 80 | | 3 | 276 | C17 H13 N3 O |
| 81 | | 3 | 289 | C19 H16 N2 O |

-continued

| Example | MOLSTRUCTURE | General procedure | M + H (APCl)* | MOLECULAR FORMULA |
|---|---|---|---|---|
| 82 | | 3 | 321 | C20 H17 F N2 O |
| 83 | | 3 | 354 | C23 H19 N3 O |
| 85 | | 3 | 381 | C21 H20 N2 O3 S |
| 86 | | 3 | 304 | C19 H17 N3 O |

-continued

| Example | MOLSTRUCTURE | General procedure | M + H (APCl)* | MOLECULAR FORMULA |
|---|---|---|---|---|
| 87 | | 3 | 317 | C21 H20 N2 O |
| 88 | | 3,2 | 355 | C23 H18 N2 S |
| 89 | | 3 | 383 | C20 H18 N2 O2 S |
| 90 | | 3 | 339 | C19 H15 F N2 O S |
| 91 | | 3 | 325 | C18 H13 F N2 O S |
| 92 | | 3 | 358 | C21 H15 N3 O S |

-continued

| Example | MOLSTRUCTURE | General procedure | M + H (APCl)* | MOLECULAR FORMULA |
|---|---|---|---|---|
| 93 | | 3 | 357 | C22 H16 N2 O S |
| 94 | | 3 | 385 | C19 H16 N2 O3 S |
| 95 | | 3 | 308 | C17 H13 N3 O S |
| 96 | | 3 | 321 | C19 H16 N2 O S |
| 97 | | 3 | 335 | C24 H18 N2 |

-continued

| Example | MOLSTRUCTURE | General procedure | M + H (APCl)* | MOLECULAR FORMULA |
|---|---|---|---|---|
| 98 | | 3 | 362 | C22 H19 N O2 S |
| 99 | | 3 | 285 | C20 H16 N2 |
| 100 | | 3 | 298 | C22 H19 N |
| 101 | | 3 | 322 | C20 H16 F N O2 |
| 102 | | 3 | 308 | C19 H14 F N O2 |

-continued
| Example | MOLSTRUCTURE | General procedure | M + H (APCl)* | MOLECULAR FORMULA |
|---|---|---|---|---|
| 103 | 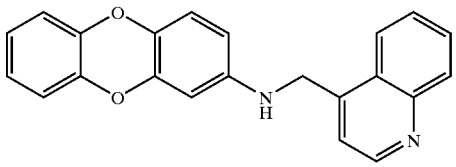 | 3 | 341 | C22 H16 N2 O2 |
| 104 | 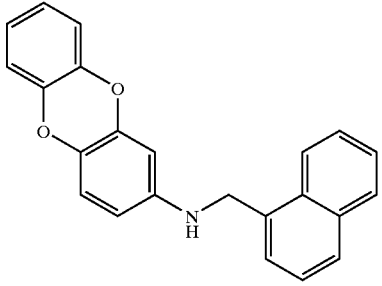 | 3 | 340 | C23 H17 N O2 |
| 105 | 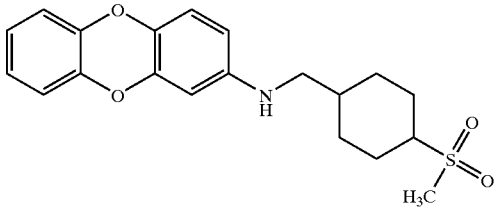 | 3 | 368 | C20 H17 N O4 S |
| 106 | 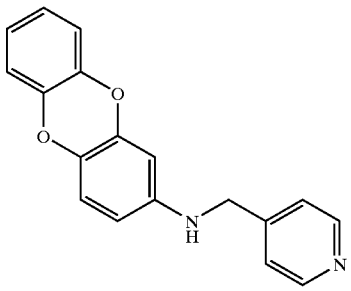 | 3 | 291 | C18 H14 N2 O2 |
| 107 | 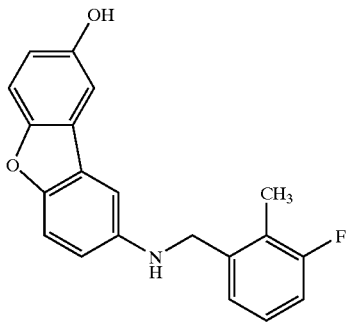 | 3 | 322 | C20 H16 F N O2 |

-continued

| Example | MOLSTRUCTURE | General procedure | M + H (APCl)* | MOLECULAR FORMULA |
|---------|--------------|-------------------|---------------|-------------------|
| 108 | | 3 | 308 | C19 H14 F N O2 |
| 109 | | 3 | 368 | C20 H17 N O4 S |
| 110 | | 3 | 291 | C18 H14 N2 O2 |
| 111 | | 3 | 304 | C20 H17 N O2 |

-continued

| Example | MOLSTRUCTURE | General procedure | M + H (APCl)* | MOLECULAR FORMULA |
|---|---|---|---|---|
| 112 | | 3 | 326, 328 | C19 H13 Cl F N O |
| 113 | | 3 | 359 | C23 H16 Cl N O |
| 114 | | 3 | 387 | C20 H16 Cl N O3 S |
| 115 | | 3 | 355 | C20 H22 N2 O2 S |
| 116 | | 3 | 278 | C18 H19 N3 |

-continued

| Example | MOLSTRUCTURE | General procedure | M + H (APCl)* | MOLECULAR FORMULA |
|---|---|---|---|---|
| 117 | | 3 | 307 | C19 H15 F N2 O |
| 118 | | 2,3 | 325 | C22 H16 N2 O |
| 119 | | 2 | 325 | C22 H16 N2 O |
| 120 | | 2 | 335 | C21 H19 F N2 O |
| 121 | | 2 | 317 | C21 H20 N2 O |

-continued

| Example | MOLSTRUCTURE | General procedure | M + H (APCl)* | MOLECULAR FORMULA |
|---|---|---|---|---|
| 122 | | 2 | 325 | C17 H12 N2 O3 S |
| 123 | | 2 | 281 | C16 H12 N2 O S |
| 124 | | 2 | 292 | C19 H14 F N O |
| 125 | | 2 | 333 | C21 H20N2O2 |
| 126 | | 2 | 363 | C22H22N2O3 |

-continued

| Example | MOLSTRUCTURE | General procedure | M + H (APCl)* | MOLECULAR FORMULA |
|---|---|---|---|---|
| 127 | | 2 | 359 | C24H26N2O1 |
| 128 | | 2 | 303 | C20H18N2O1 |
| 129 | | 2 | 328 | C21H17N3O1 |
| 130 | | 2 | 336 | C20H17N1O2S1 |
| 131 | | 2 | 338,340 | C20H16N1O2Cl1 |

-continued

| Example | MOLSTRUCTURE | General procedure | M + H (APCI)* | MOLECULAR FORMULA |
|---|---|---|---|---|
| 132 | | 2 | 336 | C20H17O2S1N1 |
| 133 | | 2 | 366 | C21H19O3N1S1 |
| 134 | | 2 | 354 | C20H16O2N1S1F1 |
| 135 | | 2 | 362 | C23H23O1N1S1 |
| 136 | | 2 | 306 | C19H15N1O1S1 |
| 137 | | 2 | 350 | C21H19N1O2S1 |

-continued

| Example | MOLSTRUCTURE | General procedure | M + H (APCl)* | MOLECULAR FORMULA |
|---|---|---|---|---|
| 138 | 8-chloro-dibenzofuran-2-yl-(3,5-dimethoxy-benzyl)-amine | 2 | 368,370 | C21H18N1O3Cl1 |
| 139 | 8-chloro-dibenzofuran-2-yl-(3-fluoro-4-methoxy-benzyl)-amine | 2 | 356,358 | C20H15N1O2Cl1F1 |
| 140 | benzyl-(8-chloro-dibenzofuran-2-yl)-amine | 2 | 308,310 | C19H14NOCl |
| 141 | (9H-fluoren-2-yl)-(4-methoxy-benzyl)-amine | 2 | 302 | C21H19NO |

-continued

| Example | MOLSTRUCTURE | General procedure | M + H (APCI)* | MOLECULAR FORMULA |
|---|---|---|---|---|
| 142 | | 2 | 315,317 | C15H11N2OClS |
| 143 | | 2 | 302 | C21H19NO |
| 144 | | 2 | 332 | C22H21NO2 |
| 145 | | 2 | 320 | C21H18NOF |
| 146 | | 2 | 328 | C24H25N |
| 147 | | 2 | 272 | C20H17N1 |

-continued
| Example | MOLSTRUCTURE | General procedure | M + H (APCl)* | MOLECULAR FORMULA |
|---|---|---|---|---|
| 148 | 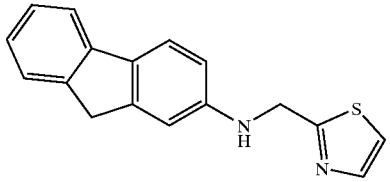 | 2 | 279 | C16H14N2S |
| 149 | 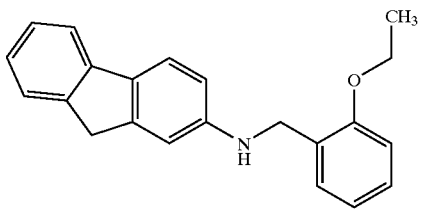 | 2 | 316 | C22H21NO |
| 150 | 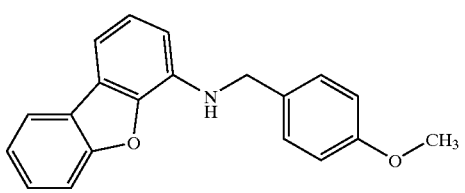 | 2 | 304 | C20H17NO2 |
| 151 | 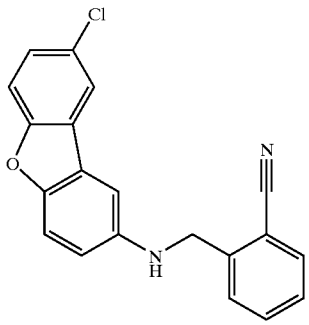 | 2 | 334 | C20H13N2Ocl |
| 152 | 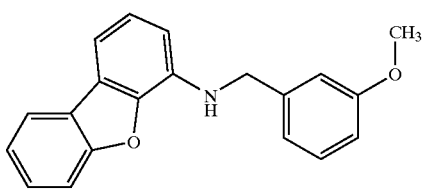 | 2 | 304 | C20H17NO2 |
| 153 | 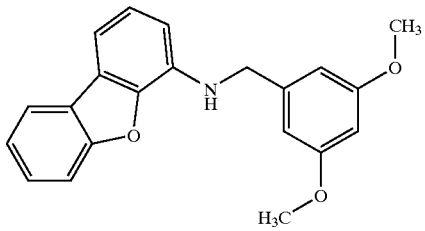 | 2 | 334 | C21H19NO3 |

-continued

| Example | MOLSTRUCTURE | General procedure | M + H (APCl)* | MOLECULAR FORMULA |
|---------|--------------|-------------------|---------------|-------------------|
| 154 | | 2 | 322 | C20H16NFO2 |
| 155 | | 2 | 330 | C23H23NO |
| 156 | | 2 | 318 | C21H19NO2 |
| 157 | | 2 | 333 | C21H20N2O2 |
| 158 | | 2 | 338, 340 | C20H16NO2Cl |

-continued

| Example | MOLSTRUCTURE | General procedure | M + H (APCl)* | MOLECULAR FORMULA |
|---|---|---|---|---|
| 159 | | 2 | 352,354 | C21H18NO2Cl |
| 160 | | 2 | 302 | C21 H19 N O |
| 161 | | 2 | 309 | C18 H16 N2 O S |
| 162 | | 2 | 304 | C19 H17 N3 O |
| 163 | | 2 | 383,385 | C19 H14 Br N O S |

-continued

| Example | MOLSTRUCTURE | General procedure | M + H (APCI)* | MOLECULAR FORMULA |
|---|---|---|---|---|
| 164 | | 2 | 357 | C22 H16 N2 O S |
| 165 | | 2 | 312 | C17 H13 N O S2 |
| 166 | | 2 | 321 | C19 H16 N2 O S |
| 167 | | 2 | 307 | C18 H14 N2 O S |
| 168 | | 2 | 307 | C18 H14 N2 O S |
| 169 | | 2 | 314,316 | C17 H12 Cl N O S |

-continued

| Example | MOLSTRUCTURE | General procedure | M + H (APCl)* | MOLECULAR FORMULA |
|---|---|---|---|---|
| 170 | | 2 | 379,381 | C21 H19 Br N2 |
| 171 | | 2 | 323,325 | C19 H15 Cl N2 O |
| 172 | | 2 | 307 | C19 H18 N2 S |
| 173 | | 2 | 341,342 | C19 H17 Cl N2 S |
| 174 | | 2 | 302 | C20 H19 N3 |

-continued

| Example | MOLSTRUCTURE | General procedure | M + H (APCl)* | MOLECULAR FORMULA |
|---|---|---|---|---|
| 175 | | 2 | 350,352 | C20 H16 Br N |
| 176 | | 2,3 | 309,311 | C18 H13 Cl N2 O |
| 177 | | 2 | 323 | C23 H18 N2 |
| 178 | | 2 | 278 | C18 H15 N S |
| 179 | | 2 | 287 | C20 H18 N2 |
| 180 | | 2 | 273 | C19 H16 N2 |
| 181 | | 2 | 273 | C19 H16 N2 |

-continued

| Example | MOLSTRUCTURE | General procedure | M + H (APCI)* | MOLECULAR FORMULA |
|---|---|---|---|---|
| 182 | | 2 | 273 | C19 H16 N2 |
| 183 | | 2 | 309,311 | C18 H13 Cl N2 O |
| 184 | | 2 | 325 | C22 H16 N2 O |
| 185 | | 2 | 325 | C22 H16 N2 O |
| 186 | | 2 | 280 | C17 H13 N O S |
| 187 | | 2 | 289 | C19 H16 N2 O |
| 188 | | 2 | 275 | C18 H14 N2 O |

-continued

| Example | MOLSTRUCTURE | General procedure | M + H (APCl)* | MOLECULAR FORMULA |
|---|---|---|---|---|
| 189 | | 2 | 275 | C18 H14 N2 O |
| 190 | | 2 | 275 | C18 H14 N2 O |
| 191 | | 2 | 387,389 | C19 H13 Br Cl N O |
| 192 | | 2 | 309,311 | C18 H13 Cl N2 O |
| 193 | | 2 | 357 | C20 H15 F3 N2 O |

-continued

| Example | MOLSTRUCTURE | General procedure | M + H (APCl)* | MOLECULAR FORMULA |
|---|---|---|---|---|
| 194 | | 2 | 357 | C20 H15 F3 N2 O |
| 195 | | 2 | 339 | C20 H16 F2 N2 O |
| 196 | | 2 | 339 | C20 H16 F2 N2 O |
| 197 | | 2 | 339 | C20 H16 F2 N2 O |

-continued

| Example | MOLSTRUCTURE | General procedure | M + H (APCI)* | MOLECULAR FORMULA |
|---|---|---|---|---|
| 198 | | 2 | 339 | C20 H16 F2 N2 O |
| 199 | | 2 | 331 | C22 H22 N2 O |
| 200 | | 2 | 331 | C22 H22 N2 O |
| 201 | | 2 | 361 | C22 H20 N2 O3 |

-continued

| Example | MOLSTRUCTURE | General procedure | M + H (APCI)* | MOLECULAR FORMULA |
|---------|--------------|-------------------|---------------|-------------------|
| 202 | | 2 | 338 | C20 H16 F N O S |
| 203 | | 2 | 363 | C19 H11 Cl F3 N O |
| 204 | | 2 | 360 | C19 H12 F3 N O S |
| 205 | | 2 | 360 | C19 H12 F3 N O S |
| 206 | | 2 | 342 | C19 H13 F2 N O S |
| 207 | | 2 | 342 | C19 H13 F2 N O S |

-continued

| Example | MOLSTRUCTURE | General procedure | M + H (APCl)* | MOLECULAR FORMULA |
|---|---|---|---|---|
| 208 | | 2 | 342 | C19 H13 F2 N O S |
| 209 | | 2 | 342 | C19 H13 F2 N O S |
| 210 | | 2 | 334 | C21 H19 N O S |
| 211 | | 2 | 364 | C21 H17 N O3 S |
| 212 | | 2 | 272 | C16 H14 F N S |

-continued

| Example | MOLSTRUCTURE | General procedure | M + H (APCl)* | MOLECULAR FORMULA |
|---|---|---|---|---|
| 213 | | 2 | 363 | C19 H11 Cl F3 N O |
| 214 | | 2 | 345 | C19 H12 Cl F2 N O |
| 215 | | 2 | 345 | C19 H12 Cl F2 N O |
| 216 | | 2 | 345 | C19 H12 Cl F2 N O |

-continued

| Example | MOLSTRUCTURE | General procedure | M + H (APCI)* | MOLECULAR FORMULA |
|---|---|---|---|---|
| 217 | | 2 | 333 | C22 H21 F N2 |
| 218 | | 2 | 345 | C19 H12 Cl F2 N O |
| 219 | | 2 | 355 | C21 H17 F3 N2 |
| 220 | | 2 | 355 | C21 H17 F3 N2 |
| 221 | | 2 | 337 | C21 H18 F2 N2 |

-continued

| Example | MOLSTRUCTURE | General procedure | M + H (APCl)* | MOLECULAR FORMULA |
|---|---|---|---|---|
| 222 | (9-ethylcarbazol-3-yl)-NH-CH2-(2,5-difluorophenyl) | 2 | 337 | C21 H18 F2 N2 |
| 223 | (9-ethylcarbazol-3-yl)-NH-CH2-(2,4-difluorophenyl) | 2 | 337 | C21 H18 F2 N2 |
| 224 | (9-ethylcarbazol-3-yl)-NH-CH2-(2,3-difluorophenyl) | 2 | 337 | C21 H18 F2 N2 |
| 225 | (9-ethylcarbazol-3-yl)-NH-CH2-(2,5-dimethylphenyl) | 2 | 329 | C23 H24 N2 |
| 226 | (9-ethylcarbazol-3-yl)-NH-CH2-(2,4-dimethylphenyl) | 2 | 329 | C23 H24 N2 |

-continued
| Example | MOLSTRUCTURE | General procedure | M + H (APCl)* | MOLECULAR FORMULA |
|---|---|---|---|---|
| 227 | 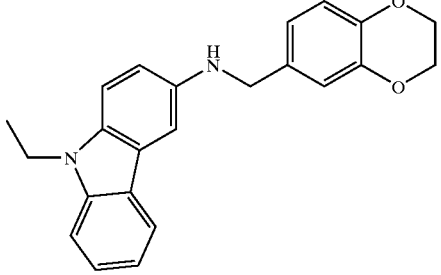 | 2 | 359 | C23 H22 N2 O2 |
| 228 | 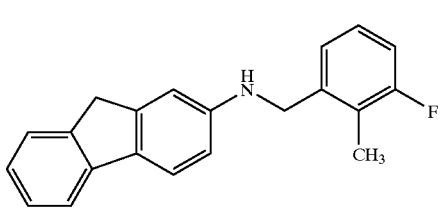 | 2 | 304 | C21 H18 F N |
| 229 | 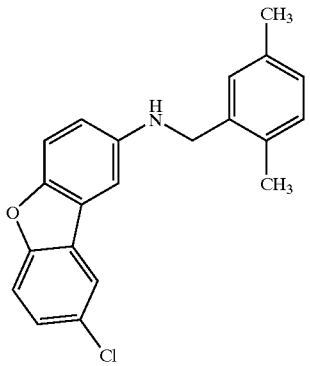 | 2 | 337 | C21 H18 Cl N O |
| 230 | 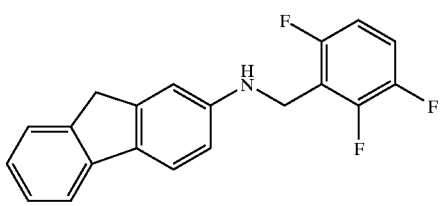 | 2 | 326 | C20 H14 F3 N |
| 231 | 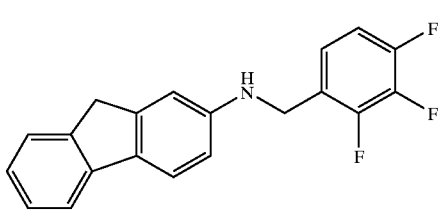 | 2 | 326 | C20 H14 F3 N |
| 232 | 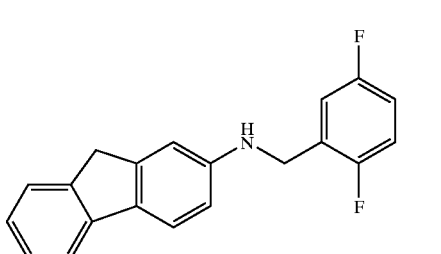 | 2 | 308 | C20 H15 F2 N |

-continued

| Example | MOLSTRUCTURE | General procedure | M + H (APCl)* | MOLECULAR FORMULA |
|---|---|---|---|---|
| 233 | | 2 | 308 | C20 H15 F2 N |
| 234 | | 2 | 308 | C20 H15 F2 N |
| 235 | | 2 | 300 | C22 H21 N |
| 236 | | 2 | 300 | C22 H21 N |
| 237 | | 2 | 330 | C22 H19 N O2 |
| 238 | | 2 | 336,338 | C21 H18 Cl N O |

-continued

| Example | MOLSTRUCTURE | General procedure | M + H (APCl)* | MOLECULAR FORMULA |
|---------|--------------|-------------------|---------------|-------------------|
| 239 | | 2 | 302 | C21 H19 N O |
| 240 | | 2 | 306 | C20 H16 F N O |
| 241 | | 2,3 | 335 | C21 H19 F N2 O |
| 242 | | 2,3 | 341 | C20 H15 Cl F N O |
| 243 | | 2 | 367 | C21 H16 Cl N O3 |

-continued

| Example | MOLSTRUCTURE | General procedure | M + H (APCl)* | MOLECULAR FORMULA |
| --- | --- | --- | --- | --- |
| 244 | | 2 | 366 | C21 H19 N O3 S |
| 245 | | 2 | 366 | C21 H19 N O3 S |
| 246 | | 2 | 340,342 | C19 H14 Cl N O S |
| 247 | | 2 | 336 | C20 H17 N O2 S |
| 248 | | 2 | 320 | C20 H17 N O S |
| 249 | | 2 | 318,320 | C21 H16 Cl N |

-continued

| Example | MOLSTRUCTURE | General procedure | M + H (APCl)* | MOLECULAR FORMULA |
|---|---|---|---|---|
| 250 | | 2 | 302 | C21 H16 F N |
| 251 | | 2 | 350 | C21 H19 N O4 |
| 252 | | 2 | 324,326 | C19 H14 Cl N O2 |
| 253 | | 2 | 306 | C19 H15 N O3 |
| 254 | | 2 | 320 | C20 H17 N O3 |

-continued

| Example | MOLSTRUCTURE | General procedure | M + H (APCl)* | MOLECULAR FORMULA |
|---|---|---|---|---|
| 255 | | 2 | 317 | C21 H20 N2 O |
| 256 | | 2 | 319 | C21 H19 F N2 |
| 257 | | 2 | 315 | C22 H22 N2 |
| 258 | | 2 | 306,308 | C20 H16 Cl N |
| 259 | | 2 | 288 | C20 H17 N O |
| 260 | | 2 | 302 | C21 H19 N O |

-continued

| Example | MOLSTRUCTURE | General procedure | M + H (APCl)* | MOLECULAR FORMULA |
|---|---|---|---|---|
| 261 | | 2 | 340 | C21 H16 F3 N |
| 262 | | 2 | 290 | C20 H16 F N |
| 263 | | 2 | 334 | C21 H19 N O3 |
| 264 | | 2 | 334 | C21 H19 N O3 |
| 265 | | 2 | 290 | C19 H15 N O2 |
| 266 | | 2 | 304 | C20 H17 N O2 |

-continued

| Example | MOLSTRUCTURE | General procedure | M + H (APCl)* | MOLECULAR FORMULA |
|---|---|---|---|---|
| 267 | | 2 | 364 | C22 H21 N O4 |
| 268 | | 2 | 364 | C22 H21 N O4 |
| 269 | | 2 | 334 | C21 H19 N O3 |
| 270 | | 2 | 334 | C21 H19 N O3 |

-continued

| Example | MOLSTRUCTURE | General procedure | M + H (APCI)* | MOLECULAR FORMULA |
|---|---|---|---|---|
| 271 | | 2 | 304 | C20 H17 N O2 |
| 272 | | 2 | 351,353 | C19 H14 Br N O |
| 273 | | 2 | 282 | C16 H12 F N3 O |
| 274 | | 2 | 317 | C20 H13 F N2 O |
| 275 | | 2 | 336 | C21 H18 F N O2 |

-continued

| Example | MOLSTRUCTURE | General procedure | M + H (APCl)* | MOLECULAR FORMULA |
|---|---|---|---|---|
| 276 | | 2 | 338 | C20 H16 F N O S |
| 277 | | 2 | 369,371 | C19 H13 Br F N O |
| 278 | | 2 | 343 | C22 H15 F N2 O |
| 279 | | 2 | 343 | C22 H15 F N2 O |
| 280 | | 2,3 | 324 | C23 H17 N O |

-continued

| Example | MOLSTRUCTURE | General procedure | M + H (APCl)* | MOLECULAR FORMULA |
|---------|--------------|-------------------|---------------|-------------------|
| 281 | | 2 | 342 | C23 H16 F N O |
| 282 | | 2 | 342 | C23 H16 F N O |
| 283 | | 2 | 319 | C19 H14 N2 O3 |
| 284 | | 2 | 264 | C16 H13 N3 O |
| 285 | | 2 | 299 | C20 H14 N2 O |

-continued

| Example | MOLSTRUCTURE | General procedure | M + H (APCl)* | MOLECULAR FORMULA |
|---|---|---|---|---|
| 286 | | 2 | 318 | C21 H19 N O2 |
| 287 | | 2 | 342 | C20 H14 F3 N O |
| 288 | | 2 | 330 | C23 H23 N O |
| 289 | | 2 | 292 | C19 H14 F N O |

-continued
| Example | MOLSTRUCTURE | General procedure | M + H (APCI)* | MOLECULAR FORMULA |
|---|---|---|---|---|
| 290 | 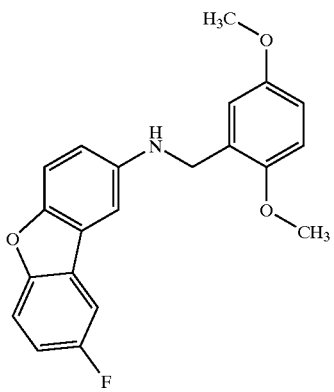 | 2 | 352 | C21 H18 F N O3 |
| 291 | 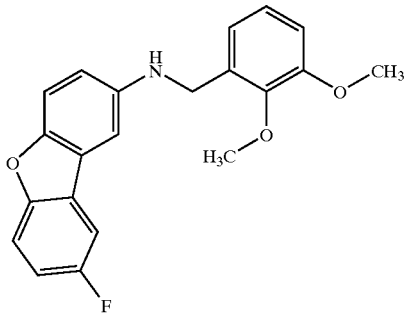 | 2 | 352 | C21 H18 F N O3 |
| 292 | 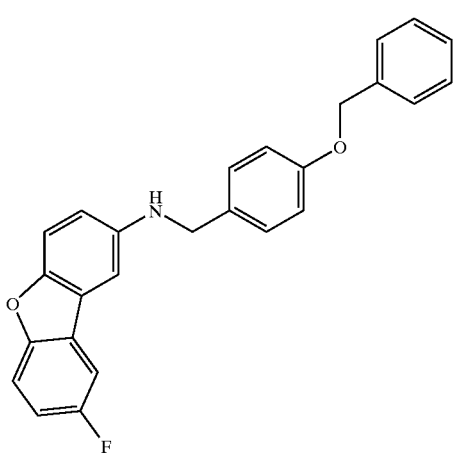 | 2 | 398 | C26 H20 F N O2 |
| 293 | 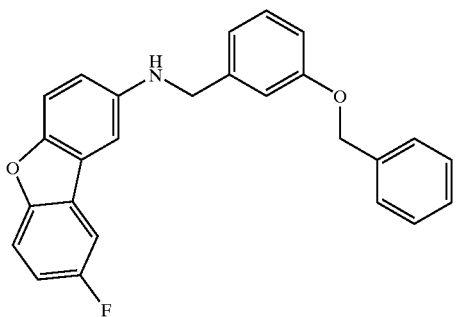 | 2 | 398 | C26 H20 F N O2 |

-continued
| Example | MOLSTRUCTURE | General procedure | M + H (APCl)* | MOLECULAR FORMULA |
|---|---|---|---|---|
| 294 | 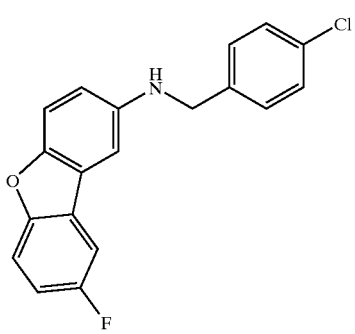 | 2 | 326,328 | C19 H13 Cl F N O |
| 295 | 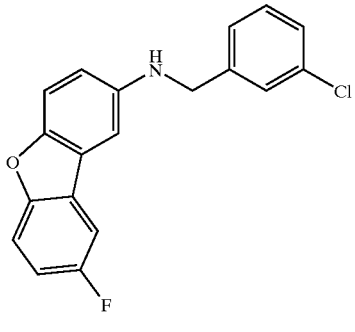 | 2 | 326,328 | C19 H13 Cl F N O |
| 296 | 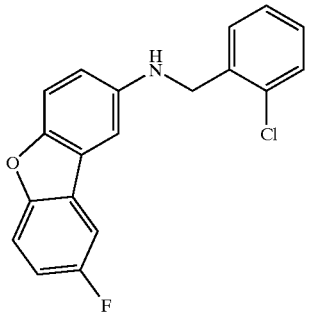 | 2 | 326,328 | C19 H13 Cl F N O |
| 297 | 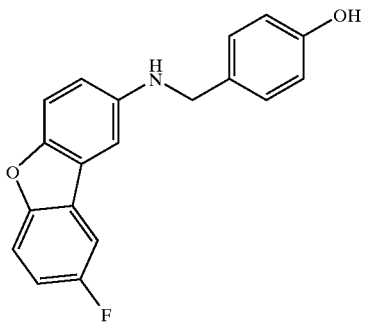 | 2 | 308 | C19 H14 F N O2 |

-continued

| Example | MOLSTRUCTURE | General procedure | M + H (APCl)* | MOLECULAR FORMULA |
|---|---|---|---|---|
| 298 | | 2,3 | 308 | C19 H14 F N O2 |
| 299 | | 2 | 292 | C19 H14 F N O |
| 300 | | 2 | 322 | C20 H16 F N O2 |
| 301 | | 2 | 322 | C20 H16 F N O2 |

-continued

| Example | MOLSTRUCTURE | General procedure | M + H (APCl)* | MOLECULAR FORMULA |
|---|---|---|---|---|
| 302 | | 2 | 322 | C20 H16 F N O2 |
| 303 | | 2 | 360 | C20 H13 F4 N O |
| 304 | | 2 | 360 | C20 H13 F4 N O |
| 305 | | 2 | 348 | C23 H22 F N O |

-continued
| Example | MOLSTRUCTURE | General procedure | M + H (APCl)* | MOLECULAR FORMULA |
|---|---|---|---|---|
| 306 | 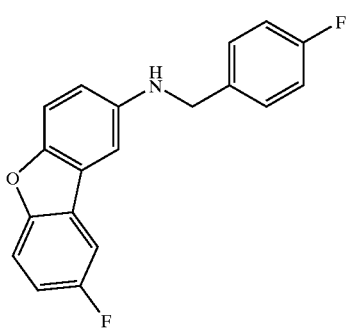 | 2 | 310 | C19 H13 F2 N O |
| 307 | 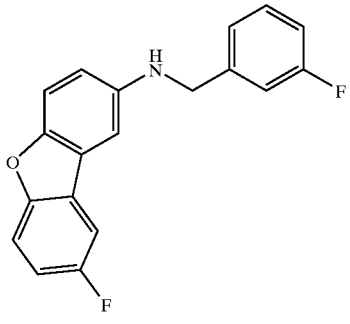 | 2 | 310 | C19 H13 F2 N O |
| 308 | 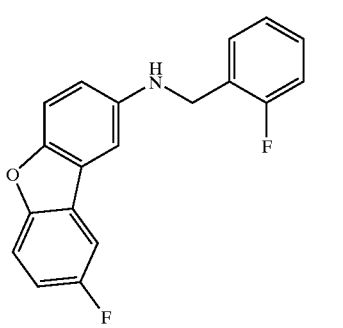 | 2,3 | 310 | C19 H13 F2 N O |
| 309 | 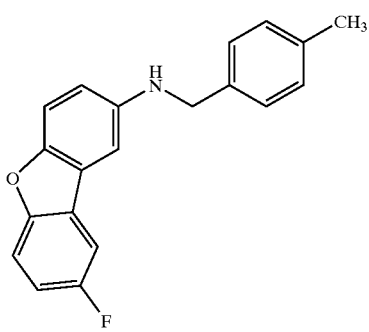 | 2 | 306 | C20 H16 F N O |

-continued

| Example | MOLSTRUCTURE | General procedure | M + H (APCl)* | MOLECULAR FORMULA |
|---|---|---|---|---|
| 310 | | 2 | 306 | C20 H16 F N O |
| 311 | | 2 | 334 | C21 H19 N O3 |
| 312 | | 2 | 334 | C21 H19 N O3 |
| 313 | | 2 | 334 | C21 H19 N O3 |

-continued

| Example | MOLSTRUCTURE | General procedure | M + H (APCl)* | MOLECULAR FORMULA |
|---|---|---|---|---|
| 314 | | 2 | 380 | C26 H21 N O2 |
| 315 | | 2 | 288 | C20 H17 N O |
| 316 | | 2 | 308,310 | C19 H14 Cl N O |
| 317 | | 2 | 290 | C19 H15 N O2 |
| 318 | | 2 | 308,310 | C19 H14 Cl N O |

-continued
| Example | MOLSTRUCTURE | General procedure | M + H (APCl)* | MOLECULAR FORMULA |
|---|---|---|---|---|
| 319 | 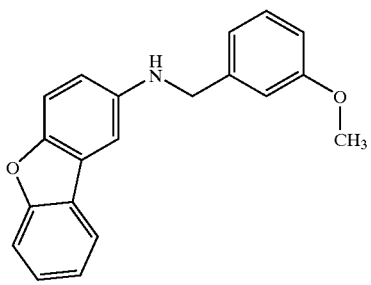 | 2 | 304 | C20 H17 N O2 |
| 320 | 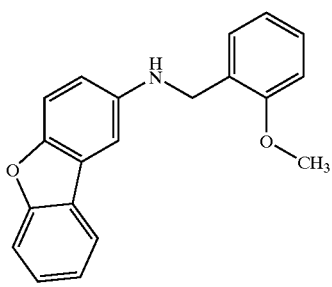 | 2 | 304 | C20 H17 N O2 |
| 321 | 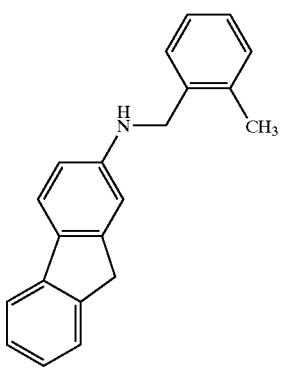 | 2 | 286 | C21 H19 N |
| 322 | 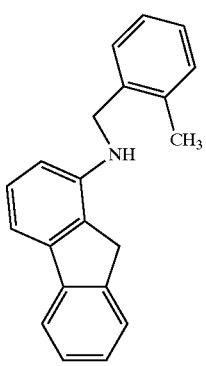 | 2 | 288 | C20 H17 N O |

-continued
| Example | MOLSTRUCTURE | General procedure | M + H (APCl)* | MOLECULAR FORMULA |
|---|---|---|---|---|
| 323 | 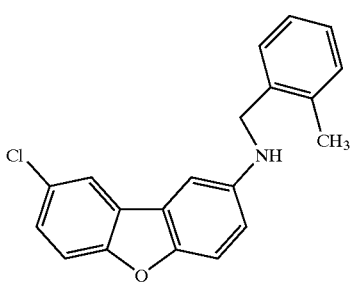 | 2,3 | 323 | C20 H16 Cl N O |
| 324 | 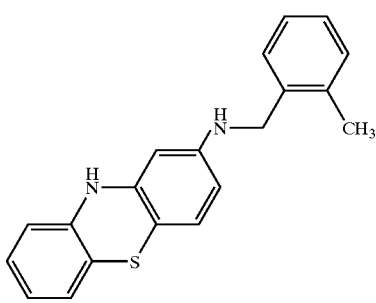 | 2 | 319 | C20 H18 N2 S |
| 325 | 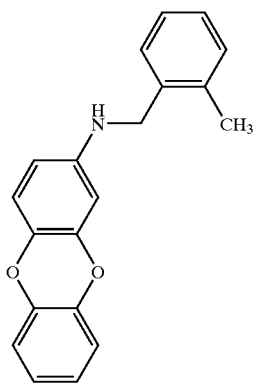 | 2,3 | 304 | C20 H17 N O2 |
| 326 | 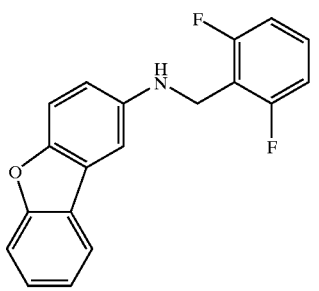 | 2 | 310 | C19 H13 F2 N O |

| Example | MOLSTRUCTURE | General procedure | M + H (APCl)* | MOLECULAR FORMULA |
|---|---|---|---|---|
| 327 | | 2 | 310 | C19 H13 F2 N O |
| 328 | | 2 | 310 | C19 H13 F2 N O |
| 329 | | 2 | 310 | C19 H13 F2 N O |
| 330 | | 2 | 298 | C17 H12 F N O S |
| 331 | | 2 | 302 | C21 H19 N O |

-continued
| Example | MOLSTRUCTURE | General procedure | M + H (APCl)* | MOLECULAR FORMULA |
|---|---|---|---|---|
| 332 | 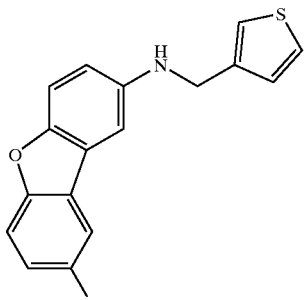 | 2 | 298 | C17 H12 F N O S |
| 333 | 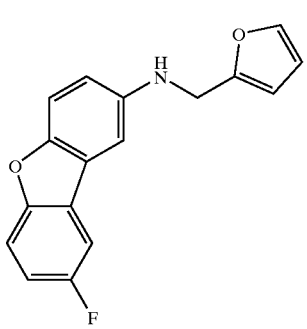 | 2 | 282 | C17 H12 F N O2 |
| 334 | 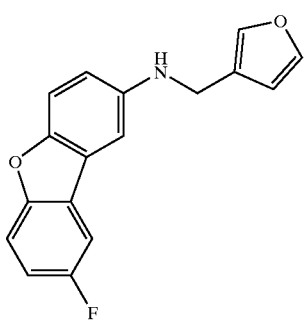 | 2 | 282 | C17 H12 F N O2 |
| 335 | 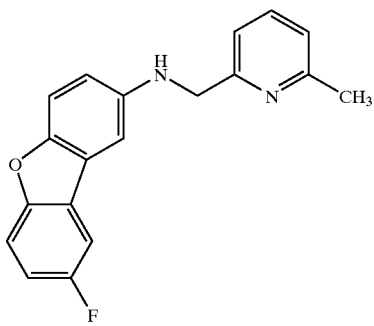 | 2 | 307 | C19 H15 F N2 O |

-continued

| Example | MOLSTRUCTURE | General procedure | M + H (APCl)* | MOLECULAR FORMULA |
|---|---|---|---|---|
| 336 | | 2 | 370 | C20 H16 F N O3 S |
| 337 | | 2,3 | 293 | C18 H13 F N2 O |
| 338 | | 2 | 293 | C18 H13 F N2 O |
| 339 | | 2 | 293 | C18 H13 F N2 O |

-continued

| Example | MOLSTRUCTURE | General procedure | M + H (APCI)* | MOLECULAR FORMULA |
|---|---|---|---|---|
| 340 | | 2 | 340 | C20 H15 F2 N O2 |
| 341 | | 2 | 302 | C21 H19 N O |
| 342 | | 2,3 | 324 | C20 H15 F2 N O |
| 343 | | 2 | 346 | C19 H11 F4 N O |

-continued

| Example | MOLSTRUCTURE | General procedure | M + H (APCl)* | MOLECULAR FORMULA |
|---|---|---|---|---|
| 344 | | 2 | 346 | C19 H11 F4 N O |
| 345 | | 2 | 328 | C19 H12 F3 N O |
| 346 | | 2 | 328 | C19 H12 F3 N O |
| 347 | | 2 | 328 | C19 H12 F3 N O |

-continued

| Example | MOLSTRUCTURE | General procedure | M + H (APCl)* | MOLECULAR FORMULA |
|---|---|---|---|---|
| 348 | | 2 | 328 | C19 H12 F3 N O |
| 349 | | 2 | 328 | C19 H12 F3 N O |
| 350 | | 2 | 328 | C19 H12 F3 N O |
| 351 | | 2 | 320 | C21 H18 F N O |

-continued
| Example | MOLSTRUCTURE | General procedure | M + H (APCl)* | MOLECULAR FORMULA |
|---|---|---|---|---|
| 352 | 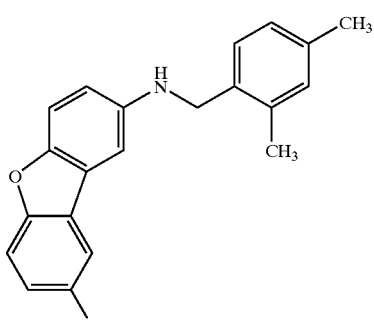 | 2 | 320 | C21 H18 F N O |
| 353 | 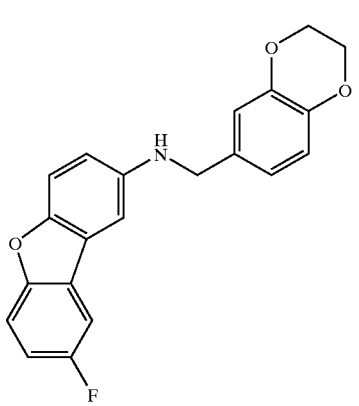 | 2 | 350 | C21 H16 F N O3 |
| 354 | 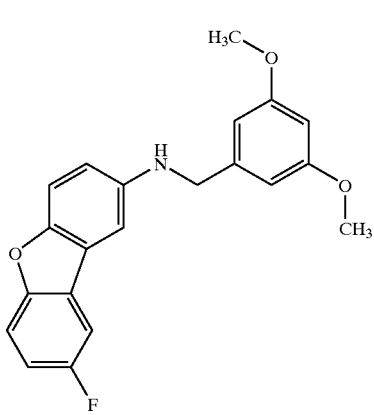 | 2 | 352 | C21 H18 F N O3 |
| 355 | 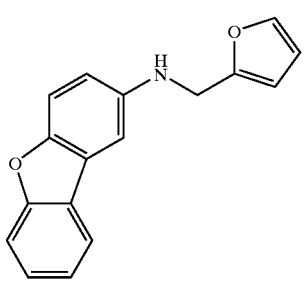 | 2 | 264 | C17 H13 N O2 |

-continued

| Example | MOLSTRUCTURE | General procedure | M + H (APCl)* | MOLECULAR FORMULA |
|---|---|---|---|---|
| 356 | | 2 | 264 | C17 H13 N O2 |
| 357 | | 2 | 289 | C19 H16 N2 O |
| 358 | | 2,3 | 352 | C20 H17 N O3 S |
| 359 | | 2,3 | 275 | C18 H14 N2 O |
| 360 | | 2 | 275 | C18 H14 N2 O |

-continued
| Example | MOLSTRUCTURE | General procedure | M + H (APCI)* | MOLECULAR FORMULA |
|---|---|---|---|---|
| 361 | 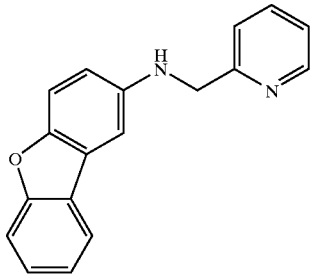 | 2 | 275 | C18 H14 N2 O |
| 362 | 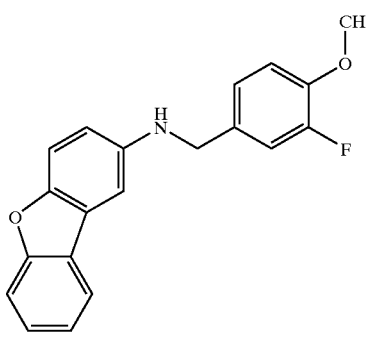 | 2 | 322 | C20 H16 F N O2 |
| 363 | 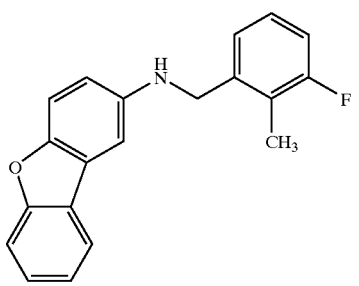 | 2,3 | 306 | C20 H16 F N O |
| 364 | 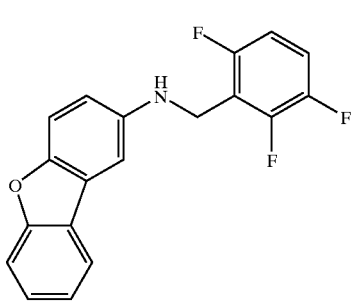 | 2 | 328 | C19 H12 F3 N O |
| 365 | 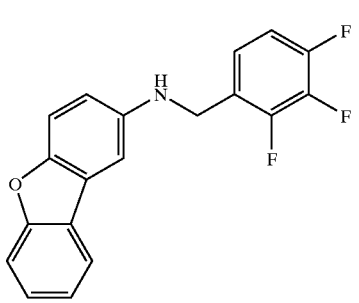 | 2 | 328 | C19 H12 F3 N O |

-continued

| Example | MOLSTRUCTURE | General procedure | M + H (APCI)* | MOLECULAR FORMULA |
|---|---|---|---|---|
| 366 | | 2 | 310 | C19 H13 F2 N O |
| 367 | | 2 | 310 | C19 H13 F2 N O |
| 368 | | 2 | 334 | C21 H19 N O3 |
| 369 | | 2 | 304 | C20H17NS |
| 370 | | 2 | 318 | C21H19NS |

-continued

| Example | MOLSTRUCTURE | General procedure | M + H (APCI)* | MOLECULAR FORMULA |
|---|---|---|---|---|
| 371 | | 2 | 346 | C23H23NS |
| 372 | | 2 | 323,325 | C19H14ClNS |
| 373 | | 2 | 326 | C19H13F2NS |
| 374 | | 2 | 344 | C19H12F3NS |
| 375 | | 2 | 308 | C19H14FNS |

| Example | MOLSTRUCTURE | General procedure | M + H (APCI)* | MOLECULAR FORMULA |
|---|---|---|---|---|
| 376 | 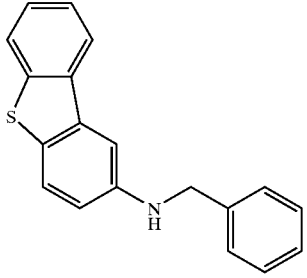 | 2 | 290 | C19H15NS |
| 377 | 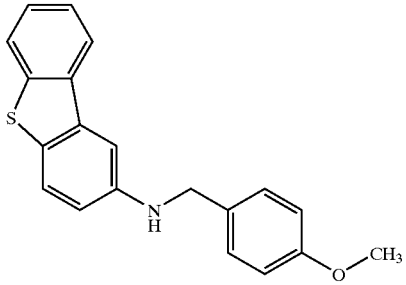 | 2 | 320 | C20H17NOS |
| 378 | 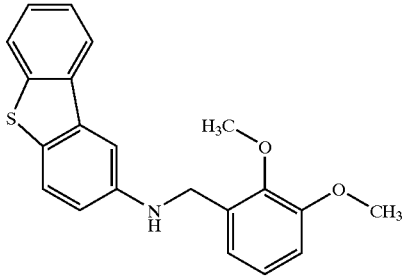 | 2 | 350 | C21H19NO2S |
| 379 | 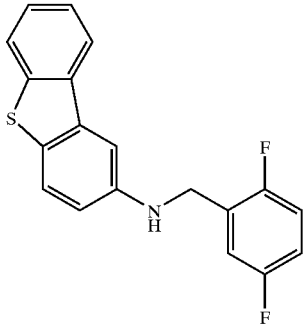 | 2 | 326 | C19H13F2NS |
| 380 | 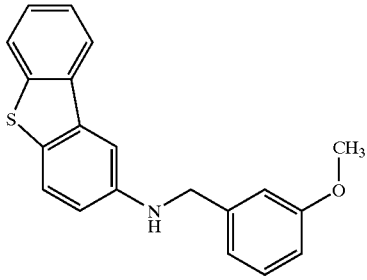 | 2 | 320 | C20H17NOS |

-continued

| Example | MOLSTRUCTURE | General procedure | M + H (APCl)* | MOLECULAR FORMULA |
|---|---|---|---|---|
| 381 | | 2 | 344 | C19H12F3NS |
| 382 | | 2 | 369 | C19H14BrNS |
| 383 | | 2 | 348 | C21H17NO2S |
| 384 | | 2 | 338 | C20H16FNOS |

-continued

| Example | MOLSTRUCTURE | General procedure | M + H (APCl)* | MOLECULAR FORMULA |
|---------|--------------|-------------------|---------------|-------------------|
| 385 | | 2 | 318 | C21H19NS |
| 386 | | 2 | 296 | C17H13NS2 |
| 387 | | 2 | 340 | C23H17NS |
| 388 | | 2 | 358 | C20H14F3NS |
| 389 | | 2 | 340 | C23H17NS |

-continued

| Example | MOLSTRUCTURE | General procedure | M + H (APCl)* | MOLECULAR FORMULA |
|---|---|---|---|---|
| 390 | | 2 | 334 | C21H19NOS |
| 391 | | 2 | 333 | C22H21FN2 |
| 392 | | 2 | 315 | C22H22N2 |
| 393 | | 2 | 329 | C23H24N2 |
| 394 | | 2 | 357 | C25H28N2 |

-continued

| Example | MOLSTRUCTURE | General procedure | M + H (APCI)* | MOLECULAR FORMULA |
|---|---|---|---|---|
| 395 | | 2 | 334,336 | C21H19ClN2 |
| 396 | | 2 | 337 | C21H18F2N2 |
| 397 | | 2 | 355 | C21H17F3N2 |
| 398 | | 2 | 319 | C21H19FN2 |
| 399 | | 2 | 361 | C23H24N2O2 |

-continued

| Example | MOLSTRUCTURE | General procedure | M + H (APCI)* | MOLECULAR FORMULA |
|---|---|---|---|---|
| 400 | | 2 | 301 | C21H20N2 |
| 401 | | 2 | 331 | C22H22N2O |
| 402 | | 2 | 361 | C23H24N2O2 |
| 403 | | 2 | 337 | C21H18F2N2 |
| 404 | | 2 | 331 | C22H22N2O |
| 405 | | 2 | 355 | C21H17F3N2 |

-continued

| Example | MOLSTRUCTURE | General procedure | M + H (APCl)* | MOLECULAR FORMULA |
|---|---|---|---|---|
| 406 | | 2 | 380 | C21H19BrN2 |
| 407 | | 2 | 359 | C23H22N2O2 |
| 408 | | 2 | 349 | C22H21FN2O |
| 409 | | 2 | 329 | C23H24N2 |
| 410 | | 2 | 307 | C19H18N2S |

-continued

| Example | MOLSTRUCTURE | General procedure | M + H (APCl)* | MOLECULAR FORMULA |
|---|---|---|---|---|
| 411 | | 2 | 351 | C25H22N2 |
| 412 | | 2 | 369 | C22H19F3N2 |
| 413 | | 2 | 351 | C25H22N2 |
| 414 | | 2 | 345 | C23H24N2O |
| 415 | | 2 | 337 | C20H17FN2S |

-continued

| Example | MOLSTRUCTURE | General procedure | M + H (APCl)* | MOLECULAR FORMULA |
|---|---|---|---|---|
| 416 | phenothiazine-NH-CH2-(2,4-dimethylphenyl) | 2 | 333 | C21H20N2S |
| 417 | phenothiazine-NH-CH2-(4-tert-butylphenyl) | 2 | 361 | C23H24N2S |
| 418 | phenothiazine-NH-CH2-(2-chlorophenyl) | 2 | 338, 340 | C19H15ClN2S |
| 419 | phenothiazine-NH-CH2-(2,6-difluorophenyl) | 2 | 341 | C19H14F2N2S |
| 420 | phenothiazine-NH-CH2-(2,3,6-trifluorophenyl) | 2 | 359 | C19H13F3N2S |

-continued

| Example | MOLSTRUCTURE | General procedure | M + H (APCl)* | MOLECULAR FORMULA |
|---|---|---|---|---|
| 421 | | 2 | 323 | C19H15FN2S |
| 422 | | 2 | 365 | C21H20N2O2S |
| 423 | | 2 | 305 | C19H16N2S |
| 424 | | 2 | 335 | C20H18N2OS |

-continued

| Example | MOLSTRUCTURE | General procedure | M + H (APCl)* | MOLECULAR FORMULA |
|---|---|---|---|---|
| 425 | | 2 | 341 | C19H14F2N2S |
| 426 | | 2 | 359 | C19H13F3N2S |
| 427 | | 2 | 363 | C21H18N2O2S |
| 428 | | 2 | 353 | C20H17FN2OS |

-continued

| Example | MOLSTRUCTURE | General procedure | M + H (APCl)* | MOLECULAR FORMULA |
|---|---|---|---|---|
| 429 | | 2 | 333 | C21H2ON2S |
| 430 | | 2 | 311 | C17H14N2S2 |
| 431 | | 2 | 373 | C20H15F3N2S |
| 432 | | 2 | 305 | C20H17FN2 |
| 433 | | 2 | 287 | C20H18N2 |

-continued

| Example | MOLSTRUCTURE | General procedure | M + H (APCI)* | MOLECULAR FORMULA |
|---|---|---|---|---|
| 434 | | 2 | 301 | C21H20N2 |
| 435 | | 2 | 329 | C23H24N2 |
| 436 | | 2 | 306,308 | C19H15ClN2 |
| 437 | | 2 | 309 | C19H14F2N2 |
| 438 | | 2 | 327 | C19H13F3N2 |

-continued

| Example | MOLSTRUCTURE | General procedure | M + H (APCl)* | MOLECULAR FORMULA |
|---|---|---|---|---|
| 439 | | 2 | 333 | C21H20N2O2 |
| 440 | | 2 | 333 | C21H20N2O2 |
| 441 | | 2 | 309 | C19H14F2N2 |
| 442 | | 2 | 327 | C19H13F3N2 |

-continued

| Example | MOLSTRUCTURE | General procedure | M + H (APCl)* | MOLECULAR FORMULA |
|---------|--------------|-------------------|---------------|-------------------|
| 443 | | 2 | 331 | C21H18N2O2 |
| 444 | | 2 | 301 | C21H20N2 |
| 445 | | 2 | 323 | C23H18N2 |
| 446 | | 2 | 323 | C23H18N2 |

*Analysis was done by LCMS. Number shown is M + 1. In all cases mass shown agrees with the expected mass for the compound shown.

The following compounds were prepared according to the general procedure 1:

| Example | Structure | MS (M + H) APCI | ¹H-NMR in CDCl₃ unless otherwise noted (δ) | Mp (° C.) |
|---|---|---|---|---|
| 26 | 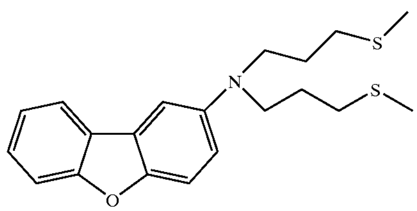 | 360 | 7.90(1H, d); 7.51(1H, d); 7.44–7.26(4H, m); 6.95(1H, d); 3.46(4H, t); 2.58(4H, t); 2.12(6H, s); 1.91(4H, quintet) | — |
| 55 | 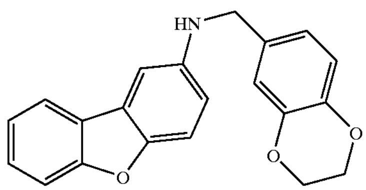 | 332 | 7.87(1H, d); 7.52(1H, d); 7.38–7.46(2H, quartet); 7.25–7.35(1H, t); 7.14(1H, s); 6.97–6.86(3H, m); 6.76–6.81(1H, d); 4.31 (2H, s) 4.25(4H, br s) | — |
| 447 | 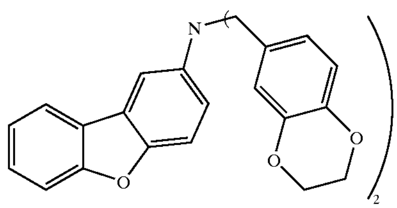 | 480 | 7.81(1H, d); 7.48(1H, d); 7.34–7.41(2H, m); 7.22–7.28(2H, t); 6.88–6.92(1H, d); 6.74–6.86(6H, m); 4.56(4H, br s); 4.23(8H, br s) | — |
| 448 | 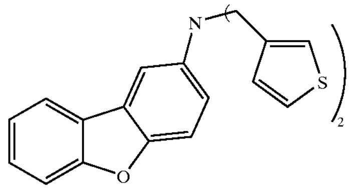 | 376 | 7.85(1H, d); 7.51(1H, d); 7.26–7.42(6H, m); 7.08(2H, br s); 6.99–7.06(3H, m); 4.60(4H, br s) | 109–110 |
| 59 | 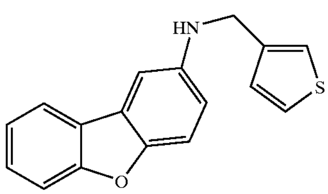 | 280 | 7.86(1H, d); 7.52(1H, d); 7.38–7.44(2H, m); 7.25–7.35(3H, m); 7.19(1H, s); 7.14(1H, s); 6.81(1H, s); 4.43(2H, s) | 62–63 |
| 56 | 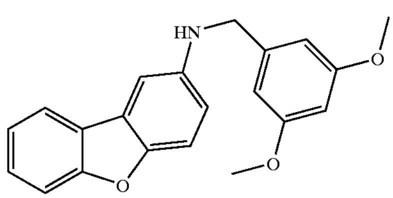 | 334 | 7.86(1H, d); 7.52(1H, d); 7.29–7.42(3H, m); 7.12(1H, s); 6.78(1H, d); 6.60(2H, s); 6.41(1H, t); 4.35(2H, s); 3.79(6H, s) | 87–88 |
| 63 | 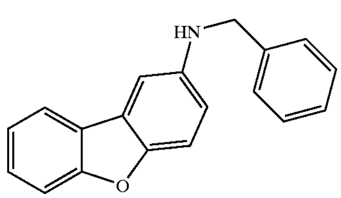 | 274 | 7.89(1H, d); 7.53(1H, d); 7.31–7.48(8H, m); 7.18(1H, s); 6.81(1H, d); 4.43(2H, s); 4.10(1H, br s) | 81–82 |

-continued

| Example | Structure | MS (M + H) APCI | ¹H-NMR in CDCl₃ unless otherwise noted (δ) | Mp (° C.) |
|---|---|---|---|---|
| 61 | 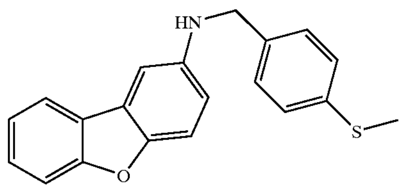 | 320 | IN DMSO 7.93(1H, d); 7.54(1H, d); 7.17–7.42(8H, m); 6.81(1H, d); 6.22(1H, t); 4.30(2H, d); 2.41(3H, s) | 103–104 |
| 73 | 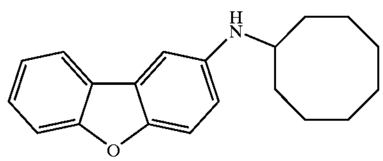 | 294 | 7.90(1H, d); 7.51(1H, d); 7.36–7.44(2H, quartet); 7.26–7.33(1H, t); 7.09(1H, s); 6.72(1H, d); 3.60(2H, br m); 1.95(2H, br m); 1.61 (12H, br m) | 50–52 |
| 57 | 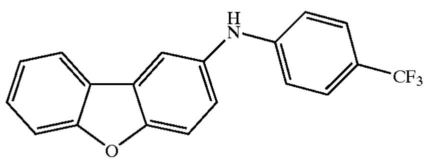 | 342 | 7.86(1H, d); 7.63(2H, d); 7.54(3H, t); 7.43(2H, quartet); 7.32(1H t); 7.11(1H, s); 6.77(1H, d); 4.46(2H, s) 4.15(1H, br s) | 89–90 |
| 449 | 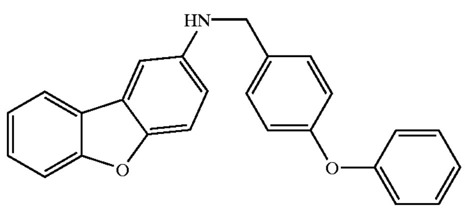 | 364 | 7.90(1H, d); 7.53(1H, d); 7.30–7.45(7H, m); 7.03–7.18(6H, m); 6.81(1H, d); 4.39(2H, s); 4.08(1H, br s) | 91–93 |
| 450 | 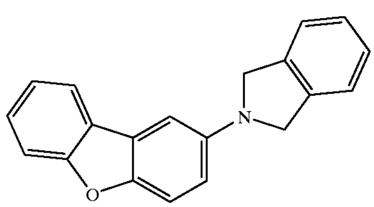 | 286 | 7.96(1H, d); 7.31–7.55(8H, m); 7.15(1H, s); 6.83(1H, d); 4.73(4H, s) | 193–195 |
| 451 | 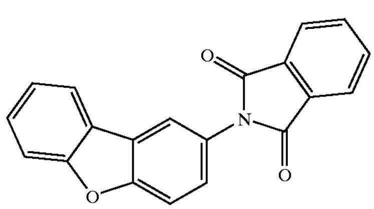 | 314 | IN DMSO 8.22(1H, s); 8.13(1H, d); 7.84–8.01(5H, m); 7.75(1H, d); 7.57(2H, m); 7.43(1H, t) | 217–218 |
| 58 | 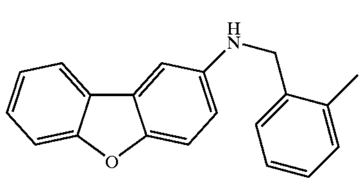 | 288 | 7.95(1H, d); 7.57(1H, d); 7.28–7.41(4H, m); 7.12–7.20(4H, m); 6.87(1H, d); 6.03(1H, t); 4.28(2H, d); 2.36(3H, s) | 84–85 |

-continued
| Example | Structure | MS (M + H) APCI | ¹H-NMR in CDCl₃ unless otherwise noted (δ) | Mp (° C.) |
|---|---|---|---|---|
| 452 | 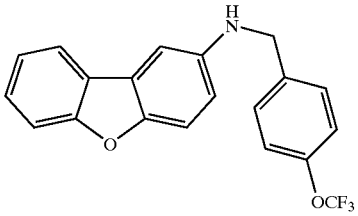 | 358 | 7.85(1H, d); 7.37–7.53(5H, m); 7.20–7.31(3H, m); 7.14(1H, s); 6.90(1H, d); 4.43(2H, s); 4.22(1H, br s) | 75–77 |
| 453 | 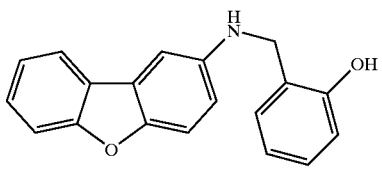 | 290 | 7.86(1H, d); 7.55(1H, d); 7.41–7.47(3H, t); 7.18–7.34(4H, m); 6.89–7.02(3H, m); 4.52(2H, s) | 145–147 |
| 454 | 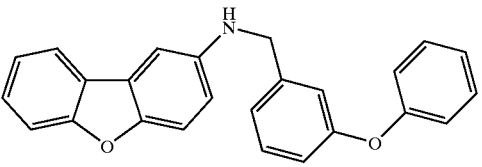 | 366 | 7.85(1H, d); 7.51(1H, d); 7.26–7.44(6H, m); 7.17(1H, d); 7.06–7.13(3H, m); 6.99–7.02(2H, m); 6.95(1H, s); 6.77(1H, dd) 4.40(2H, s); 4.17(1H, s) | 93–94 |
| 54 | 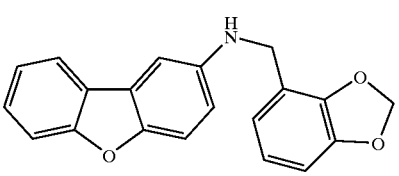 | 316 | 7.86(1H, d); 7.51(1H, d); 7.26–7.43(3H, m); 7.14(1H, s); 6.87–6.92(2H, m); 6.77–6.81(2H, m); 5.96(2H, s); 4.32(2H, s); 4.12(1H, br s) | 85–86 |
| 455 | 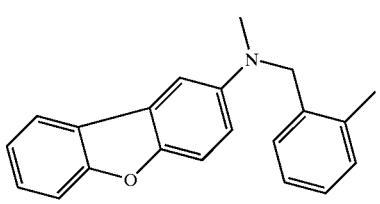 | 302 | 7.99(1H, d); 7.52(1H, d); 7.44–7.39(2H, m); 7.32–7.15(6H, m); 6.89(1H, s); 4.52(2H, s); 3.09(3H, s); 2.37(3H, s) | |
| 456 | 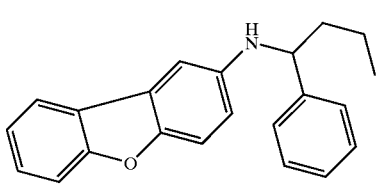 | 316 | 7.77(1H, d); 7.48–7.21(9H, m); 7.00(1H, d); 6.70(1H, dd); 4.40(1H, t); 4.13(1H, br s) 1.88–1.78(2H, m); 1.51–1.38(2H, m); 0.97(3H, t) | — |
| 457 | 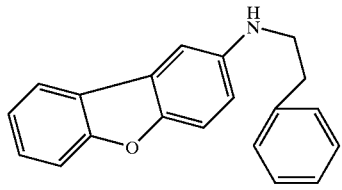 | 392 | 7.87(1H, d); 7.53–7.26(9H, m); 7.16(1H, d); 6.77(1H, dd); 3.50(2H, t); 3.00(2H, t) | — |
| 458 | 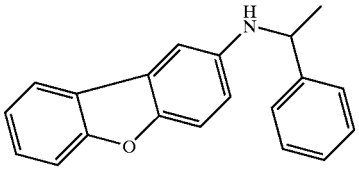 | 288 | 7.76(1H, d); 7.48–7.21(9H, m); 6.99(1H, d); 6.70(1H, dd); 4.57(1H, q); 4.07(1H, br s); 1.57(3H, d) | 94–95 |

| Example | Structure | MS (M + H) APCI | ¹H-NMR in CDCl₃ unless otherwise noted (δ) | Mp (° C.) |
|---|---|---|---|---|
| 202 | 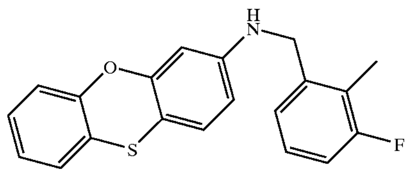 | 338 | 7.09(4H, m), 7.09(3H, m), 6.96(1H, d), 6.30(2H, m), 4.26(sH, s), 2.26(3H, s) | — |
| 210 | 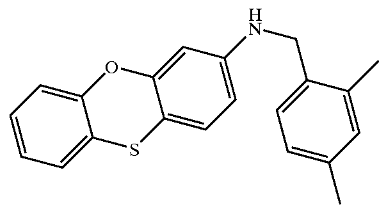 | 334 | 7.26(1H, s), 7.18(1H, d), 7.09(s, 1H), 7.07(1H, s), 7.02(1H, s), 6.95(1H, s), 6.97(2H, s), 6.96(1H, s), 6.87(1H, d), 6.36(1H, s), 6.34(1H, d), 4.2(2H, s), 2.31 (6H, s). | — |
| 135 | 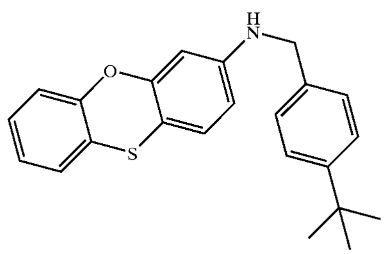 | 362 | 7.26(1H, s), 7.18(1H, d), 7.09(s, 1H), 7.07(1H, s), 7.02(1H, s), 6.95(1H, s), 6.97(2H, s), 6.96(1H, s), 6.87(1H, d), 6.36(1H, s), 6.34(1H, d), 4.2(2H, s), 1.3(9H, s). | — |
| 146 | 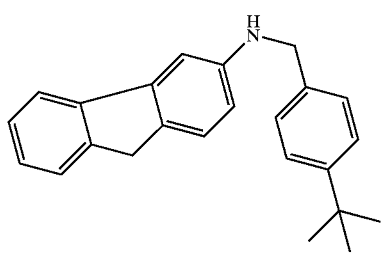 | 328 | 7.61(d, 1H), 7.58(d, 1H), 7.45(d, 1H), 7.39(d, 1H), 7.37(s, 1H), 7.34(s, 1H), 7.32(s, 1H), 7.28(d, 1H), 7.16(t, 1H), 6.86(s, 1H), 6.68(dd, 1H), 4.35(s, 3H), 3.8(s, 2H), 1.31(s, 9H). | — |
| 90 | 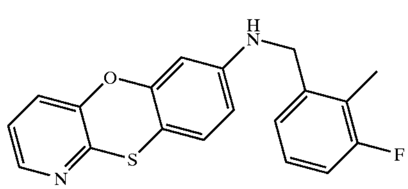 | 339 | 8.15(d, 1H), 7.22(s, 1H), 7.05(m, 3H), 6.98(m, 2H), 6.88(d, 1H), 6.32(d, 1H), 6.29(s, 1H), 4.3(s, 2H), 2.3(s, 3H). | — |

Antiviral Activity Assays:

Screening assays: Anti-herpes simplex virus 1 (HSV) activity is determined in a yield reduction assay utilizing a recombinant HSV (HSV US3:: pgC-lacZ) which expresses *E. coli* β-galactosidase (β-gal) under the control of an HSV late gene promoter (Fink, D. J.; Sternberg, L. R.; Weber, P. C.; Mata, M; Goins, W. F.; Glorioso, J. C. Human Gene Therapy 3:11–19, 1992). Vero (African Green Monkey kidney) cells are infected at a multiplicity of infection of 0.01 with the virus, and serial dilutions of the compound in dimethyl sulfoxide (DMSO) are added. The final concentration of DMSO in all wells is 1%. DMSO is added to control wells. The infection is allowed to proceed for 2 days at which time the β-gal activity in cell lysates is measured. Activity in wells containing compound is compared to control wells and percent inhibition determined. The $EC_{50}$ is defined as the concentration of drug that produces a 50% reduction in β-gal production relative to control wells.

Anti-human cytomegalovirus (HCMV) activity is determined in a yield reduction assay utilizing a recombinant HCMV (RC256) that produces β-gal (Spaete, R. R.; Mocarski, E. S. Proceedings of the National Academy of Sciences USA 84:7213–7217, 1987). Primary human diploid fibroblasts (HFF cells) are infected at an moi of 0.01 with RC256, and serial dilutions of the compound in DMSO are added. The final concentration of DMSO in all wells is 1%. The infection is allowed to proceed for 7 days at which time the β-gal activity in cell lysates is measured. Activity in wells containing compound is compared to control wells and percent inhibition determined. The $EC_{50}$ is defined as the concentration of compound that produces a 50% reduction in β-gal production relative to control wells. $TC_{50}$ is defined as concentration of compound that produces cytotoxicity in 50% of uninfected cells.

Secondary yield reduction assays: To determine the activity of compounds against HSV, Vero cells are plated in 6 well dishes at a density of $5 \times 10^5$ cells/well. Cells are infected at a multiplicity of infection of 0.01 with HSV (strain Syn17+). 30 μL of one of six threefold serial dilutions of test compound in DMSO is added to each well at the time of infection. The plates are returned to a 37° C. incubator and the infection allowed to proceed for 2 days. Aliquots of the supernatant are harvested, and the virus titer determined. Vero cells in 24 well plates are infected with threefold serial dilutions of supernatant. The virus is allowed to absorb to the monolayer for 1.5 hours, after which it is aspirated and replaced with growth medium containing 0.5% methylcellulose. Plaques are allowed to develop for 5 days, at which time the medium aspirated and the monolayer stained with crystal violet. The plaques are enumerated under law power magnification. Percent inhibition is determined by comparison with the titer from cells infected in the presence of DMSO alone.

To determine the activity of compounds against CMV, HFF cells, plated in 24 well plates at $1 \times 10^5$ cells/well, are infected with CMV (strain AD169) at an moi of 0.01. 10 μL of one of six threefold dilutions of test compound in DMSO is added to each well at the time of infection. The plates are returned to a 37° C. incubator and the infection allowed to proceed for 7 days. Aliquots of the supernatant of infected cells are harvested and the virus titer determined. HFF cells in 24 well plates are infected with threefold serial dilutions of supernatant. The virus is allowed to adsorb to the cells for 2 hours, at which time the inoculum is aspirated and replaced with growth medium containing 0.5% methylcellulose. The plaques are allowed to develop for 7–10 days, at which time the medium is aspirated and the monolayer stained with crystal violet. The plaques are enumerated under low power magnification. Percent inhibition is determined by comparison with the titer from cells infected in the presence of DMSO alone.

Cellular toxicity assays: Cellular toxicity is measured in HFF cells. Cells are plated in 96 well plates at $1 \times 10^4$ cells/well. Serial dilutions of compounds are added to the wells in DMSO, with the final concentration of DMSO in all wells at 1%, in a total volume of 200 μL. The plates are maintained in a 37° C. incubator for 7 days. 50 μL of a solution of XTT (sodium-3'[1-(phenyl-amino-carbonyl)-3,-tetrazolium]-bis(bis(4-methoxy-6-nitro)-benzene sulfonic acid hydrate) ($3 \times 10^{-4}$ mg/ml) is added to each well, and the plates returned to the incubator for 4 hours, after which the $A_{450}$ (absorbance at wavelength of 450 nm) for each well is measured in a plate reader. (Roehm, N. W., et al J. Immunol. Meth. 142:257–265, 1991). Toxicity is determined by comparison of the OD (optical density) of a well containing compound to the OD of wells containing DMSO only.

The effect of test compounds on cellular DNA synthesis is measured in a $^{14}$C-thymidine incorporation assay, utilizing scintillation proximity assay technology. Cells are plated at $2 \times 10^4$ cells/well in Amersham Cytostar 96 well scintillating microplates. The following day, serial dilutions of test compounds in DMSO are added to the wells, along with 0.1 μCi/well of [methyl-$^{14}$C]-thymidine (specific activity 50–62 mCi/mmol). The plates are counted immediately in a μBeta scintillation counter (Wallac), to determine background, then placed in a 37° C. incubator for 7 days. The plates are removed from the incubator at intervals and the thymidine incorporation into the cellular DNA determined by scintillation counting. Percent inhibition is determined by comparing $^{14}$C incorporation in wells containing test compound to incorporation in wells containing DMSO only.

Table 3 contains the results of the antiviral efficacy (HSV: $EC_{50}$, $TC_{50}$ and TI) screening results, where TI is the therapeutic index ($TC_{50}/EC_{50}$).

TABLE 3

Antiviral Efficacy in a Yield Reduction Assay (HSV-1)

Antiviral Efficacy (Vero Cells)

| Example | $EC_{50}$ (μM) | $TC_{50}$ (μM) | TI ($EC_{50}/TC_{50}$) |
|---|---|---|---|
| 60 | 0.5 | >100 | >200 |
| 57 | 0.81 | >100 | >124 |
| 56 | 0.7 | >100 | >143 |
| 208 | 0.26 | >100 | >385 |
| 217 | 0.32 | >100 | >313 |
| 139 | 0.4 | >100 | >250 |
| 150 | 0.85 | >100 | >118 |
| 93 | 1.3 | >100 | >77 |
| Reference Agent (Acyclovir) | 0.2 | >100 | >500 |

Table 4 contains the results of the antiviral efficacy (HSV: $EC_{50}$, $TC_{50}$ and TI) screening results, where TI is the therapeutic index $TC_{50}/EC_{50}$).

TABLE 4

Antiviral Efficacy in a Yield Reduction Assay (CMV)

Antiviral Efficacy (HFF Cells)

| Example | $EC_{50}$ (μM) | $TC_{50}$ (μM) | TI ($EC_{50}/TC_{50}$) |
|---|---|---|---|
| 61 | 2.9 | >100 | >35 |
| 57 | 1.7 | >100 | >59 |
| 65 | 3.0 | >100 | >33 |
| 60 | 1.3 | >100 | >77 |
| Reference Agent (Ganciclovir) | 2.6 | >100 | >39 |

Tables 3 and 4 indicates that the compounds of the present invention have good to excellent activity in HSV infected cells from HSV pathogenecity at μM to sub-μM concentrations.

While the forms of the invention herein disclosed constitute presently preferred embodiments, many others are possible. It is not intended herein to mention all of the possible equivalent forms or ramifications of the invention. It is understood that the terms used herein are merely descriptive, rather than limiting, and that various changes may be made without departing from the spirit or scope of the invention.

What is claimed is:

1. The present invention provides a compound of the formula and its pharmaceutically acceptable salts, or the compound and its pharmaceutical composition having useful antiviral activity against viruses of the herpes family.

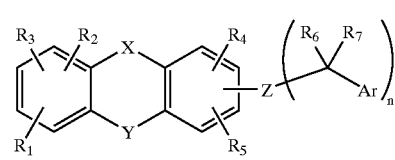

I

Wherein:

X=a chemical bond;

Y=O, S;

Z=N, NH, O, $NHR_8$, $NR_8$, S, SO, $SO_2$;

n=an integer of from 1 to 2;

$R_1$, $R_2$, $R_3$, and $R_5$ independently are hydrogen, halogen, hydroxyl, amino, mono or dialkylamino, cyano, nitro, alkyl groups (1–6 carbon atoms), alkoxy groups (1–6 carbon atoms), $CF_3$, $OCF_3$, aminoalkyl (1–6 carbon atoms), aminoaryl, Oaryl, or a heterocyclic ring having 5–7 atoms with 1–4 hetero atoms of N, O or S and $R_4$ is hydroxyl, alkoxy groups (1–6 carbon atoms) $CF_3$, $OCF_3$, Oaryl or a heterocyclic ring having 5–7 atoms with 1–4 hetero atoms of N, O or S;

Ar=phenyl,
  substituted phenyl,
  benzoheterocyclic ring,
  substituted benzoheterocyclic ring,
  heterocyclic ring or
  substituted-heterocyclic ring, which have substitutions $R_6$ or $R_7$ $R_6$ and $R_7$ are independently hydrogen, alkyl group (1–6 carbon atoms), cycloalkyl (3–12 carbon atoms), halogen, alkoxy, $CF_3$, aminoalkyl (1–6 carbon atoms), aminoaryl, or a heterocyclic ring of from 5–7 atoms with 1–4 heteroatoms of N, O or S;

$R_6$ and $R_7$ may also form a ring, optionally cycloalkyl or aryl or substituted aryl;

$R_8$ is hydrogen, alkyl (1–6 carbon atoms), cycloalkyl (3–8 carbon atoms), phenyl or substituted phenyl wherein the substituents are selected from alkyl group (1–6 carbon atoms), cycloalkyl (3–12 carbon atoms), halogen, alkoxy, $CF_3$, aminoalkyl (1–6 carbon atoms), aminoaryl, or a heterocyclic ring of from 5–7 atoms with 1–4 heteroatoms of N, O or S.

2. The compound of claim 1 having Formula II

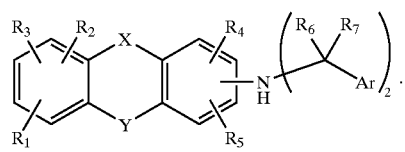

II

3. The compound of claim 1 having Formula III

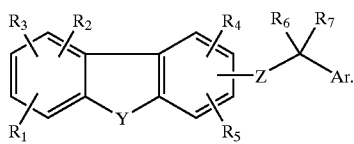

III

4. The compound of claim 1 having Formula IV

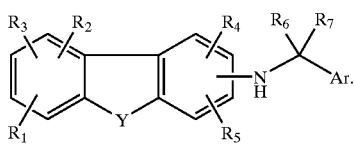

IV

5. The compound of claim 1 having Formula VI

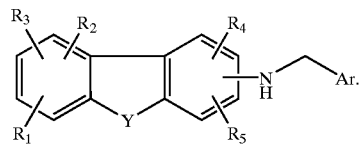

VI

6. A compound having Formula VII

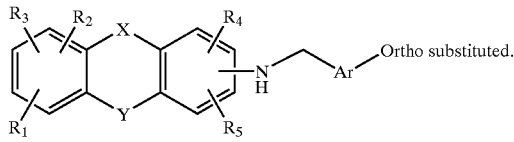

VII

Wherein:

X=a chemical bond;

Y=O, S;

Z=NH;

n=an integer of from 0 to 2;

$R_1$, $R_2$, $R_3$, $R_4$, $R_5$ independently are hydrogen, halogen, hydroxyl, amino, mono or dialkylamino, cyano, nitro, alkyl groups (1–6 carbon atoms), alkoxy groups (1–6 carbon atoms), $CF_3$, $OCF_3$, aminoalkyl (1–6 carbon atoms), aminoaryl, Oaryl, or a heterocyclic ring having 5–7 atoms with 1–4 hetero atoms of N, O or S;

Ar=phenyl,
  substituted phenyl,
  benzoheterocyclic ring,
  substituted benzoheterocyclic ring,
  heterocyclic ring or
  substituted heterocyclic ring, which have substitutions $R_6$ or $R_7$ $R_8$ is hydrogen, alkyl (1–6 carbon atoms), cycloalkyl (3–8 carbon atoms), phenyl or substituted phenyl wherein the substituents are selected from alkyl group (1–6 carbon atoms), cycloalkyl (3–12 carbon atoms), halogen, alkoxy, $CF_3$, aminoalkyl (1–6 carbon atoms), aminoaryl, or a heterocyclic ring of from 5–7 atoms with 1–4 heteroatoms of N, O or S.

7. A pharmaceutical composition for the treatment of infection or disease caused by a herpes virus, which comprises an amount of the compound of claim 1 sufficient to provide an antivirally effective dosage of the compound of Formula I and a pharmaceutically effective carrier.

8. A pharmaceutical composition for the treatment of infection or disease caused by a herpes virus, which comprises an amount of the compound of claim 1 in the range of about 1 to about 50 mg/kg-day or up to 3 g per day and a pharmaceutically effective carrier.

9. A method of treatment of infection or disease caused by a herpes virus, which comprises administering to a subject in need of such treatment a composition of claim 1.

10. A compound selected from the group consisting of:

| | |
|---|---|
| 1 | (1-Cyclopropyl-ethyl)-(2-methoxy-dibenzofuran-3-yl)-amine |
| 5 | Isopropyl-(2-methoxy-dibenzofuran-3-yl)-amine |
| 6 | (2-Methoxy-dibenzofuran-3-yl)-tetrahydro-thiopyran-4-yl)-amine |
| 7 | Cycloheptyl-(2-methoxy-dibenzofuran-3-yl)-amine |
| 8 | (1-Ethyl-propyl)-(2-methoxy-dibenzofuran-3-yl)-amine |
| 9 | sec-Butyl-(2-methoxy-dibenzofuran-3-yl)-amine |
| 15 | (1,1-Dioxo-hexahydro-thiopyran-4-yl)-(2-methoxy-dibenzofuran-3-yl)-amine |
| 16 | Dibenzofuran-2-yl-(3,3,5,5-tetramethyl-cyclohexyl)-amine |
| 17 | (Decahydro-naphthalen-1-yl)-dibenzofuran-2-yl-amine |
| 18 | Adamantan-2-yl-dibenzofuran-2-yl-amine |
| 19 | BicyclohexylA-yl-dibenzofuran-2-yl-amine |
| 20 | Bicyclo[2.2.1]hept-2-yl-dibenzofuran-2-yl-amine |
| 21 | (4-tert-Butylcyclohexyl)-dibenzofuran-2-yl-amine |
| 22 | Bicyclo[3.2.1]oct-2-yl-dibenzofuran-2-yl-amine |
| 23 | Cyclopentyl-dibenzofuran-2-yl-amine |
| 24 | Cyclohexyl-(2-methoxy-dibenzofuran-3-yl)-amine |
| 26 | Dibenzofuran-2-yl-bis-(3-methylsulfanyl-propyl)-amine |
| 27 | Dibenzofuran-2-yl-bis-(3-methyl-butyl)-amine |
| 28 | Dibenzofuran-2-yl-dipropyl-amine |
| 40 | Dibenzofuran-2-yl-(1,1-dioxo-hexahydro-thiopyran-4-yl)-amine |
| 41 | Dibenzofuran-2-yl-piperidin-4-yl-amine |
| 42 | Dibenzofuran-2-yl-isopropyl-amine |
| 43 | Cyclohexyl-dibenzofuran-2-yl-amine |
| 44 | (1-Cyclopropyl-ethyl)-dibenzofuran-2-yl-amine |
| 45 | Dibenzofuran-3-yl-(1,1-dioxo-hexahydro-thiopyran-4-yl)-amine |
| 46 | Dibenzofuran-3-yl-piperidin-4-yl-amine |
| 47 | Dibenzofuran-3-yl-isopropyl-amine |
| 48 | Dibenzofuran-3-yl-(tetrahydro-thiopyran-4-yl)-amine |
| 49 | Cyclohexyl-dibenzofuran-3-yl-amine |
| 50 | Cycloheptyl-dibenzofuran-3-yl-amine |
| 51 | (4-Chloro-benzyl)-dibenzofuran-2-yl-amine |
| 52 | (4-Chloro-3-nitro-benzyl)-dibenzofuran-2-yl-amine |
| 53 | Dibenzofuran-2-yl-(3-trifluoromethoxy-benzyl)-amine |
| 54 | Benzo[1,3]dioxol-5-ylmethyl-dibenzofuran-2-yl-amine |
| 55 | Dibenzofuran-2-yl-(2,3-dihydro-benzo[1,4]dioxin-ylmethyl)-amine |
| 56 | Dibenzofuran-2-yl-(3,5-dimethoxy-benzyl)-amine |
| 57 | Dibenzofuran-2-yl-(4-trifluoromethyl-benzyl)-amine |
| 58 | Dibenzofuran-2-yl-(2-methyl-benzyl)-amine |
| 59 | Dibenzofuran-2-yl-thiophen-3-ylmethyl-amine |
| 60 | Dibenzofuran-2-yl-(4-nitro-benzyl)-amine |
| 61 | Dibenzofuran-2-yl-(4-methylsulfanyl-benzyl)-amine |
| 62 | Dibenzofuran-2-yl-(4-methyl-benzyl)-amine |
| 63 | Benzyl-dibenzofuran-2-yl-amine |
| 64 | (3-Benzyloxy-benzyl)-dibenzofuran-2-yl-amine |
| 65 | (1-Benzyl-butyl)-dibenzofuran-2-yl-amine |
| 66 | Dibenzofuran-2-yl-[2(2-methoxy-phenyl)-1-methyl-ethyl]-amine |
| 67 | 3-(Dibenzofuran-2-ylamino)-2-methyl-butan-1-ol |
| 68 | Dibenzofuran-2-yl-(1-ethyl-butyl)-amine |
| 69 | Dibenzofuran-2-yl-(1-ethyl-propyl)-amine |
| 70 | Dibenzofuran-2-yl-(1,3-dimethyl-butyl)-amine |
| 71 | (1-Cyclohexyl-ethyl)-dibenzofuran-2-yl-amine |
| 72 | Cyclooctyl-dibenzofuran-2-yl-amine |
| 73 | Cycloheptyl-dibenzofuran-2-yl-amine |
| 74 | Dibenzofuran-2-yl-(tetrahydro-thiopyran-4-yl)-amine |
| 75 | Dibenzofuran-2-yl-(tetrahydro-thiophen-3-yl)-amine |
| 76 | Dibenzofuran-2-yl-(1,2-dimethyl-propyl)-amine |
| 77 | Dibenzofuran-2-yl-(1-methyl-butyl)-amine |
| 78 | sec-Butyl-dibenzofuran-2-yl-amine |
| 79 | Benzofuro[3,3-b]pyridin-8-yl-(2-fluoro-benzyl)-amine |
| 80 | Benzofuro[3,3-b]pyridin-8-yl-pyridin-4-ylmethyl-amine |
| 81 | Benzofuro[3,3-b]pyridin-8-yl-(2-methyl-benzyl)-amine |
| 82 | N-(2-Fluoro-benzyl)-N'-methyl-dibenzofuran-2,8-diamine |
| 83 | N-Methyl-N'-quinolin-4-ylmethyl-dibenzofuran-2,8-diamine |
| 84 | N-Methyl-N'-naphthanlen-1-ylmethyl-dibenzofuran-2,8-diamine |
| 85 | N-(4-Methanesulfonyl-benzyl)-N'-methyl-diebnzofuran-2,8-diamine |
| 86 | N-Methyl-N'-pyridin-4-ylmethyl-dibensofuran-2,8-diamine |
| 87 | N-Methyl-N'-(2-methyl-benzyl)-dibenzofuran-2,8-diamine |
| 107 | 8-(3-Fluoro-2-methyl-benzylamino)-dibnzofuran-2-ol |
| 108 | 8-(2-Fluoro-benzylamino)-dibenzofuran-2-ol |
| 109 | 8-(4-Methanesulfonyl-benzylamino)-dibenzofuran-2-ol |
| 110 | 8-[(Pyridin-4-ylmethyl)-amino]-dibenzofuran-2-ol |
| 111 | 8-(2-Methyl-benzylamino)-dibenzofuran-2-ol |
| 112 | (8-Chloro-dibenzofuran-2-yl)-(2-fluoro-benzyl)-amine |
| 113 | (8-Chloro-dibenzofuran-2-yl)-naphthalen-1-ylmethyl-amine |
| 114 | (8-Chloro-dibenzofuran-2-yl)-(4-methanesulfonyl-benzyl)-amine |
| 117 | Benzofuro[3,2-b]pyridin-8-yl-(3-fluoro-2-methyl-benzyl)-amine |
| 118 | Dibenzofuran-2-yl-quinolin-4-ylmethyl-amine |

-continued

| | |
|---|---|
| 119 | Dibenzofuran-2-yl-quinolin-2-ylmethyl-amine |
| 120 | (4-Dimethylamino-benzyl)-(8-fluoro-dibenzofuran-2-yl)-amine |
| 121 | Dibenzofuran-2-yl-(4-dimethylamino-benzyl)-amine |
| 122 | Diebnzofuran-2-yl-(5-nitro-thiophen-2-ylmethyl)-amine |
| 123 | Dibenzofuran-2-yl-thiazol-2-ylmethyl-amine |
| 124 | Benzyl-(8-fluoro-dibenzofuran-2-yl)-amine |
| 125 | N-(-3-Methoxybenzyl)-N'methyl-dibenzofuran-2,8-diamine |
| 126 | N-(3,5-Dimethoxybenzyl)-N'-methyl-dibenzofuran-2,8-diamine |
| 127 | N-(4-tert-Butyl-benzyl)-N'-methyl-dibenzofuran-2,8-diamine |
| 128 | N-Benzyl-N'-methyl-dibenzofuran-2,8-diamine |
| 129 | 2-[(8-Methylamino-dibenzofuran-2-ylamino)-methyl]-benzonitrile |
| 131 | (8-Chloro-dibenzofuran-2-yl)-(3-methoxy-benzyl)-amine |
| 138 | (8-Chloro-dibenzofuran-2-yl)-(3,5-dimethoxy-benzyl)-amine |
| 139 | (8-Chloro-dibenzofuran-2-yl)-(3-fluoro-4-methoxy-benzyl)-amine |
| 140 | Benzyl-(8-chloro-dibenzofuran-2-yl)-amine |
| 142 | (8-Chloro-dibenzofuran-2-yl)-thiazol-2-ylmethyl-amine |
| 150 | Dibenzofuran-4-yl-(4-methoxy-benzyl)-amine |
| 151 | 2-[(8-Chloro-dibenzofuran-2-ylamino)-methyl]-benzonitrile |
| 152 | Dibenzofuran-4-yl-(3-methoxy-benzyl)-amine |
| 153 | Dibenzofuran-4 yl-(3,5-dimethoxy-benzyl)-amine |
| 154 | Dibenzofuran-4-yl-(3-fluoro-4-methoxy-benzyl)-amine |
| 155 | (4-tert-Butyl-benzyl)-dibenzofuran-4-yl-amine |
| 156 | Dibenzofuran-4-yl-(2-ethoxy-benzyl)-amine |
| 157 | N-(4-Methoxy-benzyl)-N'-methyl-dibenzofuran-2,8-diamine |
| 158 | (8-Chloro-dibenzofuran-2-yl)(4-methoxy-benzyl)-amine |
| 159 | (8-Chloro-dibenzofuran-2-yl)-(2-ethoxy-benzyl)-amine |
| 160 | Dibenzofuran-4-yl-(2,4-dimethyl-benzyl)-amine |
| 161 | N-Methyl-N'-thiophen-3-ylmethyl-dibenzofuran-2,8-diamine |
| 162 | N-Methyl-N'-pyridin-2-ylmethyl-dibenzofuran-2,8-diamine |
| 169 | (8-Chloro-dibenzofuran-2-yl)-thiophen-3-ylmethyl-amine |
| 171 | (8-Chloro-dibenzofuran-2-yl)-(3-methyl-pyridin-2-ylmethyl)-amine |
| 176 | (8-Chloro-dibenzofuran-2-yl)-pyridin-4-ylmethyl-amine |
| 183 | (8-Chloro-dibenzofuran-2-yl)-pyridin-3-ylmethyl-amine |
| 184 | Dibenzofuran-4-yl-quinolin-4-ylmethyl-amine |
| 185 | Dibenzofuran-4-yl-quinolin-2-ylmethyl-amine |
| 186 | Dibenzofuran-4-yl-thiophen-3-ylmethyl-amine |
| 187 | Dibenzofuran-4-yl-(3-methyl-pyridin-2-ylmethyl)-amine |
| 188 | Dibenzofuran-4-yl-pyridin-4-ylmethyl-amine |
| 189 | Dibenzofuran-4-yl-pyridin-3-ylmethyl-amine |
| 190 | Dibenzofuran-4-yl-pyridin-2-ylmethyl-amine |
| 191 | (2-Bromo-benzyl)-(8-Chloro-dibenzofuran-2-yl)-amine |
| 192 | (8-Chloro-dibenzofuran-2-yl)-pyridin-2-ylmethyl-amine |
| 193 | N-Methyl-N'-(2,3,6-trifluoro-benzyl)-dibenzofuran-2,8-diamine |
| 194 | N-Methyl-N'-(2,3,4-trifluoro-benzyl)-dibenzofuran-2,8-diamine |
| 195 | N-(2,6-Difluoro-benzyl)-N'-methyl-dibenzofuran-2,8-diamine |
| 196 | N-(2,5-Difluoro-benzyl)-N'-methyl-dibenzofuran-2,8-diamine |
| 197 | N-(2,4-Difluoro-benzyl)-N'-methyl-dibenzofuran-2,8-diamine |
| 198 | N-(2,3-Difluoro-benzyl)-N'-methyl-dibenzofuran-2,8-diamine |
| 199 | N-(2,5-Dimethyl-benzyl)-N'-methyl-dibenzofuran-2,8-diamine |
| 200 | N-(2,4-Dimethyl-benzyl)-N'-methyl-dibenzofuran-2,8-diamine |
| 201 | N-(2,3-Dihydro-benzo[1,4]dioxin-6-ylmethyl)-N'-methyl-dibenzofuran-2,8-diamine |
| 203 | (8-Chloro-dibenzofuran-2-yl)-(2,3,6-trifluoro-benzyl)-amine |
| 213 | (8-Chloro-dibenzofuran-2-yl)-(2,3,4-trifluoro-benzyl)-amine |
| 214 | (8-Chloro-dibenzofuran-2-yl)-(2,6-difluoro-benzyl)-amine |
| 215 | (8-Chloro-dibenzofuran-2-yl)-(2,5-difluoro-benzyl)-amine |
| 216 | (8-Chloro-dibenzofuran-2-yl)-(2,4-difluoro-benzyl)-amine |
| 218 | (8-Chloro-dibenzofuran-2-yl)-(2,3-difluoro-benzyl)-amine |
| 229 | (8-Chloro-dibenzofuran-2-yl)-(2,5-dimethyl-benzyl)-amine |
| 238 | (8-Chloro-dibenzofuran-2-yl)-(2,4-dimethyl-benzyl)-amine |
| 239 | Dibenzofuran-4-yl-(2,5-dimethyl-benzyl)-amine |
| 240 | Dibenzofuran-4-yl-(3-fluoro-2-methyl-benzyl)-amine |
| 241 | N-(3-Fluoro-2-methyl-benzyl)-N'-methyl-dibenzofuran-2,8-diamine |
| 242 | (8-Chloro-dibenzofuran-2-yl)-(3-fluoro-2-methyl-benzyl)-amine |
| 243 | (8-Chloro-dibenzofuran-2-yl)-(2,3-dihydro-benzo[1,4]dioxin-6-ylmethyl)-amine |
| 263 | Dibenzofuran-4-yl-(2,5-dimethoxy-benzyl)-amine |
| 264 | Dibenzofuran-4-yl-(2,3-dimethoxy-benzyl)-amine |
| 265 | 2-(Dibenzofuran-4-ylaminomethyl)-phenol |
| 266 | Dibenzofuran-4-yl-(2-methoxy-benzyl)-amine |
| 267 | (2,5-Dimethyoxy-benzyl)-(3-methoxy-dibenzofuran-2-yl)-amine |
| 268 | (2,3-Dimethyoxy-benzyl)-(3-methoxy-dibenzofuran-2-yl)-amine |
| 269 | (2-Methoxy-benzyl)-(3-methoxy-dibenzofuran-2-yl)-amine |
| 270 | Dibenzofuran-2-yl-(2,5-dimethoxy-benzyl)-amine |
| 271 | Dibenzofuran-2-yl-(4-methoxy-benzyl)-amine |
| 272 | (2-Bromo-benzyl)-dibenzofuran-2-yl-amine |
| 273 | (8-Fluoro-dibenzofuran-2-yl)-(3H-imidazol-4-ylmethyl)-amine |
| 274 | 2-[(8-Fluoro-dibenzofuran-2-ylamino)-methyl]-benzonitrile |
| 275 | (2-Ethoxy-benzyl)-(8-fluoro-dibenzofuran-2-yl)-amine |
| 276 | (8-Fluoro-dibenzofuran-2-yl)-(4-methylsulfanyl-benzyl)-amine |

-continued

| | |
|---|---|
| 277 | (2-Bromo-benzyl)-(8-fluoro-dibenzofuran-2-yl)-amine |
| 278 | (8-Fluoro-dibenzofuran-2-yl)-quinolin-4-ylmethyl-amine |
| 279 | (8-Fluoro-dibenzofuran-2-yl)-quinlon-2-ylmethyl-amine |
| 280 | Dibenzofuran-2-yl-naphthalen-1-ylmethyl-amine |
| 281 | (8-Fluoro-dibenzofuran-2-yl)-naphthalen-2-ylmethyl-amine |
| 282 | (8-Fluoro-dibenzofuran-2-yl)-naphthalen-1-ylmethyl-amine |
| 283 | Dibenzofuran-2-yl-(2-nitro-benzyl)-amine |
| 284 | Dibenzofuran-2-yl-(3H-imidazol-4-ylmethyl)-amine |
| 285 | 2-Dibenzofuran-2-ylaminomethyl)-benzonitrile |
| 286 | Dibenzofuran-2-yl-(2-ethoxy-benzy)-amine |
| 287 | Dibenzofuran-2-yl-(3-fluoro-benzyl)-amine |
| 288 | (4-tert-Butyl-benzyl)-dibenzofuran-2-yl-amine |
| 289 | Dibenzofuran-2-yl-(3-fluoro-benzyl)-amine |
| 290 | (2,5-Dimethoxy-benzyl)-(8-fluoro-dibenzofuran-2-yl)-amine |
| 291 | (2,3-Dimethoxy-benzyl)-(8-fluoro-dibenzofuran-2-yl)-amine |
| 292 | (4-Benzyloxy-benzyl)-(8-fluoro-dibenzofuran-2-yl)-amine |
| 293 | (3-Benzyloxy-benzyl)-(8-fluoro-dibenzofuran-2-yl)-amine |
| 294 | (4-Chloro-benzyl)-(8-fluoro-dibenzofuran-2-yl)-amine |
| 295 | (3-Chloro-benzyl)-(8-fluoro-dibenzofuran-2-yl)-amine |
| 296 | (2-Chloro-benzyl)-(8-fluoro-dibenzofuran-2-yl)-amine |
| 297 | 4-[(8-Fluoro-dibenzofuran-2-ylamino)-methyl]-phenol |
| 298 | 3-[(8-Fluoro-dibenzofuran-2-ylamino)-methyl]-phenol |
| 299 | Dibenzofuran-2-yl-(2-fluoro-benzyl)-amine |
| 300 | (8-Fluoro-dibenzofuran-2-yl)-(4-methoxy-benzyl)-amine |
| 301 | (8-Fluoro-dibenzofuran-2-yl)-(3-methoxy-benzyl)-amine |
| 302 | (8-Fluoro-dibenzofuran-2-yl)-(2-methoxy-benzyl)-amine |
| 303 | (8-Fluoro-dibenzofuran-2-yl)-(4-trifluoromethyl-benzyl)-amine |
| 304 | (8-Fluoro-dibenzofuran-2-yl)-(3-trifluoromethyl-benzyl)-amine |
| 305 | (4-tert-Butyl-benzyl)-(8-fluoro-dibenzofuran-2-yl)-amine |
| 306 | (4-Fluoro-benzyl)-(8-fluoro-dibenzofuran-2-yl)-amine |
| 307 | (3-Fluoro-benzyl)-(8-fluoro-dibenzofuran-2-yl)-amine |
| 308 | (2-Fluoro-benzyl)-(8-fluoro-dibenzofuran-2-yl)-amine |
| 309 | (8-Fluoro-dibenzofuran-2-yl)-(4-methyl-benzyl)-amine |
| 310 | (8-Fluoro-dibenzofuran-2-yl)-(3-methyl-benzyl)-amine |
| 311 | Dibenzofuran-2-yl-(2,6-dimethoxy-benzyl)-amine |
| 312 | Dibenzofuran-2-yl-(2,4-dimethoxy-benzyl)-amine |
| 313 | Dibenzofuran-2-yl-(2,3-dimethoxy-benzyl)-amine |
| 314 | (4-Benzyloxy-benzyl)-dibenzofuran-2-yl-amine |
| 315 | Dibenzofuran-2-yl-(3-methyl-benzyl)-amine |
| 316 | (3-Chloro-benzyl)-dibenzofuran-2-yl-amine |
| 317 | 3-(Dibenzofuran-2-ylaminomethyl)-phenol |
| 318 | (2-Chloro-benzyl)-dibenzofuran-2-yl-amine |
| 319 | Dibenzofuran-2-yl-(3-methoxy-benzyl)-amine |
| 320 | Dibenzofuran-2-yl-(2-methoxy-benzyl)-amine |
| 322 | Dibenzofuran-4-yl-(2-methyl-benzyl)-amine |
| 323 | (8-Chloro-dibenzofuran-2-yl)-(2-methyl-benzyl)-amine |
| 326 | Dibenzofuran-2-yl-(2,6-difluoro-benzyl)-amine |
| 327 | Dibenzofuran-2-yl-(2,5-difluoro-benzyl)-amine |
| 328 | Dibenzofuran-2-yl-(2,4-difluoro-benzyl)-amine |
| 329 | Dibenzofuran-2-yl-(2,3-difluoro-benzyl)-amine |
| 330 | (8-Fluoro-dibenzofuran-2-yl)-thiophen-2-ylmethyl-amine |
| 331 | Dibenzofuran-2-yl-(2,5-dimethyl-benzyl)-amine |
| 332 | (8-Fluoro-dibenzofuran-2-yl)-thiophen-3-ylmethyl-amine |
| 333 | (8-Fluoro-dibenzofuran-2-yl)-furan-2-ylmethyl-amine |
| 334 | (8-Fluoro-dibenzofuran-2-yl)-furan-3-ylmethyl-amine |
| 335 | (8-Fluoro-dibenzofuran-2-yl)-(6-methyl-pyridin-2-ylmethyl)-amine |
| 336 | (8-Fluoro-dibenzofuran-2-yl)-(4-methanesulfonyl-benzyl)-amine |
| 337 | (8-Fluoro-dibenzofuran-2-yl)-pyridin-4-ylmethyl-amine |
| 338 | (8-Fluoro-dibenzofuran-2-yl)-pyridin-3-ylmethyl-amine |
| 339 | (8-Fluoro-dibenzofuran-2-yl)-pyridin-2-ylmethyl-amine |
| 340 | (8-Fluoro-dibenzofuran-2-yl)-(3-fluoro-4-methoxy-benzyl)-amine |
| 341 | Dibenzofuran-2-yl-(2,4-dimethyl-benzyl)-amine |
| 342 | (8-Fluoro-dibenzofuran-2-yl)-(3-fluoro-2-methyl-benzyl)-amine |
| 343 | (8-Fluoro-dibenzofuran-2-yl)-(2,3,6-trifluoro-benzyl)-amine |
| 344 | (8-Fluoro-dibenzofuran-2-yl)-(2,3,4-trifluoro-benzyl)-amine |
| 345 | (3,5-Difluoro-benzyl)-(8-fluoro-dibenzofuran-2-yl)-amine |
| 346 | (3,4-Difluoro-benzyl)-(8-fluoro-dibenzofuran-2-yl)-amine |
| 347 | )-(8-fluoro-dibenzofuran-2-yl)-amine |
| 348 | (2,6-Difluoro-benzyl (2,5-Difluoro-benzyl)-(8-fluoro-dibenzofuran-2-yl)-amine |
| 349 | (2,4-Difluoro-benzyl)-(8-fluoro-dibenzofuran-2-yl)-amine |
| 350 | (2,3-Difluoro-benzyl)-(8-fluoro-dibenzofuran-2-yl)-amine |
| 351 | (2,5-Dimethyl-benzyl)-(8-fluoro-dibenzofuran-2-yl)-amine |
| 352 | (2,4-Dimethyl-benzyl)-(8-fluoro-dibenzofuran-2-yl)-amine |
| 353 | (2,3-Dihydro-1,4-benzodioxin-6-ylmethyl)-(8-fluoro-dibenzofuran-2-yl)-amine |
| 354 | (3,5-Dimethoxy-benzyl)-(8-fluoro-dibenzofuran-2-yl)-amine |
| 355 | Dibenzofuran-2-yl-furan-2-ylmethyl-amine |
| 356 | Dibenzofuran-2-yl-furan-3-ylmethyl-amine |
| 357 | Dibenzofuran-2-yl-(6-methyl-pyridin-2-ylmethyl)-amine |
| 358 | Dibenzofuran-2-yl-(4-methanesulfonyl-benzyl)-amine |

-continued

| | |
|---|---|
| 359 | Dibenzofuran-2-yl-pyridin-4-ylmethyl-amine |
| 360 | Dibenzofuran-2-yl-pyridin-3-ylmethyl-amine |
| 361 | Dibenzofuran-2-yl-pyridin-2-ylmethyl-amine |
| 362 | Dibenzofuran-2-yl-(3-fluoro-4-methoxy-benzyl)-amine |
| 363 | Dibenzofuran-2-yl-(3-fluoro-2-methyl-benzyl)-amine |
| 364 | Dibenzofuran-2-yl-(2,3,6-trifluoro-benzyl)-amine |
| 365 | Dibenzofuran-2-yl-(2,3,4-trifluoro-benzyl)-amine |
| 366 | Dibenzofuran-2-yl-(3,5-difluoro-benzyl)-amine |
| 367 | Dibenzofuran-2-yl-(3,4-difluoro-benzyl)-amine |
| 368 | Dibenzofuran-2-yl-(3,4-dimethoxy-benzyl)-amine |
| 369 | Dibenzofuran-2-yl-methyl-(2-methyl-benzyl)-amine |
| 370 | Dibenzothiophen-2-yl-(2,4-dimethyl-benzyl)-amine |
| 371 | (4-tert-Butyl-benzyl)-dibenzothiophen-2-yl-amine |
| 372 | (2-Chloro-benzyl)-dibenzothiophen-2-yl-amine |
| 373 | Dibenzothiophen-2-yl-(2,6-difluoro-benzyl)-amine |
| 374 | Dibenzothiophen-2-yl-(2,3,6-trifluoro-benzyl)-amine |
| 375 | Dibenzothiophen-2-yl-(2-fluoro-benzyl)-amine |
| 376 | Benzyl-dibenzothiophen-2-yl-amine |
| 377 | Dibenzothiophen-2-yl-(4-methoxy-benzyl)-amine |
| 378 | Dibenzothiophen-2-yl-(2,3-dimethoxy-benzyl)-amine |
| 379 | Dibenzothiophen-2-yl-(2,5-difluoro-benzyl)-amine |
| 380 | Dibenzothiophen-2-yl-(3-methoxy-benzyl)-amine |
| 381 | Dibenzothiophen-2-yl-(2,3,4-trifluoro-benzyl)-amine |
| 382 | (-2-Bromo-benzyl)-dibenzothiophen-2-yl-amine |
| 383 | Dibenzothiophen-2-yl-(2,3-dihydro-1,4-benzodioxin-6-ylmethyl)-amine |
| 384 | Dibenzothiophen-2-yl-(3-fluoro-4-methoxy-benzyl)-amine |
| 385 | Dibenzothiophen-2-yl-(2,5-dimethyl-benzyl)-amine |
| 386 | Dibenzothiophen-2-yl-thiophen-3-ylmethyl-amine |
| 387 | Dibenzothiophen-2-yl-naphthalene-1-ylmethyl-amine |
| 388 | Dibenzothiophen-2-yl-(2-trifluoromethyl-benzyl)-amine |
| 389 | Dibenzothiophen-2-yl-naphthalen-2-ylmethyl-amine |
| 390 | Dibenzothiophen-2-yl-(2-ethoxy-benzyl)-amine |
| 447 | Dibenzofuran-2-yl-bis-(2,3-dihydro-benzo[1,4]dioxin-6-ylmethylamine |
| 448 | Dibenzofuran-2-yl-bis-thiophen-3-ylmethyl-amine |
| 449 | Dibenzofuran-2-yl-(4phenoxy-benzyl)-amine |
| 450 | 2-Dibenzofuran-2-yl-2,3-dihydro-1H-isoindole |
| 451 | 2-Dibenzofuran-2-yl-1H-isoindole-1,3-dione |
| 452 | Dibenzofuran-2-yl-(4-trifluoromethoxy-benzyl)-amine |
| 453 | Dibenzofuran-2-yl-(2-methoxy-benzyl)-amine |
| 454 | Dibenzofuran-2-yl-(3-phenoxy-benzyl)-amine |
| 455 | Dibenzofuran-2-yl-methyl(2-methyl-benzyl)-amine |
| 456 | Dibenzofuran-2-yl-(1-phenyl-butyl)-amine |
| 457 | Dibenzofuran-2-yl-phenethyl-amine and |
| 458 | Dibenzofuran-2-yl-(1-phenyl-ethyl)-amine. |

11. A pharmaceutical composition for the treatment of infection or disease caused by a herpes virus, which comprises an amount of the compound of claim 6 sufficient to provide an antivirally effective dosage of the compound of Formula I and a pharmaceutically effective carrier.

12. A pharmaceutical composition for the treatment of infection or disease caused by a herpes virus, which comprises an amount of the compound of claim 1 in the range of about 1 to about 50 mg/kg-day or up to 3 g per day and a pharmaceutically effective carrier.

13. A method of treatment of infection or disease caused by a herpes virus, which comprises administering to a subject in need of such treatment a composition of claim 7.

* * * * *